US 9,945,853 B2

Apr. 17, 2018

(12) United States Patent
Boilard et al.

(54) EXTRACELLULAR MITOCHONDRIAL COMPONENTS FOR DETECTING INFLAMMATORY REACTIONS AND CONDITIONS

(71) Applicants: UNIVERSITE LAVAL, Quebec (CA); HEMA-QUEBEC, Saint-Laurent (CA); UNIVERSITY OF WASHINGTON, Seattle, WA (US)

(72) Inventors: Eric Boilard, Quebec (CA); Luc Boudreau, Dieppe (CA); Louis Thibault, St-Augustin-de-Desmaures (CA); Michael Herman Gelb, Seattle, WA (US)

(73) Assignees: Université Laval, Québec (CA); Hérma-Québec, Saint-Laurent (CA); University of Washington, Seattle, WA (US)

( * ) Notice: Subject to any disclaimer, the term of this patent is extended or adjusted under 35 U.S.C. 154(b) by 0 days.

(21) Appl. No.: 15/028,658

(22) PCT Filed: Oct. 10, 2014

(86) PCT No.: PCT/CA2014/050984
§ 371 (c)(1),
(2) Date: Apr. 11, 2016

(87) PCT Pub. No.: WO2015/051466
PCT Pub. Date: Apr. 16, 2015

(65) Prior Publication Data
US 2016/0258950 A1 Sep. 8, 2016

Related U.S. Application Data

(60) Provisional application No. 61/889,798, filed on Oct. 11, 2013.

(51) Int. Cl.
| | | |
|---|---|---|
| G01N 33/569 | (2006.01) | |
| G01N 33/50 | (2006.01) | |
| G01N 15/14 | (2006.01) | |
| G01N 33/564 | (2006.01) | |
| G01N 15/00 | (2006.01) | |

(52) U.S. Cl.
CPC ....... *G01N 33/56966* (2013.01); *G01N 15/14* (2013.01); *G01N 33/502* (2013.01); *G01N 33/5079* (2013.01); *G01N 33/564* (2013.01); *G01N 2015/0084* (2013.01); *G01N 2015/1486* (2013.01); *G01N 2500/10* (2013.01); *G01N 2800/104* (2013.01); *G01N 2800/222* (2013.01); *G01N 2800/7095* (2013.01)

(58) Field of Classification Search
None
See application file for complete search history.

(56) References Cited

U.S. PATENT DOCUMENTS

2003/0216285 A1  11/2003  Dumont et al. .................. 514/1

FOREIGN PATENT DOCUMENTS

| WO | WO 2012/146783 | 11/2012 |
|---|---|---|
| WO | WO 2013/119193 | 8/2013 |

OTHER PUBLICATIONS

Adibhatla et al. (Antioxidant & Redox Signaling 2003 vol. 5, p. 647-654).*
Li et al. (Mitochondria Disorders 2011 vol. 837, p. 63-72).*
Bollinger, et al. "Improved sensitivity mass spectrometric detection of eicosanoids by charge reversal derivatization", *Anal Chem*, 82(16) : 6790-6796, 2010.
Bollinger et al., "Improved method for the quantification of lysophospholipids including enol ether species by liquid chromatography-tandem mass spectrometry", *J Lipid Res*, 51(2): 440-447, 2010.
Borgeat et al. "Automated on-line extraction and profiling of lipoxygenase products of arachidonic acid by high-performance liquid chromatography", *Methods Enzymol*, 187: 98-116, 1990.
Canaan et al. "Unusual mode of binding of human group IIA secreted phospholipase A2 to anionic interfaces as studied by continuous wave and time domain electron paramagnetic resonance spectroscopy", *J Biol Chem*, 277(34): 30984-30990, 2002.
Clerc, P. & Polster, B. M. "Investigation of mitochondrial dysfunction by sequential microplate-based respiration measurements from intact and permeabilized neurons", *PLoS One*, 7(4): e34465, 2012.
Cloutier et al. "The exposure of autoantigens by microparticles underlies the formation of potent inflammatory components: the microparticle-associated immune complexes", *EMBO Mol Med*, 5: 235-249, 2013.
Dean et al. "Proteomic and functional characterisation of platelet microparticle size classes", *Thromb Haemost*, 102(4): 711-718, 2009.
Dussault et al. "Rapid and simple comparison of messenger RNA levels using real-time PCR", *Biol Proced Online*, 8: 1-10, 2006.
Edwards et al. "The crystal structure of the H48Q active site mutant of human group IIA secreted phospholipase A2 at 1.5 A resolution provides an insight into the catalytic mechanism", *Biochemistry*, 41: 15468-15476, 2002.

(Continued)

*Primary Examiner* — Jacob Cheu
(74) *Attorney, Agent, or Firm* — Norton Rose Fulbright US LLP

(57) ABSTRACT

The present disclosure highlights the relationship between extracellular mitochondrial components, optionally in combination with the secreted phospholipase $A_2$-IIA and/or an auto-antibody, and in vivo as well as in vitro and inflammatory reactions/conditions, especially those released as a result of the degradation of a platelet. The present disclosure provides methods for determining the presence of inflammatory mediators, for limiting inflammatory reactions/conditions, for the diagnosis inflammatory reactions/conditions, for screening therapeutics for the treatment and/or the alleviation of symptoms of inflammatory reactions/conditions based on the detection or modulation of the level of these extracellular mitochondrial components.

14 Claims, 23 Drawing Sheets

(56) References Cited

OTHER PUBLICATIONS

Flamand et al., "Arachidonic acid regulates the translocation of 5-lipoxygenase to the nuclear membranes in human neutrophils", *J Biol Chem*, 281: 129-136, 2006.
Grass et al. "Expression of human group II PLA2 in transgenic mice results in epidermal hyperplasia in the absence of inflammatory infiltrate", *J Clin Invest*, 97(10): 2233-2241, 1996.
Gyorgy et al. "Detection and isolation of cell-derived microparticles are compromised by protein complexes resulting from shared biophysical parameters", *Blood*, 117(4):e39-48, 2011.
György et al. "Membrane vesicles, current state-of-the-art: emerging role of extracellular vesicles", *Cell Mol Life Sci*, 68(16): 2667-2688, 2011.
Gyorgy et al. "Improved flow cytometric assessment reveals distinct microvesicle (cell-derived microparticle) signatures in joint diseases", *PLoS One*, 7(11): e49726, 2012.
Lee et al. "Blood transfusion products contain mitochondrial DNA damage-associated molecular patterns: a potential effector of transfusion-related acute lung injury", *J Surg Res*, 191(2): 286-9, 2014.
Oslund et al. "Biochemical characterization of selective inhibitors of human group IIA secreted phospholipase A(2) and hyaluronic acid-linked inhibitor conjugates", *Biochemistry*, 51(43): 8617-26, 2012.
Simmons et al. "Elevated Levels of Plasma Mitochondrial DNA DAMPs Are Linked to Clinical Outcome in Severely Injured Human Subjects", *Ann Surg*, 258(4): 591-6, discussion 596-8, 2013.
Singer et al. "Interfacial kinetic and binding properties of the complete set of human and mouse groups I, II, V, X, and XII secreted phospholipases $A_2$", *J Biol Chem*, 277(50): 48535-49, 2002.
Soulet et al. "Automated Filtering of Intrinsic Movement Artifacts during Two-Photon Intravital Microscopy", *PLoS One*, 8(1): e53942, 2013.
Sursal et al. "Plasma Bacterial and Mitochondrial DNA Distinguish Bacterial Sepsis from Sterile SIRS and Quantify Inflammatory Tissue Injury in Nonhuman Primates", *Shock*, 39(1): 55-62, 2013.
Thibault et al., "Characterization of blood components prepared from whole-blood donations after a 24-hour hold with the platlet-rich plasma method", *Transfusion*, 46: 1292-1299, 2006.
Touaibia et al, "Inhibition of secreted phospholipase A2. 4-glycerol derivatives of 4,5-dihydro-3-(4-tetradecyloxybenzyl)-1,2,4-4H-oxadiazol-5-one with broad activities", *J Med Chem*, 50(7):1618-26, 2007.
van der Vlist et al. "Fluorescent labeling of nano-sized vesicles released by cells and subsequent quantitative and qualitative analysis by high-resolution flow cytometry", *Nat Protoc*, 7(7): 1311-1326, 2012.
Willoughby DA, Sedgwick AD, Giroud JP, Al-Duaij AY, de Brito F. The use of the air pouch to study experimental synovitis and cartilage breakdown. Biomed Pharmacother. 1986;40(2):45-49.
Hajizadeh et al., "Extracellular mitochondrial DNA and oxidatively damaged DNA in synovial fluid of patients with rheumatoid arthritis", *Arthritis Research and Therapy*, 5(5): R234-R240, 2003.
Krysko et al., "Emerging role of damage-associated molecular patterns derived from mitochondria in inflammation", Trends in Immunology, 32(4): pp. 157-164, 2011.
Zhang et al., "Circulating mitochondrial DAMPs cause inflammatory responses to injury", *Nature*, 464: 104-107, 2010.
Boudreau et al., "Platelets release mitochondrial serving as substrate for bactericidal group IIA-secreted phospholipase $A_2$ to promote inflammation", *Blood*, 124: 2173-2183, 2014.
Garraud et al. "Blood Transfusion and Inflammation," *Transform Clinique et Biologique* 2013; 20: 231-238, (English Translaton Provided).
Boilard et al., "A novel anti-inflammatory role for secretory phospholipase $A_2$ in immune complex-mediated arthritis," *EMBO Molecular Medicine*, 2010; 2: 172-187.
European Search Report in European Application No. 14851546, dated Mar. 27, 2017.
Garraud et al. "Blood transfusion and inflammation," *Transfusion Clinique et Biologique* 2013; 20: 231-238, (English abstract provided).

\* cited by examiner

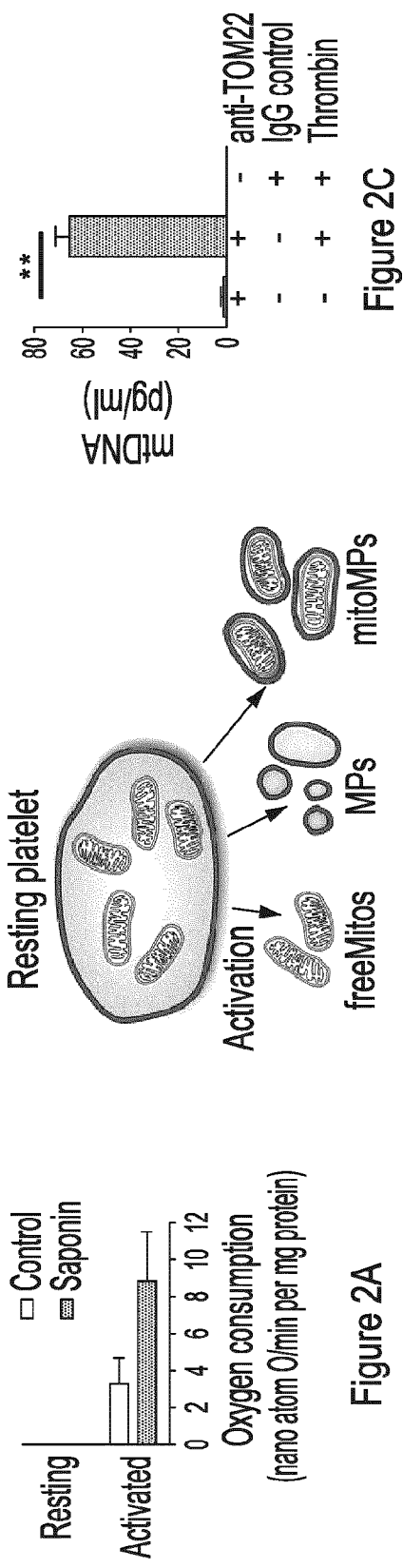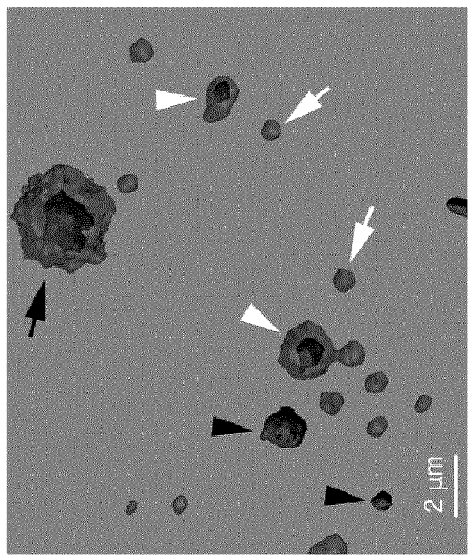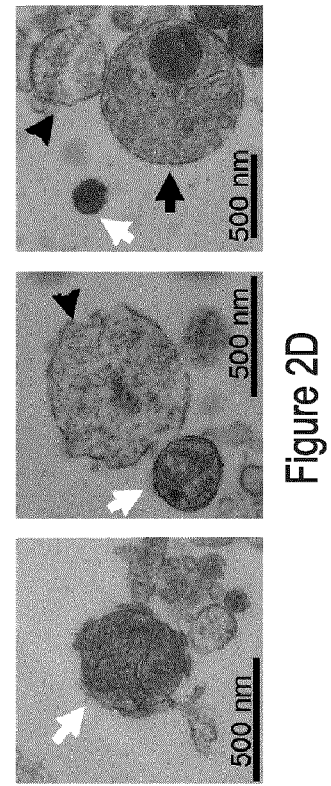
Figure 2A
Figure 2B
Figure 2C
Figure 2D
Figure 2E

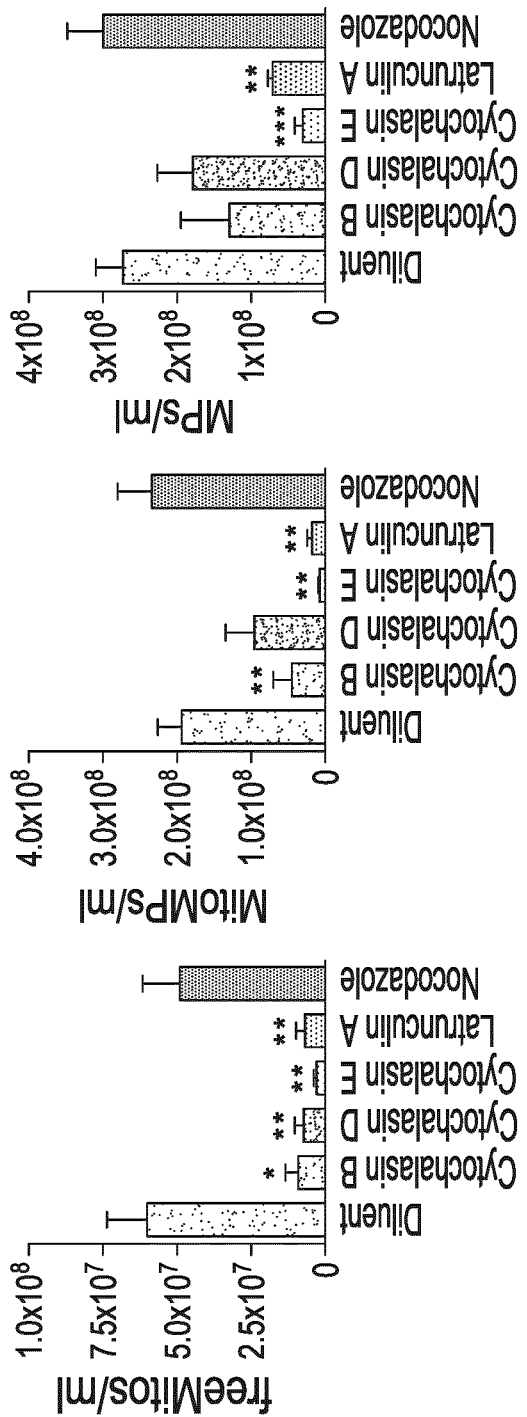
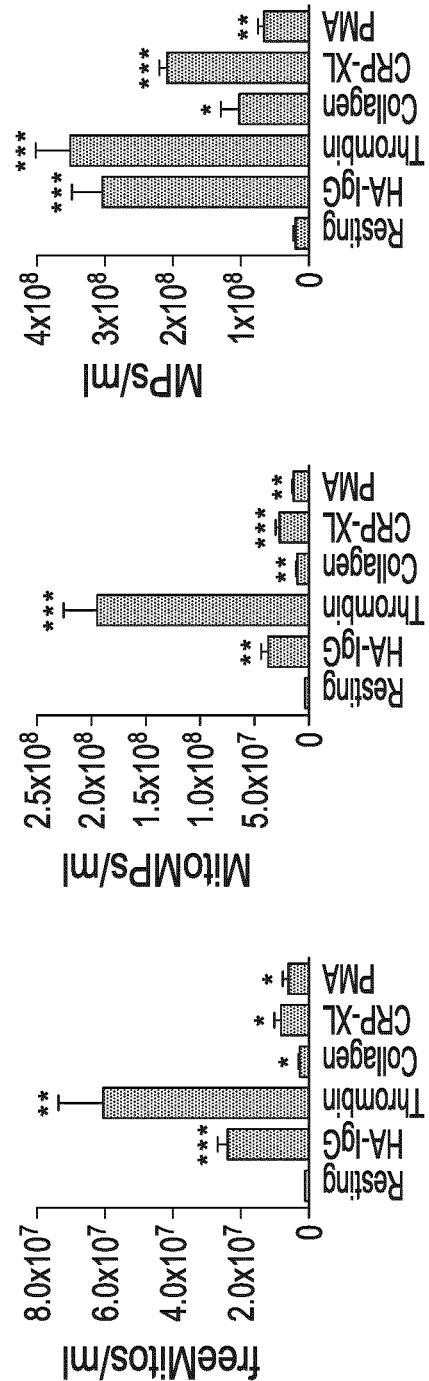
Figure 2G
Figure 2H

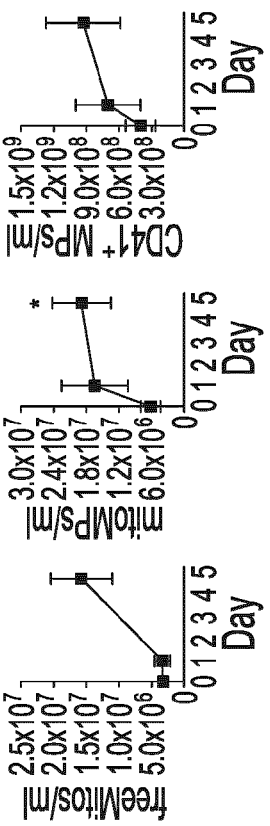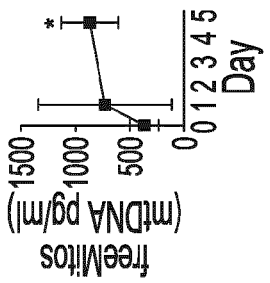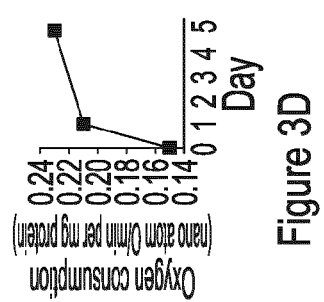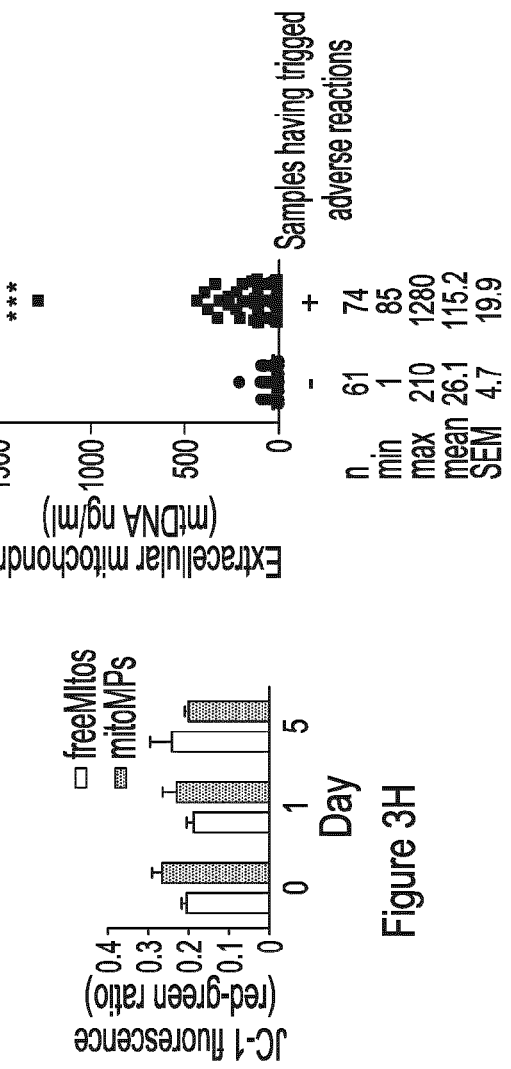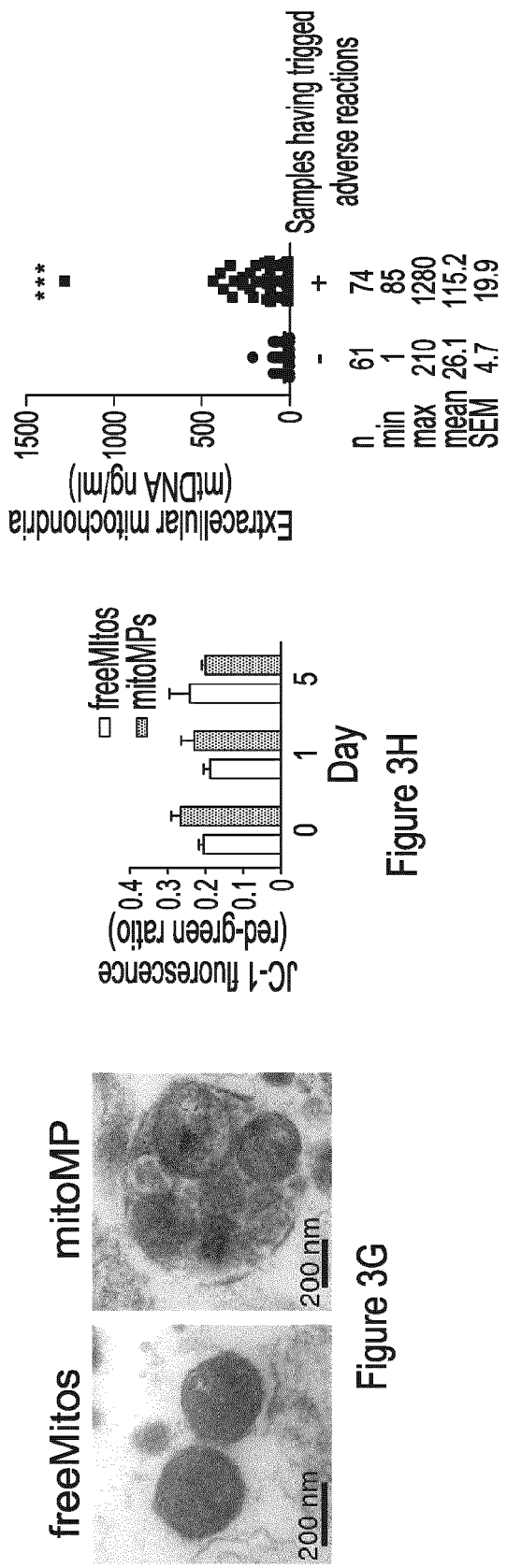
Figure 3D, Figure 3E, Figure 3F, Figure 3G, Figure 3H, Figure 3I

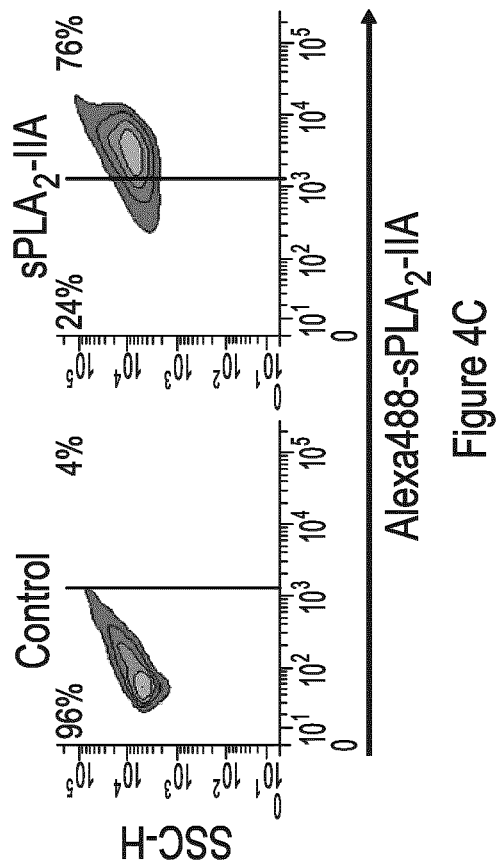
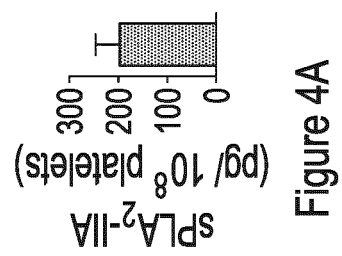
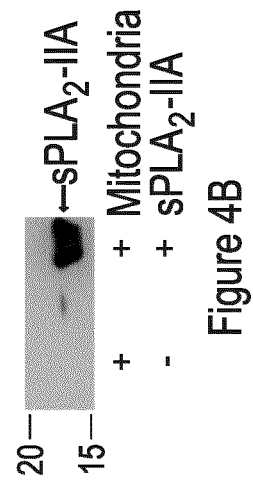

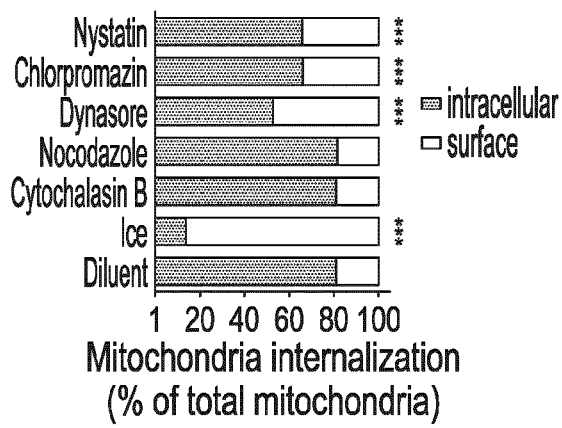
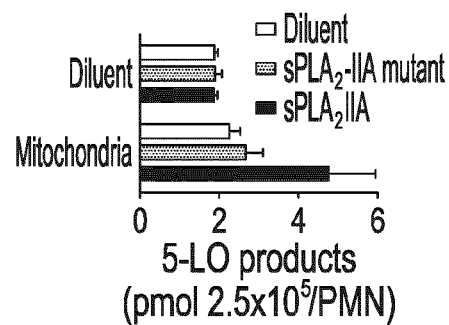
Figure 6C
Figure 6D
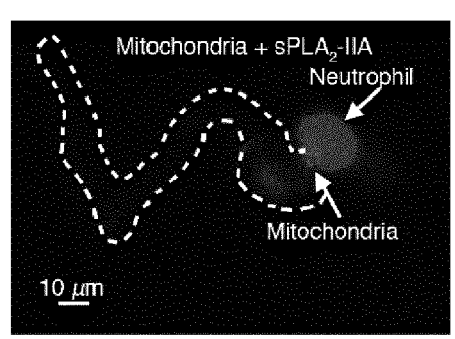
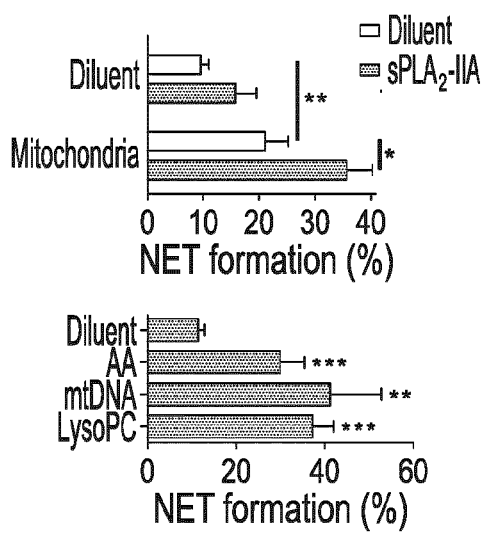
Figure 6E

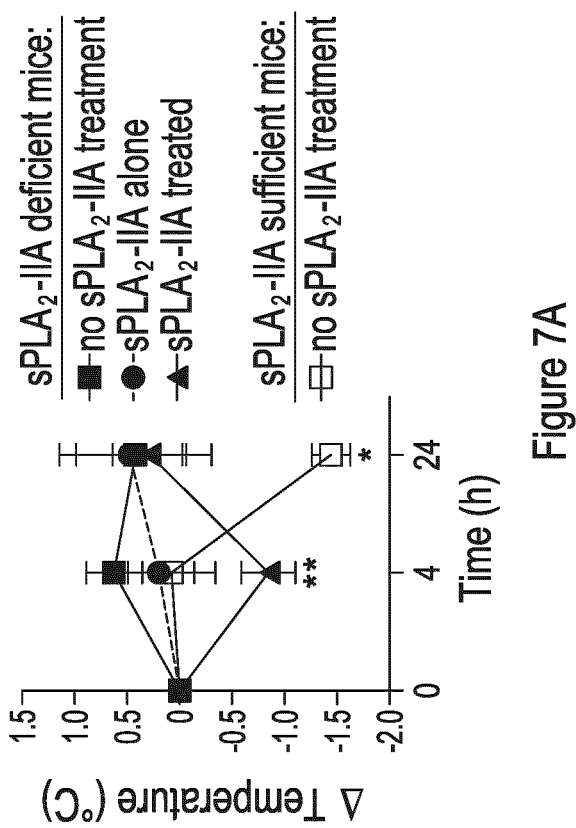
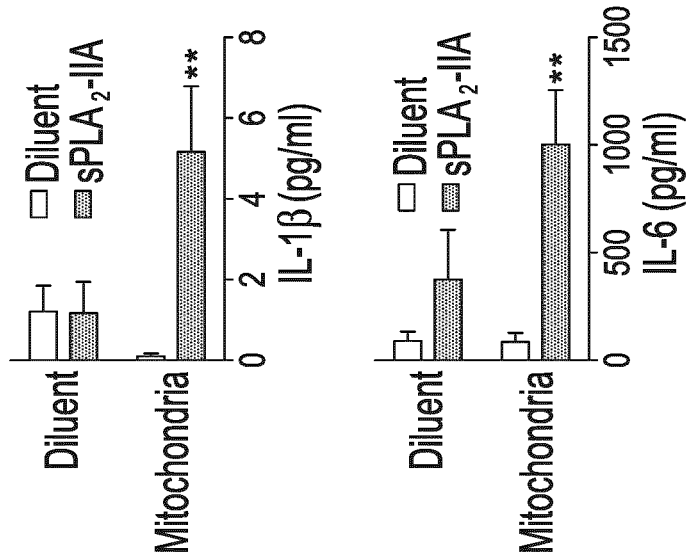
Figure 7A
Figure 7B

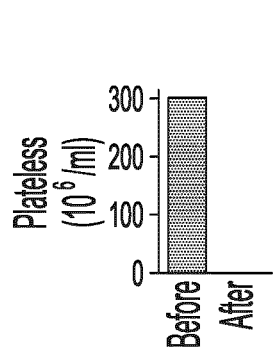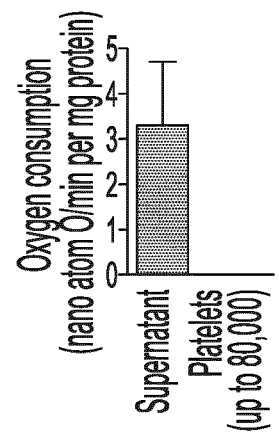
Figure 9A
Figure 9B
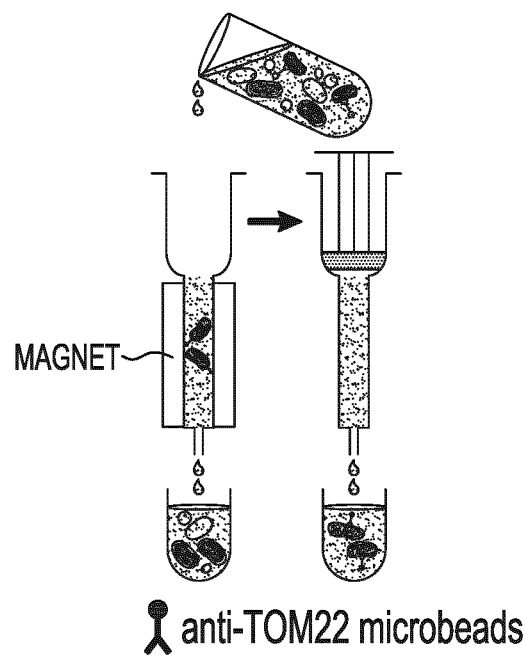
Figure 10

US 9,945,853 B2

EXTRACELLULAR MITOCHONDRIAL COMPONENTS FOR DETECTING INFLAMMATORY REACTIONS AND CONDITIONS

CROSS-REFERENCE TO RELATED APPLICATIONS

This application is a national phase application under 35 U.S.C. § 371 of International Application No. PCT/CA2014/050984 filed Oct. 10, 2014, which claims priority from U.S. Provisional Patent Application Ser. No. 61/889,798 filed on Oct. 11, 2013. The entire contents of each of the above-referenced disclosures is specifically incorporated herein by reference without disclaimer.

STATEMENT OF GOVERNMENT SUPPORT

This invention was made with government support under Grant No. 5 R37 HL036235-29, awarded by the National Institutes of Health. The government has certain rights in the invention.

TECHNOLOGICAL FIELD

The present disclosure relates to the diagnosis, prevention, treatment, alleviation of symptoms of inflammatory conditions or reactions.

BACKGROUND

Platelets are small (2-4 μm) discoid cells released by megakaryocytes present in the bone marrow. During this process, megakaryocytes transfer components to daughter platelets, including messenger RNA and microRNA as well as cytoplasmic organelles. Mitochondria are among these organelles and although they can amplify platelet activation and thrombosis, very little is known regarding their number and distribution in platelets.

Platelets circulate in blood to promote haemostasis and play pivotal roles in the prevention of bleeding. Structurally, platelets are small anucleated cells that contain a number of organelles including granules (a, dense and lysosomes), peroxisomes and mitochondria. While recognition of endothelial damage by platelets triggers fusion of the granules with the plasma membrane and the release of their contents, the repercussions of platelet activation on mitochondria distribution remains unknown.

Even though platelet activation is necessary to prevent or limit bleeding in a homeostatic state, their activation in other circumstances should be limited to avoid deleterious or pathological consequences. For example, to limit platelet activation, they are stored, prior to transfusion, at 22° C., which limits their shelf-life.

It would be highly desirable to be provided with methods and processes for limiting or even inhibiting platelet activation. It would also be desirable to be provided with methods and processes for detecting when modulation in platelet activity occurs (such as for example, platelet activation, platelet death and/or platelet apoptosis, sometimes referred to as "storage lesion") or for quantifying the extent of such platelet activation. Preferably, these methods and processes would not only be applied towards platelet activation, but could also be used in determining the presence of sterile and infectious inflammatory conditions or reactions.

BRIEF SUMMARY

The present disclosure provides methods based on the detection (and optionally the quantification) of extracellular mitochondrial components, optionally in combination with secreted phospholipase $A_2$-IIA and/or an auto-antibody, as well as their degradation products for the diagnosis, treatment, prevention and/or alleviation of symptoms associated with an inflammatory reaction or condition.

According to a first aspect, the present disclosure provides a method for assessing the presence of an inflammatory mediator in a biological sample. Broadly, the method comprises a) obtaining the biological sample susceptible of having extracellular submicrometer-sized biological components; b) substantially enriching extracellular submicrometer-sized components from the biological sample to obtain an enriched mixture; c) determining, in the enriched mixture, the level of at least one of a free mitochondria, a mitochondria microparticle, a degradation product of the free mitochondria and/or a degradation product of the mitochondria microparticle to obtain a test level; d) comparing the test level with a control level, wherein the control level is associated with the absence of the inflammatory mediator; and e) characterizing the biological sample based on the comparison. The biological sample is characterized as having the inflammatory mediator if the test level is determined to be higher than the control level. The biological sample is characterized as lacking the inflammatory mediator if the test level is determined to be equal to or lower than the control level. In an embodiment, step b) further comprises substantially removing nucleated and/or non-nucleated cells from the biological sample for obtaining the enriched mixture. In another embodiment, step c) further comprises determining the presence or absence of the at least one of the free mitochondria, the mitochondria microparticle, the degradation product of the free mitochondria and/or the degradation product of the mitochondria microparticle and, if the at least one of the free mitochondria, the mitochondria microparticle, the degradation product of the free mitochondria and/or the degradation product of the mitochondria microparticle is determined to be present, determining the level of the at least one of the free mitochondria, the mitochondria microparticle, the degradation product of the free mitochondria and/or the degradation product of the mitochondria microparticle. In yet a further embodiment, the determination of the presence or the absence of the at least one of the free mitochondria, the mitochondria microparticle, the degradation product of the free mitochondria and/or the degradation product of the mitochondria microparticle excludes detecting mitochondrial DNA. In another embodiment, the method further comprises, after step b) and prior to step c), isolating the at least one of the free mitochondria and/or the mitochondria microparticle from the enriched mixture to provide an isolated mixture. In still another embodiment, step c) further comprises obtaining the test level in the isolated mixture. In another embodiment, step c) further comprises determining the presence or the absence of mitochondrial activity in the enriched/isolated mixture for determining the test level. In such embodiment, mitochondrial activity can be determined by measuring oxygen consumption, oxidative phosphorylation, carbon dioxide production and/or membrane potential. In a further embodiment, step c) further comprises determining the test level by flow cytometry and/or by mass spectrometry. In a further embodiment, the biological sample is derived from a labile biological product, such as, for example blood, a blood product or a labile biological product comprising a platelet. In still a further embodiment, step c) further comprises determining the presence or the absence of an association between secreted phospholipase A2 group IIA (sPLA$_2$-IIA) and the free mitochondria and/or the mitochondria microparticle. In such embodiment, step c) can further comprise determining the presence or the absence of the association by measuring the enzymatic activity of sPLA$_2$-IIA and/or by detecting the presence or the absence of an sPLA$_2$-IIA polypeptide. In yet another embodiment, the inflammatory mediator is a sterile inflammatory mediator and the biological sample is from a labile biological product (has been or intended to be administrate to a treated subject). In such embodiment, step e) can further comprise characterizing the biological sample as: susceptible of causing a sterile inflammatory reaction in a treated subject if the test level is determined to be higher than the control level; or lacking the susceptibility of causing the sterile inflammatory reaction in the treated subject if the test level is determined to be equal to or lower than the control level. In an embodiment, the sterile inflammatory reaction is at least one of a febrile non-hemolytic reaction, an anaphylactic reaction, an adverse reaction following a transfusion, a transfusion-related sepsis and transfusion related acute lung injury (TRALI). In another embodiment, the biological sample is from a subject and step e) further comprises characterizing the subject as: being afflicted by a sterile inflammatory condition if the test level is determined to be higher than the control level; or lacking the affliction to the sterile inflammatory condition if the test level is determined to be equal to or lower than the control level. In such embodiment, the sterile inflammatory condition is at least one of rheumatoid arthritis, osteoarthritis, juvenile arthritis, psoriatic arthritis, gout, idiopathic thrombocytopenia, anti-phospholipid syndrome and systemic lupus erythematosus. In another embodiment, the sterile inflammatory condition is systemic lupus erythematosus. In such embodiment, step c) further comprises determining the presence of an immune complex between (i) the free mitochondria or the mitochondria microparticle and (ii) an antibody specific for the free mitochondria or the mitochondria microparticle in the biological sample. In yet another embodiment, step c) can comprise determining the presence or absence of lysocardiolipin and/or antibody specific for cardiolipin in the biological sample. In a further embodiment, the inflammatory mediator is an infectious inflammatory mediator.

In a second aspect, the present disclosure provides a method for assessing the presence of a sterile inflammatory mediator in a labile biological product. Broadly, the method comprises a) obtaining a biological sample from the labile biological product, wherein the labile biological product is susceptible of having extracellular submicrometer-sized biological components; b) substantially enriching extracellular submicrometer-sized components from the biological sample to obtain an enriched mixture; c) determining, in the enriched mixture, the level of at least one of a free mitochondria, a mitochondria microparticle, a degradation product of the free mitochondria and/or a degradation product of the mitochondria microparticle to obtain a test level; and d) comparing the test level with a control level, wherein the control level is associated with the absence of the sterile inflammatory mediator; and e) characterizing the labile biological product as having the sterile inflammatory mediator if the test level is determined to be higher than the control level or as lacking the sterile inflammatory mediator if the test level is determined to be equal to or lower than the control level. In an embodiment, the labile biological product is a blood product, such as, for example, a blood product comprising a platelet. In another embodiment, the labile biological product has been or is intended to be administered to a treated subject and step e) further comprises characterizing the labile biological product as: susceptible of causing a sterile inflammatory reaction in the treated subject if the test level is determined to be higher than the control level; or lacking the susceptibility of causing the sterile inflammatory reaction in the treated subject if the test level is determined to be equal to or lower than the control level. In an embodiment, the sterile inflammatory reaction is at least one of a febrile non-hemolytic reaction, an anaphylactic reaction, an adverse reaction following a transfusion, a transfusion-related sepsis and transfusion related acute lung injury (TRALI). Other embodiments of the methods have been disclosed above and can be applied herein.

In a third aspect, the present disclosure provides a kit for assessing the presence of an inflammatory mediator in a biological sample. The kit comprises (i) means for enriching extracellular submicrometer-sized components from the biological sample to obtain an enriched mixture and (ii) means for determining the level of at least one of a free mitochondria, a mitochondria microparticle and/or a degradation product of the free mitochondria and/or the mitochondria microparticle in the enriched mixture. In an embodiment, the kit further comprises at least one of: means for separating the enriched mixture into at least a first fraction and a second fraction, wherein the first fraction is substantially enriched in free mitochondria and wherein the second fraction is substantially enriched in mitochondria microparticles; means for isolating free mitochondria and mitochondria microparticle from the enriched mixture; means for determining the presence or absence of an association between secreted phospholipase A2 group IIA (sPLA$_2$-IIA) and the free mitochondria and/or the mitochondria microparticle; means for specifically detecting free mitochondria; means for specifically detecting mitochondria microparticles; means for detecting degradation products of free mitochondria and/or mitochondria microparticles; and/or means for determining the presence of an immune complex between (i) the free mitochondria and the mitochondria microparticle and (ii) an antibody specific to the free mitochondria and the mitochondria microparticle. In another embodiment, the kit further comprises instructions for determining the presence or the absence of a susceptibility of the labile biological product of causing an inflammatory condition in a treated subject, wherein the biological sample is from the labile biological product intended to or having been administered in the treated subject. In still another embodiment, the kit further comprises instructions for determining the presence or the absence of an affliction by an inflammatory condition in a subject, wherein the biological sample is from the subject.

In a fourth aspect, the present disclosure provides a screening method for determining the usefulness of an agent in preventing the release of an inflammation mediator. Broadly, the screening method comprises combining the agent with a cell having an internal mitochondria to obtain first combination; placing the first combination under conditions allowing the extracellular release of the internal mitochondria in the absence of the agent to obtain a first treated combination; determining the level of an extracellular mitochondrial component in the first treated combination to obtain a test level; comparing the test level to a control level, wherein the control level is associated with the release of the inflammatory mediator; and characterizing the agent as being useful for preventing the release of the sterile inflammatory mediator when the test level is determined to be lower than the control level or as lacking the utility for preventing the release of the sterile inflammatory mediator when the test level is determined to be equal to or higher than the control level.

In a fifth aspect, the present disclosure provides a screening method for determining the usefulness of an agent in inhibiting the release of an inflammation mediator. Broadly, the screening method comprises placing a cell under conditions allowing the extracellular release of the internal mitochondria to obtain a treated cell; combining the agent with the treated cell to obtain first combination; determining the level of an extracellular mitochondrial component in the first combination to obtain a test level; comparing the test level to a control level, wherein the control level is associated with the release of an inflammatory mediator; and characterizing the agent as being useful for inhibiting the release of the sterile inflammatory mediator when the test level is determined to be lower than the control level or as lacking the utility for inhibiting the release of the sterile inflammatory mediator when the test level is determined to be equal to or higher than the control level.

In a sixth aspect, the present disclosure provides a process for isolating extracellular mitochondrial components from a blood product. Broadly, said process comprises obtaining the blood product; optionally substantially removing the cells from the blood product to obtain a cell-free mixture; and isolating extracellular mitochondrial components from the sample or the cell-free mixture (i) by selecting submicrometer-sized biological components and/or (ii) using an antibody or a lectin specific for the extracellular mitochondria components, wherein the extracellular mitochondria components comprise free mitochondria and a mitochondria microparticle. In an embodiment, the blood product comprises a platelet. In still another embodiment, the process further comprises isolating extracellular mitochondria components comprising an immune complex having (i) the free mitochondria or the mitochondria microparticle and (ii) an antibody specific to the free mitochondria or the mitochondria microparticle. In another embodiment, the antibody is an IgG antibody.

In a seventh aspect, the present disclosure provides a method for assessing the presence of a sterile inflammatory mediator in a biological sample. Broadly, the method comprises obtaining biological sample susceptible of having extracellular submicrometer-sized biological components; determining, in the biological sample, the level of at least one of a free mitochondria, a mitochondria microparticle and/or a degradation product of the free mitochondria and/or of the mitochondria microparticle to obtain a test level; and comparing the test level with a control level. The biological sample is characterized as having the sterile inflammatory mediator if the test level is determined to be higher than the control level. On the other hand, the biological sample is characterized as lacking the sterile inflammatory mediator if the test level is determined to be equal to or lower than the control level. In an embodiment, the method further comprises, prior to the determining step, substantially enriching extracellular submicrometer-sized components from the biological sample to obtain an enriched mixture and, in the determining step, determining, in the enriched mixture, the level of the at least one of free mitochondria, mitochondria microparticle and/or degradation product of the free mitochondria and/or of the mitochondria microparticle to obtain the test level. In another embodiment, the determining step further comprises substantially removing nucleated and/or anucleated cells from the biological sample for obtaining the enriched mixture. In still another embodiment, the determining step further comprises determining the presence or the absence of mitochondrial activity for determining the test level. In yet another embodiment, mitochondrial activity can be determined by measuring oxygen consumption and/or the membrane potential of the free mitochondria and/or the mitochondria microparticle. In still another embodiment, the determining step further comprises determining the test level by flow cytometry and/or by mass spectrometry. In a further embodiment, the biological sample is derived from a labile biological product, such as, for example, a labile biological product that comprises a platelet. In still a further embodiment, the determining step further comprises determining the presence or the absence of an association between secreted phospholipase $A_2$ group IIA ($sPLA_2$-IIA) and the free mitochondria and/or the mitochondria microparticle. In still a further embodiment, the determining step further comprises determining the presence or the absence of the association by measuring the enzymatic activity of $sPLA_2$-IIA and/or by detecting the presence or absence of the $sPLA_2$-IIA polypeptide. In still another embodiment, the characterizing step further comprises characterizing the biological sample as: either being susceptible of causing a sterile inflammatory reaction in a treated subject if the sterile inflammatory mediator is determined to be present in the biological sample; or lacking the susceptibility of causing the sterile inflammatory reaction in the treated subject if the biological sample is determined to be absent from the biological sample. In an embodiment, the sterile inflammatory reaction is at least one of a febrile non-hemolytic reaction, an anaphylactic reaction, an adverse reaction following a transfusion, a transfusion-related sepsis and transfusion related acute lung injury (TRALI). In yet another embodiment, wherein the biological sample is from a subject and the characterizing step further comprises characterizing the subject as: either being afflicted by a sterile inflammatory condition if the sterile inflammatory mediator is determined to be present in the biological sample; or lacking the affliction to the sterile inflammatory condition if the sterile inflammatory mediator is determined to be absent in the biological sample. In still a further embodiment, the sterile inflammatory condition is at least one of rheumatoid arthritis, osteoarthritis, juvenile arthritis, psoriatic arthritis, gout, idiopathic thrombocytopenia, anti-phospholipid syndrome and systemic lupus erythematosus.

In an eighth aspect, the present disclosure provides a kit for assessing the presence of a sterile inflammatory mediator in a biological sample. The kit comprises means for determining the level of at least one of a free mitochondria, a mitochondria microparticle and/or a degradation product of the free mitochondria and/or the mitochondria microparticle in the biological sample. In an embodiment, the kit further comprises at least one of: means for substantially removing nucleated and/or anucleated cells from the biological sample for obtaining the enriched mixture; means for separating the enriched mixture into at least a first fraction and a second fraction, wherein the first fraction is substantially enriched in free mitochondria and wherein the second fraction is substantially enriched in mitochondria microparticles; and/or means for determining the presence or absence of an association between secreted phospholipase $A_2$ group IIA ($sPLA_2$-IIA) and the free mitochondria and/or the mitochondria microparticle. In another embodiment, the kit is for determining the presence or the absence of a susceptibility of the biological sample of causing a sterile inflammatory condition in a treated subject. In another embodiment, the kit is for determining the presence or the absence of an affliction by a sterile inflammatory condition in a subject, wherein the biological sample is from the subject.

In a ninth aspect, the present disclosure provides a method for limiting the release of a sterile inflammatory mediator from a cell. Broadly, the method comprises contacting an agent capable of limiting the extracellular release of an intracellular mitochondria with the cell under conditions for limiting the release of the sterile inflammatory mediator. Alternatively, the method can broadly comprise contacting a secreted phospholipase $A_2$ group IIA (sPLA$_2$-IIA) antagonist with the cell under conditions for limiting the release of the sterile inflammatory mediator. In an embodiment, the cell is in vitro. In yet a further embodiment, the method is for limiting a sterile inflammatory reaction during the storage of the cell (e.g., a platelet for example). In still another embodiment, the sterile inflammatory reaction is the activation of the platelet. In another embodiment, the cell is in vivo in a subject in need thereof. In such embodiment, the method can be for preventing, treating and/or alleviating the symptoms associated with a sterile inflammatory condition in the subject. In an embodiment, the sterile inflammatory condition is associated with the degradation of a platelet.

In a tenth aspect, the present disclosure provides an agent capable of limiting the extracellular release of an intracellular mitochondria and/or a secreted phospholipase $A_2$ group IIA (sPLA$_2$-IIA) antagonist for limiting the release of a sterile inflammatory mediator from a cell. In an embodiment, the cell is in vitro, and in a further embodiment, the agent or antagonist is for limiting a sterile inflammatory reaction during the storage of the cell (e.g., a platelet, for example). In still a further embodiment, the sterile inflammatory reaction is the activation of the platelet. In an embodiment, the cell is in vivo in a subject and, in a further embodiment, the agent or antagonist is for preventing, treating and/or alleviating the symptoms associated with a sterile inflammatory condition in the subject. In a further embodiment, the sterile inflammatory condition is associated with the degradation of a platelet.

In an eleventh aspect, the present disclosure provides an additive for a storage solution of a labile biological product. The additive comprises the agent or antagonist described herein.

In a twelfth aspect, the present disclosure provides a pharmaceutical composition comprising the agent or antagonist described herein and a pharmaceutically acceptable excipient.

In a thirteenth aspect, the present disclosure provides a screening method for determining the usefulness of an agent in preventing the release of a sterile inflammation mediator. Broadly, the screening method comprises combining the agent with a cell having an internal mitochondria to obtain first combination; placing the first combination under conditions allowing the extracellular release of the internal mitochondria in the absence of the agent to obtain a treated first combination; determining the level of an extracellular mitochondrial component in the treated first combination to obtain a test level; and comparing the test level to a control level. The agent is then characterized as either being useful for preventing the release of the sterile inflammatory mediator when the test level is determined to be lower than the control level or as lacking the utility for preventing the release of the sterile inflammatory mediator when the test level is determined to be equal to or higher than the control level.

In a fourteenth aspect, the present disclosure provides a screening method for determining the usefulness of an agent in inhibiting the release of a sterile inflammation mediator. Broadly, the screening method comprises placing a cell under conditions allowing the extracellular release of the internal mitochondria to obtain a treated cell; combining the agent with the treated cell to obtain first combination; determining the level of an extracellular mitochondrial component in the first combination to obtain a test level; and comparing the test level to a control level. The agent is characterized as being useful for inhibiting the release of the sterile inflammatory mediator when the test level is determined to be lower than the control level or as lacking the utility for inhibiting the release of the sterile inflammatory mediator when the test level is determined to be equal to or higher than the control level.

In a fifteenth aspect, the present disclosure provides a process for isolating extracellular mitochondrial components from a sample comprising a plurality of platelets. Broadly, the process comprises obtaining the sample; optionally substantially removing the plurality of platelets from the sample to obtain a platelet-free mixture; and isolating extracellular mitochondrial components from the sample or the platelet-free mixture using (i) by selecting components having a relative size of less than about 1 µm and/or (ii) an antibody or a lectin specific for the mitochondrial components. In yet another embodiment, the extracellular components comprises a free mitochondria and the process further comprises isolating the free mitochondria using an antibody or a lectin specific for the free mitochondria. In still another aspect, the extracellular components comprises a mitochondria microparticle and the process further comprises isolating the free mitochondria using an antibody or a lectin specific for the mitochondria microparticle.

BRIEF DESCRIPTION OF THE DRAWINGS

Having thus generally described the nature of the invention, reference will now be made to the accompanying drawings, showing by way of illustration, a preferred embodiment thereof, and in which:

FIG. 10) and mtDNA quantification. (C) TEM imaging of (left) a freeMito and (right) a mitoMP from fresh RA SF. (D) $O_2$ consumption is observed in platelet-free plasma (PFP) obtained at the indicated time intervals from platelet storage bags. (E) Isolation of freeMitos (FIG. 10) in PFP along with mtDNA quantification reveals an abundance of freeMito at day 5 (n=6; data are mean±SEM, *P<0.05 vs. day 0, paired t test). (F) High-sensitivity flow cytometry (hs-FCM) analysis of resting platelets (upper panel, top right quadrant) and thrombin-activated platelets, which show 3 additional distinct populations of particles, ie, freeMitos (bottom panel, top left quadrant, blue), mitoMPs (bottom panel, top right quadrant, pink), and mitochondria-free MPs (bottom panel, bottom right quadrant, red). Bottom left quadrant of both upper and lower panels represents background noise (gray). FSC-PMT and SSC dot plots of platelets (first right panel) and 3 populations of microparticles: freeMitos (second right panel), mitoMPs (third right panel), and MPs (fourth right panel). The relative diameters are presented according to size-defined microsphere calibrations. (G) TEM imaging of PFP collected on day 5 confirming the presence of (left) freeMitos and (right) mitoMPs. (H) Mitochondrial membrane potential is detected in freeMitos and mitoMPs collected from PFP, as measured by a JC-1 assay using hs-FCM (red to green ratio) (n=5; data are mean±SEM). (I) Extracellular mitochondria (as detected by mtDNA quantification) are found at higher concentration in PFP of platelet storage bags that have caused adverse transfusion reaction to the recipient (no adverse reaction group [● n=61] vs adverse reaction group [■ n=74] matched in terms of storage duration; data are mean±SEM, ***P<0.001, t test). Adverse reactions measured include mainly febrile nonhemolytic reactions, skin manifestations such as itching or skin rash, and cardiovascular events such as hypotension or tachycardia.

FIG. 9. Characterization of platelet supernatants. (A) Platelets were counted in platelet preparations (before) and following centrifugation (after) by microscopy to detect residual platelet contamination in the supernatant. No detectable platelet remains in supernatants with the centrifugation protocol used. (B) No respiratory activity was detected in Tyrode's buffer following the addition of intact platelets (≤80 000/mL) indicating the detection limit of the approach. For comparison, the supernatant obtained after isolating activated platelets, which contains extracellular mitochondria, displays significant respiration.

FIG. 10. Magnetic purification of freeMitos. The platelet supernatant, which contains freeMitos, mitoMPs and MPs, is incubated with anti-TOM22 microbeads, and freeMitos are then isolated using a magnetic field. Magnetic field removal allows the elution of freeMitos from the column, which are then used for various purposes.

DETAILED DESCRIPTION

Figure 1C:
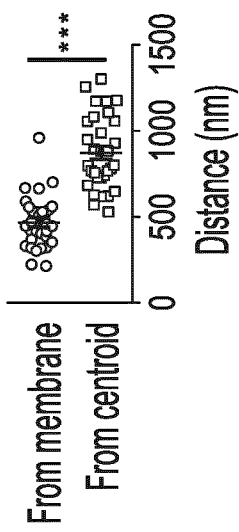
FIG. 1. Mitochondrial distribution within resting platelets. Mitochondria (black arrows) in resting platelets examined by (A) TEM and (B) confocal scanning laser microscopy (CSLM). (C) Mitochondria are located proximally to the platelet plasma membrane (n=31; data represent the mean±standard error of the mean [SEM], ***$P<0.0001$, t test).

In accordance with the present disclosure, there is provided methods based on the detection (and optionally the quantification) of extracellular mitochondrial components and their degradation products, optionally in combination with the secreted phospholipase A$_2$ group IIA (sPLA$_2$-IIA) and/or specific autoantibodies, for the diagnosis, treatment, prevention and/or alleviation of symptoms associated with an inflammatory reactions and conditions. The inflammatory mediator can be sterile or infection and consequently, the inflammatory conditions/reactions can be sterile or infectious. As shown herein extracellular mitochondrial components are released during an in vitro or an in vivo sterile inflammatory reaction or condition and contribute to the onset, maintenance or severity of the sterile inflammatory reaction. The association of these extracellular mitochondrial components with sPLA$_2$-IIA and/or autoantibodies further exacerbates the effects of the extracellular mitochondrial components on the sterile inflammatory reaction as it accelerates the degradation of the extracellular mitochondrial components. The results presented herein also suggest that the association of these extracellular mitochondrial components with sPLA$_2$-IIA would exacerbate the effects of the extracellular mitochondrial components in an infectious inflammatory reaction, as it would also accelerate the degradation of the extracellular mitochondrial components.

A model sterile inflammatory reaction was used to understand the mechanism underlying the activation of platelets. As shown herein, upon activation, platelets unexpectedly release their mitochondria in the extracellular milieu, which results in an amplification of inflammation. As also shown herein, mitochondria localize preferentially in the vicinity of the platelet cytoplasmic membrane, and, once released from activated platelets, are capable of respiration. These mitochondria are either contained within microparticles (small vesicles shed from the cytoplasmic membrane, herein referred to as mitochondria microparticles or mitoMPs) or free in the extracellular milieu (herein referred to as free mitochondria or freemitos). Extracellular mitochondria are shown to be present in platelet concentrates used for transfusion and in multiple disorders where platelets are active. The mitochondrion was identified as an endogenous substrate of the bactericidal secreted phospholipase A$_2$ group IIA (sPLA$_2$-IIA). Hydrolysis of the mitochondrial membrane by sPLA$_2$-IIA yields mediators that promote leukocyte activation, triggering inflammation in vivo. Mitochondria are known to be a source of unmethylated CpG DNA sequences and N-formylated peptides promoting inflammation in the absence of pathogens. However their origin in such sterile contexts was obscure. Furthermore, while sPLA$_2$-IIA has long been observed to be present in diverse inflammatory fluids, its endogenous substrate is still debated. The findings presented herewith identify platelets as a major source of extracellular mitochondria that enhance mediator production and inflammation, relevant to blood transfusion and sterile inflammatory responses.

Assessment of the Presence of Inflammatory Mediators in Biological Samples

As it will be described below, it was surprisingly found that one source of inflammatory mediators (and in an embodiment of sterile inflammatory mediators) in biological samples is extracellular mitochondrial components (e.g., free mitochondria and/or mitochondria microparticle(s)) as well as their degradation products. In some embodiments, these extracellular mitochondrial components are released from platelets. Some of the extracellular mitochondrial components are capable of releasing potent inflammatory mediators (such as reactive oxygen species, N-formylated peptides and/or DNA having unmethylated CpG motifs). What is also shown herein is that the association of the extracellular mitochondrial components with the polypeptide secreted phospholipase $A_2$ group IIA (sPLA$_2$-IIA) triggers the release of additional potent inflammatory substances, such as, for example, lysophospholipids and/or fatty acids which further contributes to the maintenance or onset of sterile inflammatory processes.

The present disclosure thus provides methods for assessing the presence of an inflammatory mediator in a biological sample based on the determination of the presence or absence of extracellular mitochondrial components such as free mitochondria and mitochondria microparticle(s) as well as their degradation products. The methods described herein can be used to determine the presence of sterile or infectious inflammatory conditions. As used herein, the term "extracellular mitochondrial component" refers to a subcellular entity which is no longer located inside a cell (e.g., nucleated or anucleated cell) and which comprises at least a mitochondria, optionally in combination with a non-mitochondrial cellular membrane (e.g., the cytoplasmic membrane of the cell which released the component for example). In some embodiments, these extracellular mitochondrial components, when functional, are capable of mediating physiological respiration. In the context of the present disclosure, "extracellular mitochondrial components" refer to free mitochondria, mitochondria microparticles as well as related immune complexes. The term "free mitochondria" refers to an extracellular mitochondrial component which is not associated (e.g., not at least partially or entirely coated) with a non-mitochondrial cellular membrane. For example, free mitochondria usually expose the polypeptide TOM22 on their outermost mitochondrial surface and can be recognized by (or even be purified with) an antibody or a lectin specific for TOM22. The term "mitochondria microparticle" refers to at least one mitochondria which is associated (e.g., at least partially or completely covered with) with a non-mitochondrial membrane. For example, mitochondria microparticles usually do not expose the mitochondrial-specific polypeptide TOM22 on their most external surface and cannot be recognized by an antibody or a lectin specific for TOM22. However, mitochondria microparticles can possess cytoplasmic membrane-proteins exposed on their outermost surface and can be recognized by an antibody specific for such cytoplasmic membrane proteins. For example, when mitochondria microparticles are derived from platelets, they can possess the cytoplasmic membrane-protein CD41 on their outermost surface and can be recognized by (or even be purified with) an anti-CD41 specific antibody or lectin. The term "immune complex" (also referred to as IC) refers to a non-covalent complex formed between a free mitochondria or a mitochondria microparticle and a corresponding specific auto-antibody (such as, for example, a corresponding specific IgG auto-antibody). Still in the context of the present disclosure, the term "extracellular mitochondrial component" specifically excludes any type of microparticles which do not contain a mitochondria. Also, in the context of the present disclosure, the expression "degradation products of an extracellular mitochondrial component" refers to any substance which is released during the degradation of a free mitochondria or a mitochondria microparticle. Such degradation products include, without limiting, lipids (such as phospholipids, especially cardiolipin and/or lysocardiolipin), antibodies specific for such lipids (such as anti-cardiolipin antibodies), DNA fragments, reactive oxygen species (ROS), peptides, carbohydrates moieties, metabolites of oxidative phosphorylation, etc. In an embodiment, the degradation product is specific to the mitochondrial extracellular components. In an embodiment, the lipids are indirectly measured by the presence of auto-antibodies specific for such lipids (anti-cardiolipin antibodies for example).

The methods are designed to assess if a sterile or an infectious inflammatory mediator is present in a biological sample by determining the presence, the absence or the level of extracellular mitochondrial components in a biological sample. In the context of the present disclosure, the term "sterile inflammatory mediator" refers to a substance capable of eliciting and/or contributing to a sterile inflammatory reaction or condition. As described herein, free mitochondria, mitochondria microparticles as well as their degradation products (including metabolites of oxidative phosphorylation) are considered sterile inflammatory mediators. Still in the context of the present disclosure, the term "infectious inflammatory mediator" refers to a substance capable of eliciting and/or contributing to an infectious inflammatory reaction or condition. As described herein, free mitochondria, mitochondria microparticles as well as their degradation products are considered infectious inflammatory mediators. However, in the context of the present disclosure, microparticles which do not possess a mitochondria are not considered sterile nor infectious inflammatory mediators.

The first step of the method for detecting the presence of an inflammatory disorder is to obtain or be provided with a biological sample. Any types of biological samples which are or were in contract with at least one cell in vivo (e.g., a nucleated or an anucleated cell) can be submitted to the method. Exemplary biological samples can be derived from a labile biological product that can be stored (e.g., blood, blood fraction(s) or components (such as serum or plasma)), tissues, lymphatic fluid, cerebrospinal fluid, synovial fluid, bronchoalveolar lavage, urine, semen, fluid from reproductive tract, and saliva. In an embodiment, biological samples can also include non-biological components, such as buffers and the like. For example, when a biological product needs to be stored prior to its subsequent use (e.g., transplantation or transfusion), the biological sample can be a mixture of cells, tissues and/or a biological fluid admixed in a storage or transportation medium (for example a platelet storage solution, a transportation solution, a transplantation solution, a grafting solution, etc.). Preferably, the biological sample submitted to the method described herein is susceptible of having or containing submicrometer-sized biological components (e.g., components having a relative size lower than 1 µm). Such biological samples can be, for example, a blood product (for example a stored blood product), a sample obtained from a biological product suspected to have caused or capable of causing a sterile or an infectious inflammatory reaction/condition when introduced into a subject, a sample obtained from a subject afflicted by or suspected of being afflicted by a sterile or an infectious inflammatory reaction/ condition. In still another embodiment, the biological sample can be derived from a platelet, e.g., has been or is in contact with at least one platelet (in vitro or in vivo). The person of ordinary skill in the art will recognize that the methods can be applied to various types of biological samples from various subjects, preferably those capable of generating a platelet, such as mammals and, in still another embodiment, humans.

Once the biological sample has been obtained or provided, it must be determined if extracellular mitochondrial components are present, and in some embodiments, the level of such extracellular mitochondrial components. In the context of the present disclosure, it is understood that in any methods used for detecting and optionally quantifying extracellular mitochondrial components, care should be taken to detect mitochondrial components in the extracellular environment. In some embodiments, the methods described herein include a step of substantially removing sources of intracellular mitochondria (including intracellular mitochondrial DNA) from the enriched mixture (such as for example removing nucleated and anucleated cells from the mixture) prior to undertaking the measurement.

The person of ordinary skill in the art will be aware that various methods are known for determining the presence and optionally of the quantity extracellular mitochondrial components. For example, by using flow cytometry, it is possible to determine the presence, and in some embodiments, the level of extracellular mitochondrial components based on their relative size and, in an embodiment, the presence or absence of a specific marker (e.g., TOM22 for example) or a specific combination of markers. In some embodiments of the methods in which the extracellular mitochondrial component forms an immune complex (herein referred as IC) with an auto-antibody (such as an auto-IgG antibody), it is also possible to use flow cytometry to detect such ICs (based for example on their size or their affinity for an anti-autoantibody antibody for example).

In another embodiment, it is possible to use mass spectrometry or thin layer chromatography, it is possible to determine the presence, and in some embodiments, the level of extracellular mitochondrial components based on the detection of mitochondrial-specific phospholipids (e.g., the native cardiolipin (present on the surface of mitochondria) or the cleaved lysophospholipin). Such determinations can be made, for example, by using antibodies specific for the mitochondrial lipids (native or cleaved form).

Alternative processes are known to those skilled in the art to determine the presence and/or level of such mitochondrial components. For example, mitochondrial activity (e.g., oxygen consumption, generation of reactive oxygen species, carbon dioxide generation, generation of oxidative phosphorylation (either directly or via the determination of oxidative phosphorylation metabolites such as succinate, fumarate and the like), mitochondrial membrane potential (using the JC-1 dye for example)) can be assayed to determine if mitochondrial components are present in the enriched mixture. The assays using the determination of mitochondrial activity are especially useful in determining the functionality of the mitochondrial components which may be present in the enriched mixture.

In another example, morphological assays (e.g., microscopy, including immunofluorescence, confocal microscopy and electron microscopy, flow cytometry) can be used to study mitochondrial structure and ultimately determine the presence or absence as well as the level of extracellular mitochondrial components as well as immune complexes comprising such extracellular mitochondrial components. Assays concerning the morphology of the mitochondrial components can also be indicative of the functionality of the mitochondria in the biological sample.

In still another example, antibody-based assays (e.g., immunoblotting, flow cytometry, immunoassay, antibody-based purification assays) can be used to determine the presence or absence of mitochondrial components (such as the presence of specific mitochondrial surface proteins, the presence or absence of specific platelet surface proteins and/or the presence or absence of specific auto-antibodies).

In yet another example, genomic-based assays (e.g., nucleotide amplification assays, including PCR, RT-PCR and qPCR, nucleotide probe-based assays, sequencing, etc.) can be used to determine the presence or absence of mitochondrial components in the enriched mixture. The nucleic acid amplification step is particularly useful for providing a semi-quantitative or a quantitative measure of the number of mitochondrial components in the enriched mixture. Various nucleic acid primers and probes (as well as combinations thereof) can be used. Examples of such nucleic acid primers and probes include, but are not limited to, the nucleic acid molecules having the sequence of SEQ ID NO: 1, SEQ ID NO: 2, SEQ ID NO: 3, SEQ ID NO: 4, SEQ ID NO: 5 and/or SEQ ID NO: 6. The nucleic acid molecules can be provided in the form of primer pairs (for example the pair of oligonucleotides defined as SEQ ID NO: 1 and 2 or the pair of oligonucleotides defined as SEQ ID NO: 4 and 5) or in the form of a provide (for example the probe defined as SEQ ID NO: 3 or SEQ ID NO: 6). For example, mitochondrial DNA can be amplified using a first primer pair (for example using the primer set having the nucleotide sequence set forth as SEQ ID NO: 1 and 2) and, optionally, the mitochondrial nature of such amplified DNA can be confirmed using a probe (for example using the probe having the nucleotide sequence as set forth in SEQ ID NO: 3). In yet another example, mitochondrial DNA can be amplified using a first primer pair (for example using the primer set having the nucleotide sequence set forth as SEQ ID NO: 4 and 5) and, optionally, the mitochondrial nature of such amplified DNA can be confirmed using a probe (for example using the probe having the nucleotide sequence as set forth in SEQ ID NO: 6). In some embodiments, the primers and/or the probe can be designed to specifically amplify and/or recognize mitochondrial DNA from a free mitochondria or, alternatively, from a mitochondrial microparticle. In the context of the present disclosure, it is understood that if mitochondrial DNA is used for detecting and optionally quantifying extracellular mitochondrial components, care should be taken to substantially remove sources of intracellular mitochondrial DNA from the enriched mixture (such as for example removing nucleated and anucleated cells from the mixture) prior to undertaking the measurement.

More than one technique can be combined to achieve the determination of the presence and/or the level of extracellular mitochondrial components. For example, in an embodiment, the method can include the purification of a fraction of the enriched mixture substantially comprising free mitochondria (for example using the anti-TOM22 antibody), followed by a subsequent nucleic acid amplification step to quantify the number of free mitochondria in the fraction (and ultimately in the enriched mixture). As used herein, the term "substantially comprising free mitochondria" refers to a fraction of the biological sample in which the ratio between the number of free mitochondria and the number of mitochondria microparticles is higher than the same ratio in the biological sample.

In an embodiment, the method comprises a dual determining step for extracellular mitochondrial components. First, it is determined if extracellular mitochondrial components are present or absent from the biological sample. In some specific embodiments, determining the presence or the absence of mitochondrial DNA is not used in this first determining step. For example, the presence or the absence of the extracellular mitochondrial components can be made using antibodies or lectins specific to extracellular mitochondrial components. Second, if it is determined that extracellular mitochondrial components are present in the biological sample, the level of such extracellular mitochondrial components are determined. In some specific embodiments, determining the level of extracellular mitochondrial components can be made using quantification of mitochondrial DNA as well as antibodies or lectins specific for extracellular mitochondrial components.

In yet another embodiment, the present methods can include a step of isolating extracellular mitochondrial components from the biological sample to obtain an isolated mixture. In the context of the present disclosure, the mixture is considered isolated if components which are not extracellular mitochondrial components are removed from the enriched mixture. In such embodiment, the determining step is conducted in the isolated mixture.

Alternatively or complementarily, the method includes the purification of a fraction of the enriched mixture substantially comprising mitochondria microparticles (for example using an anti-CD41 antibody) followed by subsequent nucleic acid amplification step to quantify the number of mitochondria microparticles in the fraction (and ultimately in the enriched mixture). As used herein, the term "substantially comprising mitochondria microparticles" refers to a fraction of the biological sample in which the ratio between the number of mitochondria microparticles and the number of free mitochondria is higher than the same ratio in the biological sample.

In some embodiments of the method described herein, it is necessary to discriminate the location of the mitochondrial components, e.g., intracellular vs. extracellular, to assess the presence of inflammatory mediators. As cells and non-mitochondrial extracellular debris are mostly in the micrometer range, the substantial removal of micrometer-sized components (or even components having higher relative sizes) from the biological sample can allow the discrimination between intracellular and extracellular mitochondria. As used herein, the term "substantially removing/depleting micrometer-sized components" refers to increasing the ratio between components having a relative size in the submicrometer range (e.g., lower than about 1 µm) vs. components having a relative size in the micrometer range (e.g., higher than about 1 µm) of the enriched mixture when compared to the biological sample. Alternatively, a substantial enrichment in submicrometer-sized components from the biological sample can also achieve this discrimination between intracellular and extracellular mitochondrial components. As used herein, the term "substantially enriching submicrometer-sized components" refers to increasing the ratio between components having a relative size in the submicrometer range (e.g., lower than about 1 µm) vs. components having a relative size in the micrometer range (e.g., higher than about 1 µm) of the enriched mixture when compared to the biological sample (obtained or provided).

The person of ordinary skill in the art will recognize that various processes can be used to achieve such depletion and/or enrichment. Such processes include, but are not limited to, centrifugation, filtration, cell-sorting and/or cellular lysis. For example, the enrichment step can comprise the substantial removal of cells (having a nucleus or not) and/or micrometer-sized cellular debris from the biological sample. As used herein, the "substantial removal of cells" refers to a reduction in at least 50%, at least 60%, at least 70%, at least 80%, at least 90%, at least 95% or at least 99% in the cellular density of the enriched mixture when compared to the cellular density of the biological sample.

Once the presence and/or the level of the mitochondrial component has been determined in the biological sample or in the enriched mixture to provide a test level, such test level must be compared to a control level. As used herein, the term "control level" refers to the absence of extracellular mitochondrial components or to a level of the extracellular mitochondrial component either not associated with a sterile or an infectious inflammatory reaction, not associated with a sterile or an infectious inflammatory condition, observed in non-pathological conditions, or obtained in the absence of a sterile or an infectious inflammatory mediator.

Once the comparison has been made, the biological sample can be characterized. As indicated above, the presence (and the level) of extracellular mitochondrial components is correlated with the presence of the inflammatory mediator (and ultimately of the ability of causing an inflammatory reaction or susceptibility to an inflammatory condition). As such, if it is determined that the biological sample/enriched mixture has free mitochondria and/or mitochondria microparticle(s) or that the level measured in the biological sample is higher than a control level, then it is assessed that the biological sample comprises the inflammatory mediator. However, if it is determined that the biological sample/enriched mixture does not have free mitochondria and/or mitochondria microparticle(s) or that the level measured in the biological sample/enriched mixture is equal to or lower than a control, then it is assessed that the biological sample does not comprise (e.g., lacks) the inflammatory mediator.

In some embodiments, it may be useful not only to determine the presence and/or level of the extracellular mitochondrial components, but also to assess whether or not those extracellular mitochondrial components are physically associated with the secreted phospholipase A2 group IIA (sPLA$_2$-IIA) polypeptide. As shown herein, the physical association between sPLA$_2$-IIA and the membrane of the extracellular mitochondrial components triggers the release of additional inflammatory substances (such as, for example, lysophospholipids and fatty acids). The physical association between sPLA$_2$-IIA and the membrane of the extracellular mitochondrial components further contributes to the onset or the maintenance of a sterile inflammatory reaction/condition (in vitro as well as in vivo). Such association can be determined enzymatically, for example, by measuring the consumption of sPLA$_2$-IIA substrate(s) (e.g., mitochondrial membrane integrity) and/or the production of sPLA$_2$-IIA products (e.g., lysophospholipids and fatty acids for example). Such association can also be measured at the polypeptide level using, for example, an anti-sPLA$_2$-IIA antibody coupled to a detection technique (e.g., immunoblotting, flow cytometry, immunofluorescence, etc.).

In other embodiments, it may be useful not only to determine the presence and/or level of the extracellular mitochondrial components but also to assess whether or not these extracellular mitochondrial components are physically associated with an auto-antibody, such as an IgG auto-antibody. Such embodiments are especially useful when the method is used to determine if a subject is at risk or experiences an inflammatory reaction/condition, such as a sterile inflammatory reaction/condition. The physical association between auto-antibodies and the membrane of the extracellular mitochondrial components is indicative of the onset and maintenance of an inflammatory condition (such as a sterile inflammatory condition, for example, systemic lupus erythematosus). Such association can also be measured at the polypeptide level using, for example, an antiauto-antibody (such as an anti-IgG) coupled to a detection technique (e.g., immunoblotting, flow cytometry, immunofluorescence, etc.).

The methods described herein can be used to assess if the biological sample (or the biological product from which the sample is obtained) is susceptible of causing an inflammatory reaction in a treated subject (which has received or is susceptible of receiving the biological sample or the biological product). In an embodiment, the inflammatory reaction is a sterile inflammatory reaction. In still another embodiment, the sterile inflammatory reaction is caused by the extracellular release of mitochondrial components by platelets. Sterile inflammatory reactions which may afflict the treated subject include, but are not limited to, a febrile non-hemolytic reaction, an anaphylactic reaction, a transfusion-related adverse event, a transfusion-related sepsis, transfusion related acute lung injury (TRALI) and/or death. If the presence of free mitochondria and/or mitochondria microparticles (both optionally in combination with $sPLA_2$-IIA and/or an auto-antibody via their membrane) is detected, or in an embodiment, is quantified to be higher than a control level, the biological sample (or the biological product associated thereto) is considered susceptible of causing a sterile inflammatory reaction in a treated subject. However, if the extracellular mitochondrial component is absent, cannot be detected, or in an embodiment, is quantified to be equal to or lower than a control level, the biological sample (or the biological product associated thereto) is considered not to be susceptible (e.g., lacking the susceptibility) of causing an inflammatory reaction in a treated subject.

In an embodiment, the inflammatory reaction is an infectious inflammatory reaction. In still another embodiment, the infectious inflammatory reaction is caused by the extracellular release of mitochondrial components by platelets. Infectious inflammatory reactions which may afflict the treated subject include, but are not limited to, a viral infection, a bacterial infection, a yeast infection, a mold infection and/or a prion infection. If the presence of free mitochondria and/or mitochondria microparticles (both optionally in combination with $sPLA_2$-IIA and/or an auto-antibody via their membrane) is detected, or in an embodiment, is quantified to be higher than a control level, the biological sample (or the biological product associated thereto) is considered susceptible of causing an infectious inflammatory reaction in a treated subject. However, if the extracellular mitochondrial component is absent, cannot be detected, or in an embodiment, is quantified to be equal to or lower than a control level, the biological sample (or the biological product associated thereto) is considered not to be susceptible (e.g., lacking the susceptibility) of causing an infectious inflammatory reaction in a treated subject.

The methods described herein can also be used to limit complications associated with the administration or transfusion of a biological product (such as a blood product). In such embodiments, the methods can also comprise administering or transfusing a biological product (such as a blood product) only when it was determined that such biological product (or a sample obtained therefrom) does not contain extracellular mitochondrial components or contains a level of extracellular mitochondrial components which is not associated with the trigger or maintenance of a sterile or an infectious inflammatory reaction. The methods can also comprise avoiding administering or transfusing a biological product (such as a blood product) when it was determined that such biological product (or a sample obtained therefrom) does contain extracellular mitochondrial components or has a level of extracellular mitochondrial components which is associated with the trigger or maintenance of a sterile or an infectious inflammatory reaction. This embodiment is especially useful in the administration of labile biological products such as the transfusion of blood products (for example, (stored) platelets).

The methods described herein can also be used to determine the effects of the purification and/or storage conditions on the quality of a biological product. For example, when two different purification processes are conducted from the same biological product to obtain purified and storable biological product preparations, the methods described herein can be used to determine if these different purifications induce the release of a sterile or an infectious inflammatory mediator. The methods can also be used to determine which, if any, of the two purification processes induce less of a release of the sterile/infectious inflammatory mediator and ultimately select the purification process which is less susceptible of triggering the release of extracellular mitochondrial components.

The methods described herein can be performed once or at various intervals. In the latter case, a plurality of determinations are made as a function of time. These determinations can be used to monitor the quality of the biological product during storage for example.

The determination of the presence and/or level of free mitochondria and/or mitochondria microparticles (both optionally in combination with between $sPLA_2$-IIA via their membrane) can be used to assess if a subject (from which the biological sample has been obtained) is susceptible of being afflicted with an inflammatory condition. In an embodiment, the inflammatory condition is a sterile inflammatory condition. The methods are particularly useful in sterile inflammatory conditions associated with the degradation of platelets. Sterile inflammatory conditions which may afflict the subject include, but are not limited to, any conditions in which platelets are involved. Such conditions include, but are not limited to, rheumatoid arthritis, juvenile arthritis, psoriatic arthritis, gout, idiopathic thrombocytopenia and systemic lupus erythematosus. In an embodiment, these conditions can also include osteoarthritis, endometriosis, anti-phospholipid syndrome as well as cardiovascular disease. If the extracellular mitochondrial components (optionally in combination with $sPLA_2$-IIA and/or an auto-antibody via their membrane) are detected, or in an embodiment, are quantified to be higher than a control level, the subject is considered being afflicted by the sterile inflammatory condition. However, if the extracellular mitochondrial components (optionally in combination with $sPLA_2$-IIA and/or an auto-antibody via their membrane) are absent, cannot be detected, or in an embodiment, are quantified to be equal to or lower than a control level, the subject is considered not to be afflicted (e.g., lacking the affliction) by the sterile inflammatory condition.

In another embodiment, the inflammatory condition is an infectious inflammatory condition. Infectious inflammatory conditions which may afflict the subject include, but are not limited to, any conditions in which platelets are involved. Such conditions include, but are not limited to, a viral infection, a bacterial infection, a yeast infection, a mold infection and/or a prion infection. If the extracellular mitochondrial components (optionally in combination with $sPLA_2$-IIA and/or an auto-antibody via their membrane) are detected, or in an embodiment, are quantified to be higher than a control level, the subject is considered being afflicted by the infectious inflammatory condition. However, if the extracellular mitochondrial components (optionally in combination with $sPLA_2$-IIA and/or an auto-antibody via their membrane) are absent, cannot be detected, or in an embodiment, are quantified to be equal to or lower than a control level, the subject is considered not to be afflicted (e.g., lacking the affliction) by the infectious inflammatory condition.

The methods described herein can be used not only to identify subjects susceptible of being afflicted with an inflammatory condition, but also to modify the therapeutic regimen of such subjects to alleviate the symptoms of the inflammatory condition. For example, the methods can further comprise administering a therapeutic regimen for alleviating the symptoms of the sterile or infectious inflammatory condition only to subjects in which a biological sample/enriched mixture has been determined to contain extracellular mitochondrial components or a level of extracellular mitochondrial components which is associated with the trigger or maintenance of a sterile or an infectious inflammatory condition. Alternatively, the method can also comprise avoiding administering a therapeutic regimen for alleviating the symptoms of the sterile inflammatory condition in subjects in which a biological sample/enriched mixture has been determined not to contain extracellular mitochondrial components or a level of extracellular mitochondrial components which is not associated with the trigger or maintenance of a sterile or an infectious inflammatory condition.

The methods described herein can be used not only to identify subjects susceptible of being afflicted with an inflammatory condition, but also to stratify them based on the presence, absence or level of extracellular mitochondrial components. For example, the methods described herein can be used to determine targeted treatment, inclusion or exclusion in a specific clinical trial, in a specific treatment arm, etc. In such embodiments, the method for stratifying a group of individuals comprises determining, in a sample from each individual, the presence, absence and/or level of extracellular mitochondrial components. Once such determination has been made, then the group of individuals is divided into subgroups of individuals having a common property with respect to their extracellular mitochondrial components (e.g., presence of extracellular mitochondrial components, absence of extracellular mitochondrial components, high level of extracellular mitochondrial components, intermediate level of extracellular mitochondrial components, low level of extracellular mitochondrial components, presence of metabolically active extracellular mitochondrial components, absence of metabolically active extracellular mitochondrial components, level of metabolic activity of extracellular mitochondrial components, etc.). In some embodiments, one of the resulting subgroups could contain individuals having a skewed distribution towards individuals diagnosed, predisposed or afflicted with the inflammatory condition when compared to control individuals. As a result of this method, one, some or all of the subgroups of individuals created can be included or excluded from a pre-clinical or a clinical trial, from a specific treatment arm, etc.

The methods described herein can be performed once or at various intervals. In the latter case, a plurality of determinations are made as a function of time. These determinations can be used to monitor disease progression in a subject and/or the usefulness of the therapeutic regimen in the subject.

In order to perform the methods described herein, the present disclosure also provides a kit for assessing the presence of an inflammatory mediator in a biological sample. In an embodiment, the kit can be used for determining the presence or the absence of a susceptibility of a biological product (from which the biological sample has been obtained or derived) of causing an inflammatory reaction in a treated subject. In another embodiment, the kit can be used for determining the presence or the absence of an affliction by an inflammatory condition in a subject (from which the biological sample has been obtained or derived).

In its simplest embodiment, the kit comprises means for determining the presence or absence of a free mitochondria and/or a mitochondria microparticle in an enriched mixture obtained by substantially enriching submicron components from the biological sample. Such means include, but are not limited to antibodies (such as for example anti-TOM22, anti-CD41 antibodies and/or anti-auto-antibodies such as anti-IgG antibodies), dyes (such as the JC-1 dye), $O_2$ monitoring systems (e.g., oxygen probes), a flow cytometry system, a mass spectrometry system (to detect mitochondrial phospholipids, such as cardiolipin and/or lysocardiolipin as well as, in an embodiment, to provide a ratio between the two phospholipids) as well nucleic acid primers and probes specific for mitochondrial DNA (such as those having the sequence of SEQ ID NO: 1, SEQ ID NO: 2, SEQ ID NO: 3, SEQ ID NO: 4, SEQ ID NO: 5 and/or SEQ ID NO: 6).

In some embodiments, the kit can also comprise means for substantially removing nucleated and/or anucleated cells from the biological sample for obtaining the enriched mixture. Such means include filters, differential centrifugation systems, magnetic beads, columns, etc. In another embodiment, when phospholipids are being measured, it may also be useful to be provided with means for substantially removing bacterial cells from the biological sample or the enriched mixture, since bacterial cells can introduce a source of contamination with some phospholipids.

In some instances, it may also be useful in to separate the free mitochondria from mitochondria microparticles in the enriched mixture. As such, the kit can also provide means for separating the enriched mixture into at least a first fraction substantially enriched in free mitochondria) and/or a second fraction (substantially enriched in mitochondria microparticles). Such means can include, for example, magnetic beads coated with antibodies specific for either free mitochondria or for mitochondria microparticles.

In yet other embodiments, it may be required to determine if an association between secreted phospholipase A2 group IIA (sPLA$_2$-IIA) and the free mitochondria and/or the mitochondria microparticle is present in the biological sample and be provided with means for doing so. Such means include, but are not limited to, fluorescent dyes, antibodies specific for sPLA$_2$-IIA, etc. In an embodiment, the presence of the secreted sPLA$_2$-IIA can be determined and optionally measured indirectly via the enzymatic activity of the secreted PLA$_2$-IIA. In such embodiments, the kit can provides means for assessing the hydrolysis of the mitochondrial membrane, such as, for example, means for determining the presence (and optionally) the quantity of cardiolipin and/or lysocardiolipin (a phospholipid, released upon hydrolysis of cardiolipin located in the mitochondrial membrane). In a particular embodiment, the kit can comprise means for determining the presence (and optionally the quantity) of cardiolipin/lysocardiolipin in a biological sample from a subject (an antibody for example), as well as instructions for determining if the subject is afflicted or susceptible to be afflicted with systematic lupus erythematosus. In such particular embodiment, the kit can also comprise instructions to stratify the subject within a group of individuals afflicted by systematic lupus erythematosus.

In a further embodiment, the kit can also comprise a container for receiving the biological sample, instructions on how to use the kits (based on the steps of the method set forth herein), as well as a control sample and/or a normogram The methods and kits described herein can be useful for determining the quality of a blood product prior to transfusion. As shown herein, extracellular mitochondrial components accumulate during blood product storage, are associated with a degradation in the quality of the blood product and can even trigger or maintain a sterile inflammatory reaction upon transfusion. As such, determining the presence or absence of extracellular mitochondrial components can be used to assess if the (stored) blood products are suitable or not for transfusion.

More specifically, the methods and kits described herein can be useful for determining the presence of activated platelets in a platelet samples. As it is shown herein, extracellular mitochondrial components can accumulate during platelet storage, are associated with the activation of platelets and can even trigger or maintain a sterile inflammatory reaction upon transfusion. As such, determining the presence or absence of extracellular mitochondrial components can be used to assess if the (stored) platelets are in a resting state or in an active state.

Inhibition of Mitochondrial Release and/or sPLA$_2$-IIA

Since it is described herein that one source of inflammatory mediators is extracellular mitochondrial components, optionally in combination with secreted phospholipase A$_2$ group IIA, the present disclosure also provides methods and agents based on limiting the release of extracellular mitochondrial components and/or the activity of the sPLA$_2$-IIA for limiting (and in some embodiments preventing or inhibiting) the production of the sterile or the infectious inflammatory mediator, and, ultimately, limiting the onset or maintenance of sterile/infectious inflammatory reactions/conditions.

The present disclosure thus provides methods as well as compositions for limiting the release of a sterile and/or an infectious inflammatory mediator from a cell. In the context of the present disclosure, the expression "limiting the release of a sterile and/or an infectious inflammatory mediator" refers to the ability of an agent or an antagonist to lower, and, in an embodiment, inhibit the release of the inflammatory mediator when compared to another cell, in the same conditions, which was not contacted with the agent. In an embodiment, the method comprises contacting an agent capable of limiting the extracellular release of an intracellular mitochondria. As used herein, the expression "limiting the extracellular release of an intracellular mitochondria" refers to the ability of an agent to lower, and, in an embodiment, inhibit the release of mitochondria which was located inside the cell into the extracellular milieu when compared to another cell, in the same conditions, which was not contacted with the agent. In an alternative or complementary embodiment, the method comprises contacting a secreted phospholipase A$_2$ group IIA (sPLA$_2$-IIA) antagonist with the cell. An "antagonist" of the sPLA$_2$-IIA refers to an agent that limits or downregulates (e.g., decreases, inhibits or lowers) the expression and/or activity of sPLA$_2$-IIA. Any known sPLA$_2$-IIA antagonist can be used in the applications described herein. Known sPLA$_2$-IIA antagonists include, but are not limited to, those described in the publication of Singer et al. 2002 (e.g., for example those presented in Table IV), of Touaibia et al. 2007 and/or of Oslund et al. 2012. The contact between the agent capable of limiting the extracellular release of an intracellular mitochondria and/or the sPLA$_2$-IIA antagonist is preferably made under conditions and for a time sufficient for limiting the release of the sterile/infectious inflammatory mediator.

In some embodiments, it may be advantageous to be provided with an agent capable of limiting the extracellular release of an intracellular mitochondria and/or an sPLA$_2$-IIA antagonist which can temporarily limit the release of the sterile/infectious inflammatory mediator. For example, when such agents and antagonists are used to limit the release of a sterile/infectious inflammatory mediator in a biological product which is being stored (e.g., a platelet preparation for example), it may be advantageous to use agents and antagonists which limit in a reversible fashion the release of the sterile/infectious inflammatory mediator. In other instances, it may be advantageous to be provided with agents and antagonists which can irreversibly limit the release of the sterile/infectious inflammatory mediator in the cell. For example, when such agents and antagonists are used to prevent, treat and/or alleviation the symptoms of a sterile or infectious inflammatory condition, it may be advantageous to use agents and antagonists which irreversibly limit the ability of a cell of releasing the sterile/infectious inflammatory mediator.

The method can be performed in vitro. Such in vitro applications are especially useful for limiting the release of sterile/infectious inflammatory mediators during the ex vivo period of a biological product (e.g., a labile biological product). The agent or antagonist can be used as an additive to a medium (e.g., solution) used to obtain the biological product, to store the biological product or to graft or transfuse the biological product. The agent or antagonist can be added to the medium prior to receiving the biological product, or when the biological product has already been placed in the medium or both. For example, the agent or the antagonist can be used as an additive to a storage solution such as a platelet storage solution. As it is known in the art, such platelet storage solutions are usually aqueous and can comprise at least one energy source, at least one buffering component, at least one chelator, at least one salt component and optionally at least one metabolic regulator and/or membrane polarity stabilizing component. In an alternative embodiment, plasma can also be used as a platelet storage solution or any other replacement storage medium The in vitro applications can be used with various types of cells which are susceptible of releasing the sterile/infectious inflammatory mediator. The cell can be nucleated or enucleated (e.g., platelets for example). The methods can be applied to a single cell type or a combination of more than one cell type. The in vitro applications can also be used to prevent or limit the onset or maintenance of a sterile/infectious inflammatory reaction in the stored biological product containing the cell.

On such example of cells which are susceptible of releasing sterile/infectious inflammatory mediators is a platelet. As is known in the art, and discussed above, during storage, platelets have a tendency to change from a resting state into an activated state. This change in state is associated with a decrease in platelet quality as well as an increased susceptibility to cause a sterile inflammatory reaction upon transfusion.

The methods and compositions described herein can also be used in in vivo applications. In such embodiments, the agent and/or antagonist is administered (or formulated for administration) to a subject in need thereof. As used herein, the "subject in need thereof" is known to be afflicted or is susceptible of being afflicted with a sterile or an infectious inflammatory condition.

The in vivo applications are aimed at preventing, treating and/or alleviating the symptoms associated with a sterile or an infectious inflammatory condition in the subject. In the context of the present disclosure, the expression "preventing, treating and/or alleviating the symptoms associated with an inflammatory condition" refer to the ability of the method, the agent or the antagonist to limit the development, progression and/or symptomology of an inflammatory condition. Symptoms associated with sterile inflammatory conditions include, but are not limited to: swelling, pain, fever or chill, erythematosus rash, urticaria, pruritus, angioedema, respiratory distress and, ultimately, mortality.

The agent and/or antagonist can be formulated as a pharmaceutical composition in combination with a pharmaceutically acceptable excipient. The pharmaceutical compositions can be administered at a pharmaceutically acceptable or therapeutically effective amount. These expressions refer to an amount (dose) effective in mediating a therapeutic benefit to a subject (for example prevention, treatment and/or alleviation of symptoms of a sterile inflammation). It is also to be understood herein that a "pharmaceutically effective amount" may be interpreted as an amount giving a desired therapeutic effect, either taken in one dose or in any dosage or route, taken alone or in combination with other therapeutic agents Screening Methods It is shown herein that extracellular mitochondrial components are released and degraded prior to and during inflammation. It is assumed that agents capable of inhibiting release of these extracellular mitochondrial components and/or the inhibiting of their degradation (for example via the enzymatic activity of sPLA$_2$-IIA) would be useful in limiting the onset and/or maintenance of inflammatory reactions/conditions.

As such, the present disclosure also provides a screening method for determining the usefulness of an agent in limiting (and in an embodiment inhibiting) or preventing the release of an inflammation mediator.

In a first embodiment of the screening application, the screened agent is first combined with a cell having an internal mitochondria. Then, the agent-cell mixture is placed under conditions allowing the extracellular release of the internal mitochondria. For example, the agent-cell mixture can be placed under conditions which, in the absence of the agent, would lead to the release of extracellular mitochondrial components. This can include, for example, a specified storage duration, a specified storage temperature, the presence of a trigger which is known to cause the release of extracellular components (e.g., thrombin for example). Once the mixture has been submitted to the appropriate conditions, it is determined if extracellular mitochondrial components are present, and in an embodiment, at which level, to obtain a test level. The test level is then compared to a control level to allow the characterization of the agent. The control level can be associated with the level of the extracellular mitochondrial components prior to the addition of the agent, or obtained prior to submitting the cells to the conditions described above. The screened agent will be considered useful for limiting (e.g., preventing) the release of the inflammatory mediator when the test level is determined to be lower than the control level. The screened agent will be considered to lack the usefulness for limiting (e.g., preventing) the release of the inflammatory mediator when the test level is determined to be equal to or higher than the control level.

In a second embodiment of the screening application, the cell is placed under conditions allowing the extracellular release of the internal mitochondria. For example, the cell can be placed under conditions which would lead to the release of extracellular mitochondrial components. This can include, for example, a specified storage duration, a specified storage temperature, the presence of a trigger which is known to cause the release of extracellular components (e.g., thrombin for example). Once the cell has been submitted to the appropriate conditions, it is admixed with the screened agent and, afterwards, it is determined if extracellular mitochondrial components are present, and in an embodiment, at which level, to obtain a test level. The test level is then compared to a control level to allow the characterization of the agent. The control level can be associated with the level of the extracellular mitochondrial components obtained in the presence of an agent which cannot limit the release of the extracellular mitochondrial component (a sterile buffer or diluent for example) or obtained prior to submitting the cells to the conditions described above. The screened agent will be considered useful for limiting (e.g., inhibiting) the release of the inflammatory mediator when the test level is determined to be lower than the control level. The screened agent will be considered to lack the usefulness for limiting (e.g., inhibiting) the release of the inflammatory mediator when the test level is determined to be equal to or higher than the control level.

Processes for Isolating Extracellular Mitochondrial Components from Blood and Blood Products The present disclosure provides a process for isolating in a "substantially pure" form extracellular mitochondrial components that may be present in a biological product (e.g., blood, a blood product such as, for example, a platelet preparation). As used herein, the term "substantially pure" indicate that, once isolated, the weight ratio of the extracellular mitochondrial components is the highest when compared to the weight ratio of the components of final isolated mixture. Such process may be useful for further characterizing the extracellular mitochondrial components. Throughout this process, it is preferable to avoid or limit non-specific cellular lysis to avoid the non-specific release of extracellular mitochondrial components in the extracellular milieu.

In a first step, the process comprises obtaining blood or a blood product. The sample can optionally be treated with a platelet activator (for example thrombin) to increase the amount or the types of extracellular mitochondrial components. The sample can also optionally be treated with an agent capable of limiting the release of intracellular mitochondria from a cell and/or an sPLA$_2$-IIA antagonist.

Once blood or the blood product has been obtained, it can optionally be treated to substantially remove the cells (such as platelets) from the sample to obtain a cell-free mixture. This step is optional when the subsequent isolation step relies on a process which can discriminate between intracellular and extracellular components (flow cytometry associated with cell sorting for example). This step is mandatory when the subsequent isolation step cannot discriminate between intracellular and extracellular components.

The extracellular mitochondrial components are then isolated from the sample or the cell-free mixture either using an antibody or a lectin specific for the mitochondrial components or selecting a fraction of the sample or the cell-free mixture which is enriched in extracellular mitochondrial components (e.g., components having a relative size lower then about 1 µm) to obtain the substantially isolated extracellular mitochondrial components.

In some processes, it may be useful to be provided with a fraction which is substantially enriched in free mitochondria. In such embodiments, the process can include further isolating the free mitochondria using an antibody or a lectin specific for the free mitochondria. In other embodiments, it may be useful to be provided with a fraction which is substantially enriched in mitochondria microparticles. In such embodiments, the process can include further isolating the mitochondria microparticles using an antibody or a lectin specific for the mitochondria microparticles.

The present invention will be more readily understood by referring to the following examples which are given to illustrate the invention rather than to limit its scope.

Example I—Materials and Methods

Mice.

All studies were approved by the institutional review board protocol (Université Laval). Guidelines of the Canadian Council on Animal Care were followed in a protocol approved by the Animal Welfare Committee at Laval University. For our studies, we used 6- to 10-week-old male mice (C57BL/6N and BALB/c; Charles River). For in vivo experiments in which secreted phospholipase $A_2$ IIA (s$PLA_2$-IIA) contribution is evaluated, we used C57BL/6J (Jackson Laboratories) and s$PLA_2$-IIA-sufficient mice as previously reported (Grass et al. 1996).

Cells and Human Fluid Preparation.

Blood was obtained from healthy human volunteers (citrate as anticoagulant) under an approved institutional review board protocol (CRCHUQ; Université Laval) and in accordance with the Declaration of Helsinki. Platelets, platelet MPs (96% of them expressing CD41), and human polymorphonuclear leukocytes were prepared as previously described (Cloutier et al. 2013). Platelet-free plasma (PFP) was obtained from platelet storage bag preparations as previously reported (Thibault et al. 2006). Briefly, leukoreduced platelet concentrates were prepared from 6 healthy blood donors and incubated for 5 days at 20° C. to 24° C. with agitation. PFP samples were obtained on days 0, 1, and 5 and were monitored immediately after collection (without freezing). An increase in platelet P-selectin expression was less than 2% was observed during total storage time (day 1 vs. day 5). Synovial fluids of rheumatoid arthritis (RA) and osteoarthritis patients were obtained from volunteers under the approval of the institutional review board protocol (Brigham and Women's Hospital) and were used to assess mitochondria-containing MPs (mitoMPs). The freshly obtained synovial fluid of RA patients (Table 1) was cleared of leukocytes by centrifugation at 1900 g for 30 minutes at 4° C.

TABLE 1

Description of synovial fluid specimen from rheumatoid arthritis patients. SF: Synovial fluid; RF: Rheumatoid Factor; CCP: Cyclic citrullinated peptide; CRP: C-reactive protein; ESR: Erythrocyte sedimentation rate.

| Specimen | Gender | Age | Specimen description | RF | CCP | CRP | ESR |
|---|---|---|---|---|---|---|---|
| 1 | Male | 48 | Knee SF | N/A | N/A | 4.2 | 25 |
| 2 | Male | 35 | Knee SF | <30 | 3 | 44.5 | 64 |
| 3 | Male | 72 | Knee SF | 134 | 37 | 25.4 | 23 |

Isolation of Mouse Liver Mitochondria.

Mitochondria were isolated from the liver of C57BL/6N mice with the Qproteome mitochondria isolation kit (QIAgen), according to the manufacturer's protocol. The mitochondria pellet was resuspended in Tyrode buffer, pH 7.4 (134 mM NaCl, 2.9 mM KCl, 0.34 mM $Na_2HPO_4$, 12 mM $NaHCO_3$, 20 mM N-2-hydroxyethylpiperazine-N9-2-ethanesulfonic acid, 1 mM $MgCl_2$, 5 mM glucose, and 0.5 mg/mL bovine serum albumin), labeled with MitoTracker Deep Red™ (100 nM; Invitrogen), and counted by flow cytometry on a BD fluorescence-activated cell sorter (FACS) Canto II SORP small particle option.

High-Sensitivity Flow Cytometry Configuration.

A forward scatter (FSC) coupled to a photomultiplier tube (PMT) "small particles option" (FSC-PMT) (rather than the usual diode) with a 488-nm solid state, 100-mW output blue laser (rather than the conventional 20 mW), a 633-nm HeNe, 20-mW output red laser, and a 405-nm solid state diode, 50-mW output violet laser were mounted on the BD FACS Canto II Special Order Research Product used for all our studies (BD Biosciences). The chosen parameters were optimal to detect particles from 100 to 3 500 nm simultaneously on the FSC-PMT.

Platelet Stimulation.

Platelets were labeled with MitoTracker Deep Red™ and PKH67 Green Fluorescent Cell Linker as described above. Platelets were washed and then were left nonactivated or activated using heat-aggregated immunoglobulin (Ig)G (HA-IgG), 1 mg/mL; thrombin, 0.5 U/mL; collagen, 5 µg/mL; for 4 hours at room temperature. Platelets (20 mL) were then diluted into 500 mL phosphate-buffered saline (PBS) and analyzed by flow cytometry. For extracellular mitochondria release experiments, platelets were treated with cytochalasin B (20 mM; Sigma-Aldrich), cytochalasin D (1 mM; Sigma-Aldrich), cytochalasin E (4 mM; Cayman Chemical), latrunculin A (10 mM; Cayman Chemical), or nocodazole (5 mM; Sigma-Aldrich). To process the data quantitatively, 100 000 polystyrene microspheres (15 mm diameter; Polysciences) were added to each tube, and 1000 microspheres were acquired. The included MitoTracker$^+$ and/or PKH67$^+$ events were portrayed as FSC-PMT vs a side scatter (SSC) graph, and the relative dimensions were displayed according to the acquisition of Sky Blue microspheres of mean diameters of 90, 220, 450, 840, and 3 200 nm (Spherotech).

Mitochondrial Activity.

Oxygen consumption was measured with mitochondrial preparations (final concentration of ~0.15 mg protein/mL) using a temperature-controlled polarographic $O_2$ monitoring system with 1-mL chambers (Rank Brothers Ltd). Temperature was maintained at 37° C. by a circulating temperature-controlled water bath (Haake G8; Polyscience). The oxygen probes were calibrated with air-saturated reaction buffer and corrected for temperature and atmospheric pressure. All components were dissolved in reaction buffer (140 mM KCl, 20 mM N-2-hydroxyethylpiperazine-N9-2-ethanesulfonic acid, and 5 mM $K_2HPO_4$, pH 7.3, with 0.5% fatty acid free bovine serum albumin), except rotenone and antimycin A, which were dissolved in 95% ethanol.

Oxygen consumption due to flux through complexes I to IV was estimated from rates of pyruvate+malate+succinate oxidation (3.45, 0.37, and 6 mM) in the presence of 5 mM adenosine 5'-diphosphate and corrected for residual rates after inhibition of complex I by rotenone (1 mg/mL final concentration) and complex III by antimycin A (5 mg/mL final concentration). Preliminary experiments showed that 5 mM adenosine diphosphate was sufficient to maintain state 3 rates for the time required for the complete series of measurements. Preliminary experiments also established optimal substrate and inhibitor concentrations for these measurements from platelet mitochondria.

Mitochondria membrane potential was performed as described in the JC-1 Mitochondrial Membrane Potential Detection Kit protocol (Cayman Chemical). Platelet supernatant was incubated with JC-1 (1/10) as recommended by the manufacturer, and with 5 mL of anti-CD41a-APC (BD Biosciences) for 30 minutes at 37° C. Samples were diluted and analyzed using high-sensitivity flow cytometry (hs-FCM).

Air Pouch Model.

The air pouch model was performed on C57BL/6N mice as previously reported (Willoughby et al. 1986). Briefly, sterile air was subcutaneous injected on days 0 and 3. Tumor necrosis factor-α (50 ng) was injected into the pouch on day 6. On day 7, mitochondrial membrane hydrolysis products (100 mL of $5 \times 10^8$ mitochondria treated with sPLA$_2$-IIA), diluent (PBS), sPLA$_2$-IIA, or mitochondria alone were injected in the air pouch. After 4 hours, the air pouch was washed with 1.2 mL PBS. Cytokines were quantified using the BD Cytometric Bead Array System (CBA) (BD Biosciences) by flow cytometry on a BD FACS Canto II and analyzed using FCAP Array Software v3.0.

Isolation and Quantification of Free Mitochondria.

Free mitochondria were isolated from diverse samples with an anti-TOM22 microbeads kit (Miltenyi Biotec), with a minor modification. The initial step consisting of cell lysis was omitted since only soluble free mitochondria were targeted for isolation. Free mitochondria were subsequently isolated via magnetic field. Mitochondrial DNA was extracted from eluted anti-TOM22 processed samples with the QIAamp DNA Micro extraction kit (QIAgen) according to the manufacturer's protocol and quantified by realtime quantitative PCR (Rotor Gene-3000, QIAgen) with the Rotor-Gene Probe PCR kit (QIAgen). Primers and probes (Integrated DNA Technologies) were used for specific amplification of human (forward 5'-ACGCCTGAGC-CCTATCTATTA-3' (SEQ ID NO: 1), reverse 5'-GTTGAC-CTGTTAGGGTGAGAAG-3' (SEQ ID NO: 2) and probe 5'-/56-FAM/TGACAAGCG/ZEN/CCTATAGCACTCGAA/3IABkFQ/-3' (SEQ ID NO: 3)) and mouse (forward 5'-GGAACAACCCTAGTCGAATGAA-3' (SEQ ID NO: 4), reverse 5'-GCTAGGGCCGCGATAATAAA-3' (SEQ ID NO: 5) 5'-/56-FAM/ACAAAGCCA/ZEN/CCTTGAC-CCGATTCT/3IABkFQ/-3' (SEQ ID NO: 6)) mitochondrial DNA. The qPCR cycling condition consisted of an initial step of 95° C. for 3 min followed by a two-step amplification of 95° C. for 3 s and 60° C. for 10 s (40 cycles). Mitochondrial DNA extracted from platelet was used for generation of standard curve.

Mitochondrial DNA Quantification in Platelet Concentrates Associated with Acute Transfusion Reactions.

Of the 10 600 apheresis platelet concentrate transfusions performed over 2 consecutive years, 74 platelet concentrates were associated with Acute Transfusion Reactions (ATRs). Only severe cases were considered in our study, Grade 3 of the International Society Blood Transfusion (ISBT) scale. Symptoms were mainly febrile non-hemolytic reactions (42% of ATRs), skin manifestations such as itching or skin rash (38% of ATRs) and cardiovascular events such as hypotension or tachycardia (20% of ATRs). Recipients were women in 53% of cases and mean age was 47.3±10.5 years. All platelet concentrate collections were subjected to quality control to ensure consistency and compliance with French and European standards (EDQM, 16$^{th}$ Edition, 2010). Several parameters were assessed including volume (mean volume=419±30 ml), mean platelet count ($5.6 \pm 0.6 \times 10^{11}$ platelets/bag), mean residual leukocyte count ($0.095 \pm 0.087 \times 10^6$ leukocytes/bag) and mean pH (7.3±0.1).

1 MtDNA quantification in platelet concentrates (ATR vs. control-matched storage duration) was performed by qPCR as described above.

Transmission Electron Microscopy and Determination of Relative Position of Mitochondria within Platelets.

Platelets and platelet MPs (freshly obtained and never frozen) were fixed in 2.5% glutaraldehyde for 30 min at room temperature (RT) then stored at 4° C. until paraffin inclusion. Samples were stained and analyzed on a FEI Tecnai G2 Spirit BioTWIN transmission electron microscope at 80 kV. Relative positioning was calculated using a custom made macro for NIH ImageJ. Each platelet contour was drawn with the free hand tool to calculate their centroid, which was subsequently marked on the picture as a landmark. Minimum and maximum radii of the platelet were then measured using the line tool. Centroids were also determined for each mitochondrion and marked on the microphotograph. The distance between the platelet centroid and the mitochondria centroids was measured as well as the shortest distance between the mitochondria centroids and the plasma membrane.

Scanning Electron Microscopy Imaging.

Samples were fixed with 2.5% glutaraldehyde for at least 24 h then processed for standard dehydration. Briefly, samples were first washed (3×10 min) with sodium cacodylate buffer (0.1 M, pH 7.3) then fixed with osmium tetroxide (1% in sodium cacodylate buffer) for 90 min. Samples were washed again (3×10 min) in sodium cacodylate buffer and subsequently processed for alcohol dehydration steps (50, 70, 95 and 100% EtOH, 10 min each steps). Samples were then dipped in 100% EtOH for 40 and 10 min, and air-dried overnight. Samples were then coated with palladium and observed with a JEOL 6360LV scanning electron microscope (Tokyo, Japan).

Live Cell Imaging of Platelet Activation and Confocal Immunofluorescence Microscopy.

Mitochondrion staining was performed on isolated platelets ($10^8$ cells/ml) in the presence of MitoTracker® Green FM or Deep Red FM (100 nM, Invitrogen) incubated for 45 min at 37° C. Cell membrane staining was achieved with the addition of wheat germ agglutinin (WGA) Alexa Fluor 594-conjugate (5 μg/ml, Invitrogen) or PKH67 Green Fluorescent Cell Linker (0.75 μM, Sigma-Aldrich) that was added 15 min before the end of incubation. Cells for live cell imaging were incubated in 8 well-chamber slides and maintained at 22° C. within a top-stage incubator (Tokai Hit ZILC-F1) during the entire acquisition. Single plane of platelets were acquired every 20 s for 105 min. For confocal immunofluorescence microscopy, resting labeled cells were immediately fixed with 2% paraformaldehyde (PFA) for 5 min at RT and smeared on a Superfrost Plus glass slide (Fisher Scientific). Fluoromount (Sigma-Aldrich) was added as mounting agent. For activated platelets, platelets were stimulated with 0.5 U/ml of thrombin for 2 h at RT. The supernatant of activated platelets was labeled with anti-CD41-V450 and MitoTracker® Deep Red FM (100 nM) for 30 min at RT in the dark. The reaction was stopped with PFA 2% fixation and sample was smeared on a Superfrost Plus glass slide. Fluoromount was added and samples were then analyzed by confocal laser scanning microscopy. Confocal laser scanning microscopy was performed with an IX81-ZDC microscope equipped with a FV1000 scanning head and an Olympus 60X OSC NA 1.4 objective lens. Confocal images were acquired by sequential scanning with the 488 nm, 546 nm and 633 nm laser lines, and the variable bandwidth filters were set optimally according to the spectral properties for MitoTracker® Green FM and WGA Alexa Fluor 594-conjugate. The Fluoview imaging software ASW3.1a (Olympus America Inc.) was used to acquire and export the z-stacks. Maximum intensity projections and volume rendering were calculated using the Surpass module in Bitplane Imaris 7.5.1 (Zurich, Switzerland). Colocalization analysis was performed with the Bitplane Imaris 7.5.1 colocalization module using the Costes' estimation for automatic threshold, which compares the Pearson's coefficient for non-randomized vs. randomized images and calculates the significance.2 Colocalization channel of mitochondria with sPLA2-IIA was generated for visual representation, and Pearson's coefficients were calculated.

Internalization of Mitochondria by Human Neutrophils.

Neutrophils ($5 \times 10^8$ cells/ml) were labeled with CMPTX (1 µM, Invitrogen) for 15 min at 37° C. in HBSS 1×. Neutrophils were pre-treated with 1 µM final concentration of cytochalasin B (Sigma), 10 µM of nocodazol (Sigma), 50 µM of dynasore (Sigma), 10 µg/ml of nystatin (EMD Milipore), or 40 µM of chlorpromazine (LKT Laboratories) for 10 min at 37° C. Cells were then incubated for 30 min at 37° C. in the presence of $5 \times 10^5$ mitochondria/µl (labeled with 100 nM final of MitoTracker® Deep Red, Invitrogen) and recombinant human sPLA$_2$-IIA (0.2 µg/ml). Cells were finally labeled with Hoestch (1 µg/ml), fixed in 2% PFA and cytospined at 500 RPM for 3 min. Mitochondrial internalization in human neutrophils was then evaluated by confocal microscopy.

Multiphoton Microscopy and Leukocyte Speed Quantification.

Heterozygous LysM-eGFP knock-in mice3 were anesthetized with 2-3% isoflurane in O$_2$, hairs from their right ear were removed using depilatory cream (Nair®) and the ear was held in place with physiological glue (MSI-EpiDerm-Glu). Vasculature was visualized by injecting 1% Qdot 705 (Life Technologies) diluted in sterile Tyrode Buffer pH 7.4 in the tail vein. Blood vessels between 14-20 µm in diameter were localized with epifluorescence and used for leukocyte speed quantification. A volume of 100 µL of mitochondria ($5 \times 10^8$) or Tyrode Buffer (diluent) was next injected i.v., at which point continuous acquisition started for 40 minutes. The average leukocyte speed was measured as the distance travelled (in µm) in a given number of images acquired at 0.859 frames per second. Body temperature was maintained at 37° C. during all procedures with a temperature controlling device (RWD Life Science Co.). All images were acquired on an Olympus FV1000 MPE 2-photon microscope as previously described (Soulet et al. 2013). Images recorded for the 40-minute quantification period and for stacks had a resolution of 256×256 and 320×320 pixels, respectively.

Generation of Alexa Fluor 488-Conjugated Recombinant sPLA$_2$-IIA.

Recombinant sPLA$_2$-IIA labeled with an Alexa Fluor 488 fluorescent dye was prepared as follows. The S36C mutation was created using the QuickChange kit (Agilent Technologies) and confirmed by DNA sequencing of the full coding region of the protein expression plasmid (Canaan et al. 2002). The inclusion body protein from bacterial expression was refolded to obtain the protein containing an extra cysteine residue disulfide linked to cysteine-36 (Canaan et al. 2002). The disulfide bond was cleaved by mild dithiothreitol treatment and labeled with Alexa Fluor488 C$_5$-maleimide (Life Technologies). The labeling method and purification of the labeled protein free of excess dye reagent was carried out as described previously for site selective spin labeling of sPLA$_2$-IIA on surface cysteine residues (Canaan et al. 2002). The catalytically inactive H48Q mutant of human sPLA$_2$-IIA was produced as previously described (Edwards et al. 2002).

sPLA$_2$-IIA Binding to Mitochondria.

Mitochondria ($10^6$) from mouse liver were labeled with 100 nM of MitoTracker® Deep Red and incubated with 10 ng of sPLA$_2$-IIA Alexa Fluor 488 (final volume 10 µl) in HBSS with 5 mM of CaCl$_2$ for 30 min on ice. Samples were diluted and the presence of sPLA$_2$-IIA Alexa Fluor 488 on fluorescent mitochondria was analyzed by flow cytometry.

Interaction between mitochondria and sPLA$_2$-IIA was also assessed by immunolabeling and co-elution. Unstained mouse liver mitochondria ($10^7$) in HBSS with 5 mM CaCl$_2$ were incubated with 250 ng of sPLA$_2$-IIA (final volume 100 µl) for 30 min on ice. Anti-TOM22 microbeads labeling was then performed as described above and processed on a magnet for mitochondria isolation. Mitochondria were then pelleted and lysed in 1× lysis buffer. Samples were electrophoresed, transferred onto membranes and incubated in 0.2% milk/TBS-Tween solution containing rabbit anti-sPLA$_2$-IIA antibody (1/1000, Cayman Chemical) for 48 h at 4° C. The membrane was washed, treated with Peroxidase-AffiniPure anti-rabbit-IgG (Jackson ImmunoResearch) and reactive proteins were visualized by chemiluminescence (Perkin Elmer).

For immunofluorescence visualization, neutrophils ($5 \times 10^6$/ml) were labeled with CMPTX Cell Tracker (5 µM, Invitrogen) for 15 min at RT and incubated with $5 \times 10^5$ mitochondria (pre-incubated with sPLA$_2$-IIA) during 30 min at 37° C. Hoechst (1 µg/ml) was added 10 min before the end of incubation time and reaction was stopped with addition of 4% PFA. Cells were analyzed by flow cytometry and were also prepared for microscopy using a cytospin protocol (500 RPM for 5 min at 4° C.) and analyzed by confocal laser scanning microscopy as described below.

Mass Spectrometry Analysis of Lysophospholipids and Fatty Acid Released from Mitochondrial Membranes by Human Recombinant sPLA$_2$-IIA.

Mitochondria were incubated in the presence of 0.1 µg/ml and 1 µg/ml of human recombinant sPLA$_2$-IIA at 37° C. for 0.5 and 6 h. Mitochondria were also incubated in the absence of sPLA$_2$-IIA to determine the content of basal free fatty acid. Following incubation, the reaction was stopped with the addition of 20 mM of EGTA. Lysophospholipid analysis by mass spectrometry was carried out as described (Bollinger et al. 2010). Samples of sPLA$_2$-IIA-treated mitochondria (200 µl) was mixed with 800 µl of chloroform/methanol (2/1) followed by the addition of 15 µl of internal standard mixture (Bollinger et al. 2010 B). Samples were extracted as described and analyzed by combined liquid chromatography/tandem mass spectrometry (Bollinger et al. 2010). Fatty acids were analyzed by conversion to their AMPP amide derivatives and then analyzed by combined liquid chromatography/tandem mass spectrometry.

Stimulation of Neutrophils for Leukotriene Generation.

Human recombinant wild-type sPLA$_2$-IIA9, its catalytically inactive mutant form H48Q6 or vehicle diluent were incubated 18 h at 5 µg/ml in the presence of mouse liver mitochondria ($5 \times 10^5$ mitochondria/pi in Tyrode Buffer, pH 7.4, supplemented with 5 mM CaCl$_2$) at 37° C. Human neutrophils were primed and stimulated for leukotriene biosynthesis as previously described (Cloutier et al. 2013, Flamand et al. 2006). To evaluate sPLA$_2$-IIA mediated release of arachidonic acid, cPLA$_2\alpha$ inhibitor pyrrophenone (100 nM) was added 5 min before stimulation. Stimulation was initiated by the addition of 5 µl of pre-treated mitochondria, or control, to prime neutrophils. The reaction was stopped by the addition of 500 µl of cold MeOH:CH$_3$CN (1:1) containing 12.5 ng of prostaglandin B2 as internal standard. Samples were then processed and analyzed by reversed-phase high performance liquid chromatography using on-line extraction as previously described (Borgeat et al. 1990).

NET Quantification.

Activated human neutrophils (5×10$^6$ cells/ml) were incubated in the presence of labeled mitochondria (5×10$^5$ mitochondria/ml, MitoTracker® Deep Red, 100 nm) and sPLA$_2$-IIA (0.1 µg/ml) or diluent (PBS) for 2 h at 37° C. Cells were then fixed with 2% PFA and DNA staining was performed with Hoestch 33342 (1 µg/ml, Invitrogen). Cells were cytospinned on a slide at 500 RPM for 3 min. NET formation (%) was determined by the following equation: (NETs/PMN counted)*100. Preliminary experiments confirmed that mtDNA is readily distinguished from neutrophils NETs.

Quantification of Mitochondrial DNA Release Following Incubation with Human Recombinant sPLA2-IIA.

Mitochondria were seeded at 5×10$^8$ mitochondria/mL (Tyrode Buffer, pH 7.4, +5 mM CaCl$_2$) in a flat bottom well plate (Costar, Corning). Human recombinant sPLA$_2$-IIA (5 µg/ml) or diluent (PBS) was added and samples were then incubated for 30 min at 37° C. Nucleic acid stain Sytox® Green (2.5 µM, Invitrogen) was added to the mix and incubated for 10 min at room temperature. Fluorescence was obtained with a Tecan apparatus. To calculate the percentage of mitochondrial DNA released in the milieu, Triton X-100 (0.1% PBS) lysis of an equivalent amount of mitochondria (5×10$^8$ mitochondria/ml) was performed, to determine the total amount of mitochondrial DNA present per well.

mRNA Quantification of Inflammatory Genes.

Mitochondria (or Tyrode Buffer as diluent) were intravenously injected in sPLA$_2$-IIA sufficient or deficient mice. After 1 h, mice were sacrificed and organs (heart, thymus, spleen, liver, kidneys, lymph nodes and lungs) were recovered and immediately processed for total RNA extraction. Total RNA was isolated using Trizol (Life Technologies Inc.), according to the manufacturers protocol. RNA was quantified using a Qubit® Fluorometer (Life Technologies Inc.). Reverse transcription was performed using 1 µg of total RNA with Transcriptor First Strand cDNA Synthesis Kit (Roche Applied Science), following the manufacturers instructions. Real-time PCR was performed as described previously (Dussault et al. 2006). Briefly, cDNA amplification was carried out in a Rotor-Gene Q operated with the Q series software version 2.0.2 (Qiagen) using 35 cycles of 95° C. for 17 s, 58° C. for 25 s and 72° C. for 25 s. Each sample consisted of 40 ng of cDNA, 2 µl of 10× buffer (100 mM Tris, 500 mM KCl, 30 mM MgCl$_2$, 1.5% Triton X-100), 100 µM dNTP, 500 nM of primers, 0.1 unit of Taq DNA polymerase (Roche Applied Science) and SYBR® Green I dye (Life Technologies) in a reaction volume of 20 µL. For each gene of interest, specific primers were designed as described previously (Dussault et al. 2006).

Example II—Characterization of Mitochondria Released from Platelets

The material and methods used in this Example are provided in Example I.

Figure 1B:
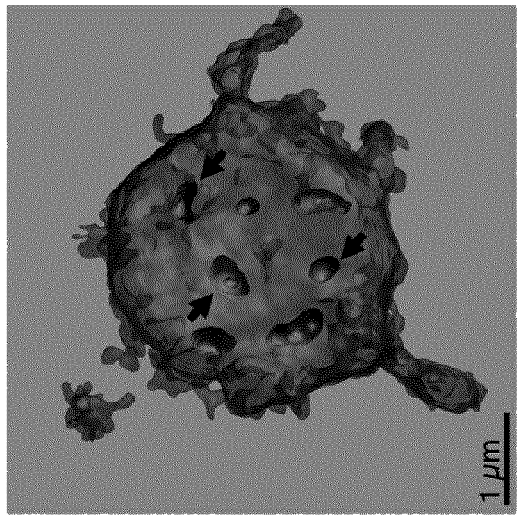
Figure 1A:
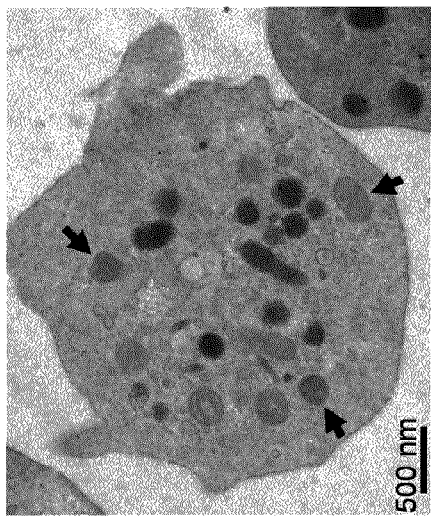
Figure 8B:
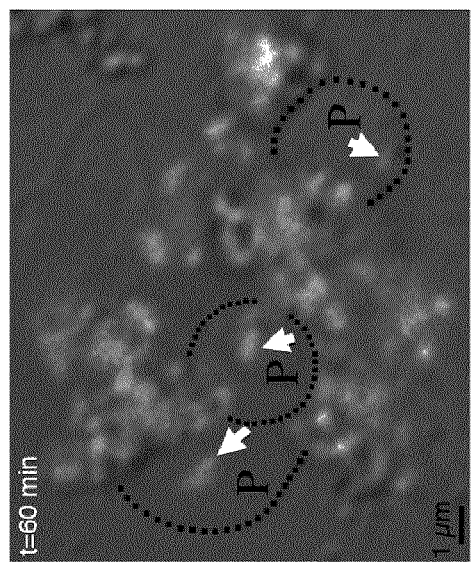
FIG. 8. Relative positioning of mitochondria within the platelet. (A) Platelet centroid (indicated by X), as well as mitochondrial centroids (indicated by white dots), were calculated using a custom-made macro for NIH ImageJ and marked on the microphotograph. The distance between the platelet centroid and the mitochondrial centroids was measured along with the shortest distance between the mitochondrial centroids and the plasma membrane. (B) Timelapse imaging of mitochondria movement in thrombin-activated platelets. A proportion of mitochondria (white arrow) are found within pseudopodia (P, dotted lines) of thrombin-activated platelets (t=60 min).
Figure 8A:
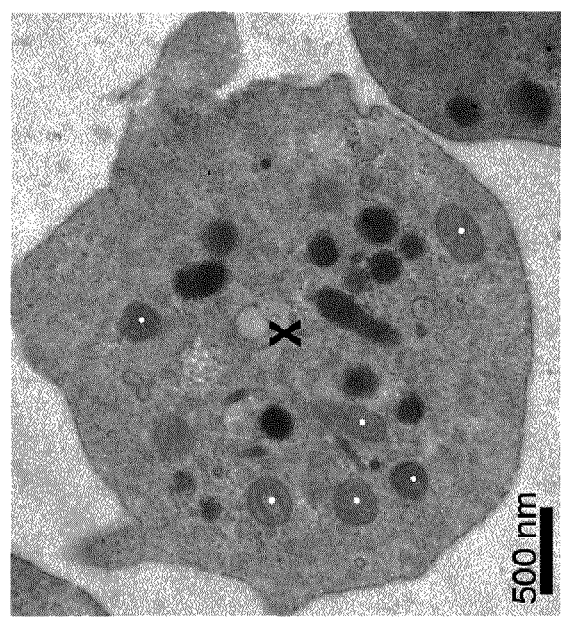

Using fluorescence and transmission electron microscopy (TEM), we found that unactivated platelets contain an average of ~4 mitochondria, frequently located in the vicinity of the plasma membrane (FIGS. 1A-C; FIG. 8A and data not shown). Remarkably, a fraction of these mitochondria promptly localizes in pseudopodia on activation by thrombin, a serine protease that participates in blood coagulation (FIG. 8B and data not shown).

In addition to promoting release of granule contents, platelet activation triggers cytoplasmic membrane budding and the shedding of submicron vesicles called microparticles (MPs) (Boilard et al. 2012, György et al. 2011). Taking into account the localization of mitochondria in the vicinity of the cytoplasmic membrane, we hypothesized that mitochondria might be packaged within MPs and form mitochondria-containing microparticles (mitoMPs).

Mitochondria are recognized as the powerhouse of the cell, producing the energy (adenosine triphosphate) required for most metabolic reactions, mostly via oxidative phosphorylation. To determine whether platelets release mitochondria, we first evaluated specific mitochondrial O$_2$ consumption, mediated by flux through complexes I to IV, using specific inhibitors of complexes I and III (roteonone and antimycin A, respectively). Unless mitochondria have been isolated and free in the milieu, permeabilization of the cytoplasmic membrane is for access of exogenous substrates added exogenously to stimulate mitochondrial respiration. To evaluate respiration by putative mitoMPs in platelet-free supernatants, we thus used an established permeabilization method for our assays (Clerc et al. 2012). We found that the supernatant from activated platelets harvested by centrifugation (cell-free; FIG. 9) consumes O$_2$ (FIG. 2A). In contrast, the supernatant from isolated resting platelets exhibited no detectable O$_2$ consumption (FIG. 2A). Quite unexpectedly, significant O$_2$ consumption was detected even in the absence of detergent (FIG. 2A). These observations suggest that, in addition to active mitoMPs, platelets may also release respiration-competent free mitochondria (freeMito) into the extracellular milieu (FIG. 2B).

We next examined the presence of freeMitos and mitoMPs, using a series of quantitative and qualitative approaches. Using a monoclonal antibody directed against a specific mitochondrial outer membrane receptor (TOM22; FIG. 10), we found intact freeMitos in the supernatants from thrombin-activated platelets, quantified by a PCR approach targeting mtDNA sequences (FIG. 2C). TEM and confocal fluorescence microscopic analyses using fluorescent dyes to discriminate the plasma membrane and mitochondria further confirmed the production of freeMitos and mitoMPs by activated platelets (FIGS. 2D-E).

Figure 2F:
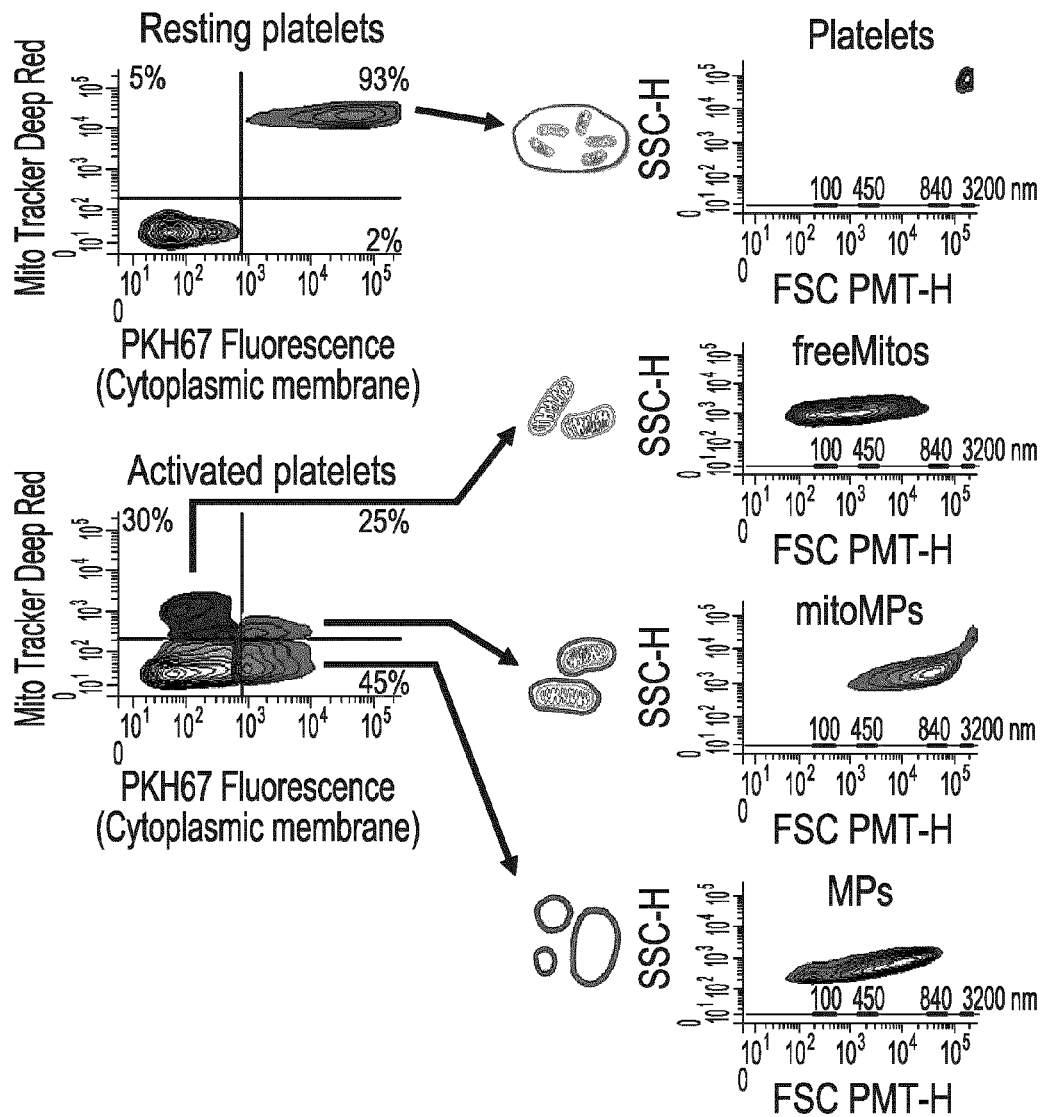
FIG. 2. Activated platelets release extracellular mitochondria. (A) Platelet-free supernatants resulting from the isolation of thrombin-activated platelets consume $O_2$ via the electron transport chain following cell permeabilization with saponin detergent (50 mg/mL). No $O_2$ consumption is detected in supernatants obtained from resting platelets (n=4; data are mean±SEM). (B) Three predicted types of extracellular microparticles (MPs) produced on platelet activation: mitochondria (freeMitos), mitochondria-containing MPs (mitoMPs), and MPs lacking mitochondria (MPs). (C) Isolation of freeMitos using anti-TOM22 microbeads (or IgG control) in thrombin-stimulated platelets and mtDNA quantification (n=4; data are mean±SEM, **$P<0.005$, t test). (D) TEM visualization of freeMitos (white arrows), mitoMPs (black arrows), and MPs (black arrowheads) released from thrombin activated platelets. (E) Three-dimensional CSLM reconstruction of the supernatant of thrombin-activated platelets. Populations represented in image are platelets (black arrow), MPs (white arrows), mitoMPs (white arrowheads), and freeMitos (black arrowheads). (F) High-sensitivity flow cytometry (hs-FCM) analysis of resting platelets (upper panel, top right quadrant) and thrombin-activated platelets, which show 3 additional, distinct populations of particles, i.e., freeMitos (bottom panel, top left quadrant), mitoMPs (bottom panel, top right quadrant), and mitochondria-free MPs (bottom panel, bottom right quadrant). Bottom left quadrant of both upper and lower panels represents background noise (gray). FSC-PMT and SSC dot plots of platelets (first right panel) and 3 populations of microparticles: freeMitos (second right panel), mitoMPs (third right panel), and MPs (fourth right panel). The relative diameters are presented according to size-defined microsphere calibrations. (G) Release of (left) freeMito), (center) mitoMPs, and (right) MPs from thrombin-activated platelets require intact actin microfilament dynamics. Mitochondrial release is significantly reduced on addition of actin inhibitors (cytochalasin [B,D,E] and latrunculin [A]), but not tubulin polymerization inhibitor (nocodazole) (n=4; data are mean±SEM, *P<0.05, P<0.005, and *P<0.001, t test). (H) Heat-aggregated IgG (HA-IgG), thrombin, collagen, cross-linked collagen related peptide (CRP-XL), and phorbol 12-myristate 13-acetate (PMA) trigger the release of (left) extracellular freeMitos, (center) mitoMPs, and (right) MPs quantified by hs-FCM (n=4; data are mean±SEM. *P<0.05, P<0.005, and *P<0.001 vs supernatant from resting platelets, t test).

Given that the transfer of organelles from megakaryocytes to platelets is mediated by cytoskeleton components, we assessed whether the cytoskeleton is also involved in the extrusion of mitochondria from platelets. Using actin and tubulin polymerization inhibitors along with hs-FCM29 to resolve the submicron particle populations (i.e., MPs, mitoMPs, and freeMitos; FIG. 2B) produced by platelets, we observed that the release of mitochondria (freeMitos and mitoMPs) involves actin and occurs independently of microtubules (FIG. 2F-G). Thus, via cytoskeletal contribution, activated platelets are a source of mitoMPs and respiration-competent freeMitos.

Figure 11A:
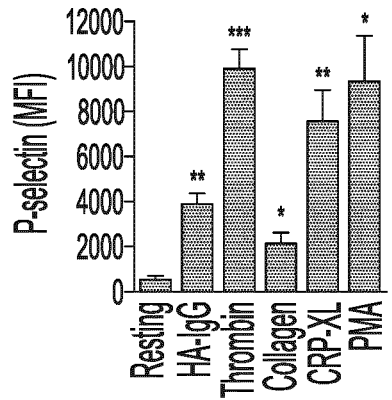
FIG. 11. Platelet are activated under various stimuli. (A and B) Platelets were activated using heat-aggregated IgG (HA-IgG), thrombin, collagen, crosslinked collagen related peptide (CRP-XL) and phorbol 12-myristate 13-acetate (PMA) for 4 hours at room temperature. (A) P-Selectin and (C) activated glycoprotein IIb/IIIa expression (PAC-1 antibody) in activated platelets by FCM. Values represent the mean fluorescence intensity (MFI) (n=3; data are mean±SEM. *P<0.05, P<0.005 and *P<0.001 vs. resting platelets, t-test). (B) 12-Hydroxyeicosatetraenoic acid (12-HETE) quantification by high-performance liquid chromatography of activated platelets.
Figure 11B:
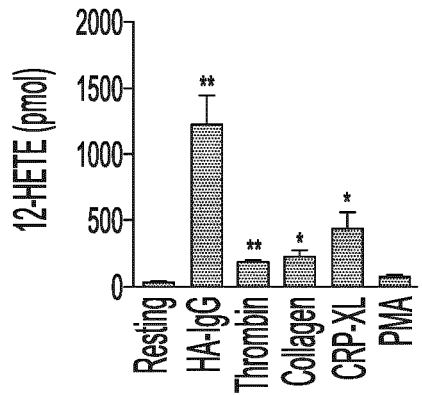
Figure 11C:
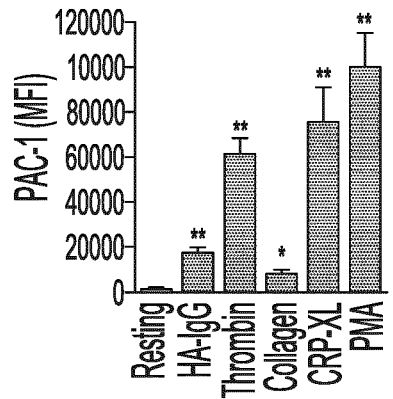

In light of the fact that thrombin is a highly potent agonist of platelet activation, we next aimed at determining whether this activator as well as other recognized platelet stimuli (FIGS. 11A-B) promote the release of extracellular mitochondria. We found that all the platelet stimuli tested lead to the production of both mitoMPs and freeMitos (FIG. 2H). Interestingly, freeMitos were found to fulfill the current structural definition of conventional MPs. In fact, freeMitos are smaller than intact platelets and have submicron dimensions and a membrane moiety (FIG. 2F), providing an explanation for the recognized heterogeneity found among platelet-derived MPs.

Figure 3A:
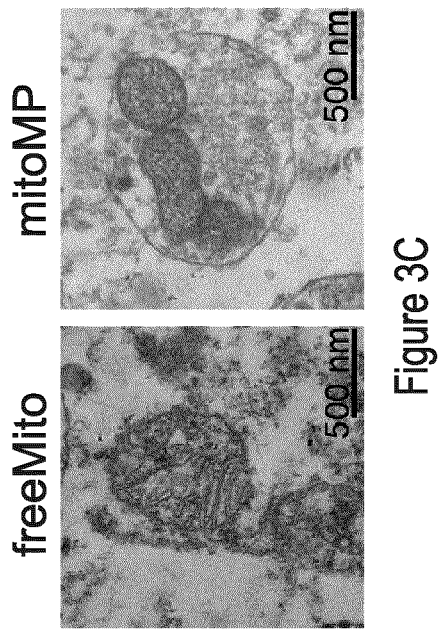
FIG. 3. Extracellular mitochondria are present in various situations where platelets are known to be activated. (A) Platelet mitoMPs (CD41$^+$MitoTracker1) are found in higher concentrations in the synovial fluid of rheumatoid arthritis (RA) patients (● n=20) than in the synovial fluid of osteoarthritis (OA) patients (■ n=14; data are mean±SEM, *P<0.05, Mann-Whitney test). (B) FreeMitos are detected in fresh synovial fluid (SF) of RA patients. Isolation of freeMitos in RA SF (from 3 different patients) with anti-TOM22 microbeads (or control IgG.
Figure 3B:
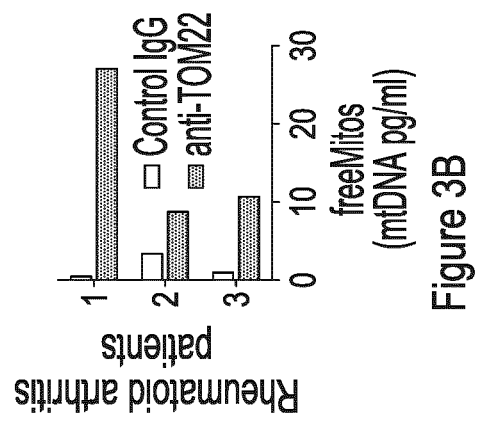
Figure 3C:
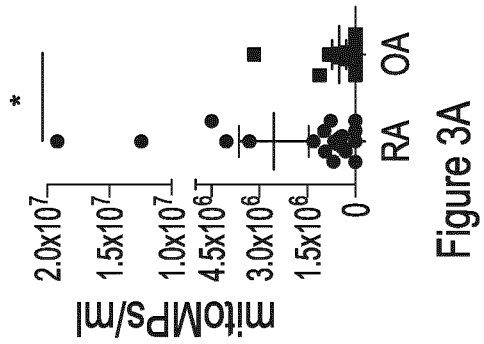
Figure 12A:
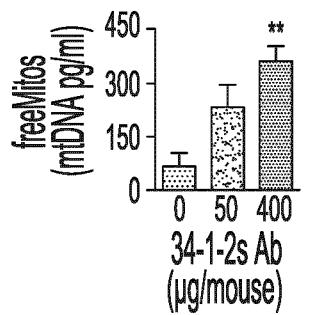
FIG. 12. Extracellular mitochondria are present in various sterile inflammatory pathologies. (A and B) A transfusion-related acute lung injury (TRALI) animal model was obtained by intravenous injection of the indicated concentration of 34-1-2s antibody in BALB/c mice. A significant temperature drop is observed in mice 1 h after antibody injection, correlating with an upsurge of freeMitos as measured by TOM22-mediated mtDNA isolation in bronchoalveolar lavages (n=3; data are mean±SEM, *P<0.05, **P<0.01 and #P<0.001 vs. control at 0 μg, t-test).
Figure 12B:
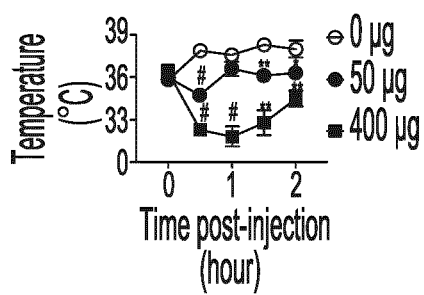

The broad diversity of stimuli capable of promoting concomitant release of mitochondria and MPs points to the biological relevance of this phenomenon. We thus sought to determine whether mitochondria are released in vivo in sterile inflammatory pathologies where platelet MPs are known to be produced. Using hs-FCM, anti-TOM22 coprecipitation of mtDNA, and TEM, we could detect significant levels of extracellular mitochondria in synovial fluid from patients with RA (FIG. 3A-C), consistent with the accumulation of platelet MPs and mtDNA reported in RA synovial fluid. In comparison, lower concentrations of extracellular mitochondria of platelet origin (CD41$^+$ mitoMPs) were measured in the synovial fluid of osteoarthritis patients (FIG. 3A), a joint disease in which platelet MPs are also less abundant. Similar observations were made in bronchoalveolar lavage fluids from an experimental murine model of transfusion-related acute lung injury (TRALI) (FIGS. 12A-B). Although the identified CD41$^+$ mitoMPs are very likely produced by platelets, damaged cells and activated mast cells are potential sources of freeMitos. We thus endeavored to confirm the platelet origin of extracellular mitochondria in a relevant biological context where platelets have been reported to release MPs ex vivo. Given their pivotal functions in hemostasis, platelet transfusion is frequently used to restore optimal platelet levels in thrombocytopenic patients. In contrast to red blood cell (RBC) concentrates, which are stored at ~4° C. for up to 42 days, platelet concentrates used for transfusion are stored at 20° C. to 24° C. Adverse reactions (febrile nonhemolytic reactions [fever or chills], anaphylaxis, transfusion-related sepsis, and TRALI) are more frequently observed with platelet than RBC transfusion. It is generally thought that this difference may be due to the presence of bacteria in platelet concentrates stored at permissive temperatures. From a phylogenetic standpoint, mitochondria are thought to have originated from the endosymbiosis of alphaproteobacteria (Rickettsiales) during the early evolution of eukaryotic cells. We hypothesized that extracellular mitochondria (organelles that are absent in RBCs) present in platelet concentrates might trigger adverse reactions similar to those observed with infectious agents.

We thus evaluated the presence of extracellular mitochondria in platelet concentrates used for human transfusion in the course of their storage. As measured using the $O_2$ consumption assay, as well as by TOM22 coprecipitation of mtDNA, hs-FCM, and TEM, we demonstrate significant levels of freeMitos and mitoMPs in platelet concentrates (FIGS. 3D-G). In keeping with the coupling of $O_2$ utilization and energy production, mitochondria present in MPs and free mitochondria in platelet concentrates display JC-1 dye aggregates, a cationic dye that accumulates in energized mitochondria (FIG. 3H). Most importantly, we established that platelet concentrates that had been associated with adverse transfusion reactions in human recipients contain higher concentrations of extracellular mitochondria (FIG. 3I). Thus, extracellular mitochondria, which have the alphaproteobacterium *Rickettsia prowazekii* as ancestor, are present in platelet concentrates used for transfusion, particularly in those that triggered transfusion-related reactions, and exhibit a significant degree of functionality.

Figure 4D:
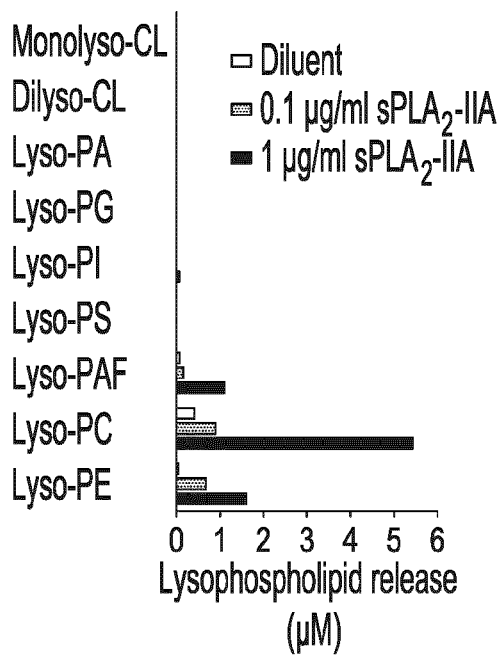
FIG. 4. The mitochondrion is a substrate for the bactericidal sPLA$_2$-IIA. (A) Quantification of sPLA$_2$-IIA in human platelets by time-resolved immunofluorescence (n=3; data are mean±SEM). (B) sPLA$_2$-IIA immunoblotting of mitochondria isolated with anti-TOM22 microbeads reveals binding of human recombinant sPLA2-IIA to mitochondria (FIG. 10). (C) Mitochondria were incubated in (left) the absence or (right) presence of Alexa488-conjugated sPLA$_2$-IIA and analyzed by hs-FCM. The significant shift in the fluorescent population size (right) indicates that sPLA2-IIA binds mitochondria. (D-E) Catalytic activity of human recombinant sPLA$_2$-IIA (or PBS as vehicle) toward mitochondria. Mitochondrial membrane phospholipid hydrolysis by sPLA$_2$-IIA yields (D) lysophospholipids and (E) fatty acids as quantified by mass spectrometry. (F) sPLA$_2$-IIA affects mitochondrial structural integrity. Scanning electronic micrographs of mitochondria incubated in the (left) absence or (right) presence of human recombinant sPLA$_2$-IIA. (G) Mitochondria release mtDNA on incubation with recombinant sPLA$_2$-IIA (upper panels). Extracellular mtDNA accumulation (arrow) is apparent in the presence of sPLA$_2$-IIA. Differential interference contrast images are shown for reference (lower panels). (H) mtDNA extrusion is amplified in the presence of human recombinant sPLA$_2$-IIA (0.2 mg/mL, 30 minutes at 37° C.), as quantified by Sytox Green nucleic acid stain assay (n=6; data are mean±SEM, *P<0.05, t test).

What are the implications of the release of free mitochondria by platelets? Extracellular mitochondria are already well-recognized as highly potent damage-associated molecular patterns (DAMPs), capable of mediating inflammation locally and systemically through their bacteria-like components (i.e., N-formylated peptides and mtDNA). In this study, we aimed to identify unprecedented roles for extracellular mitochondria in inflammation. The sPLA$_2$-IIA, initially identified in platelet and abundantly present in this cellular lineage (FIG. 4A), hydrolyzes the sn-2 acyl bond of glycerophospholipids, resulting in the release of free fatty acids and lysophospholipids. sPLA$_2$-IIA is found in plasma and is induced in chronic and acute inflammatory conditions. Although the promotion of host defense via bacterial membrane hydrolysis is an established function for this enzyme, sPLA$_2$-IIA is only poorly active toward the plasma membrane of eukaryotic cells, including platelets, and its endogenous substrate in sterile inflammation has thus far remained unclear.

Figure 4E:
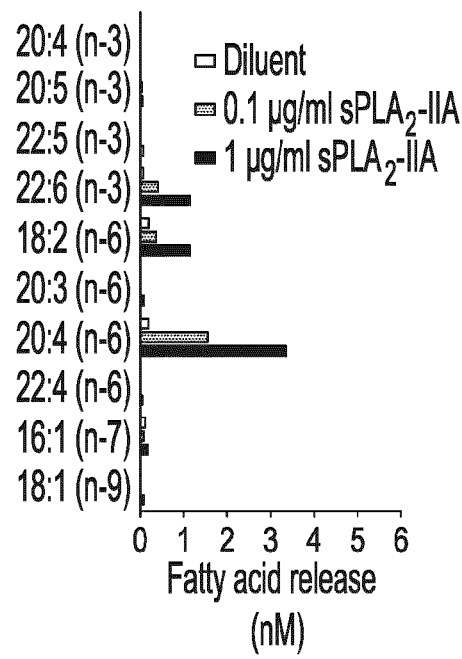
Figure 4F:
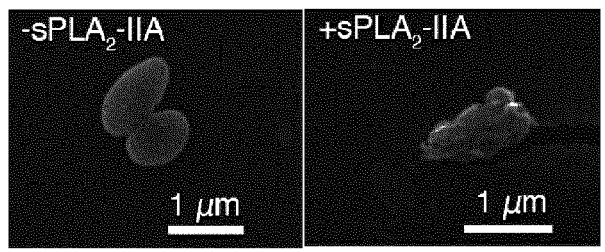
Figure 4G:
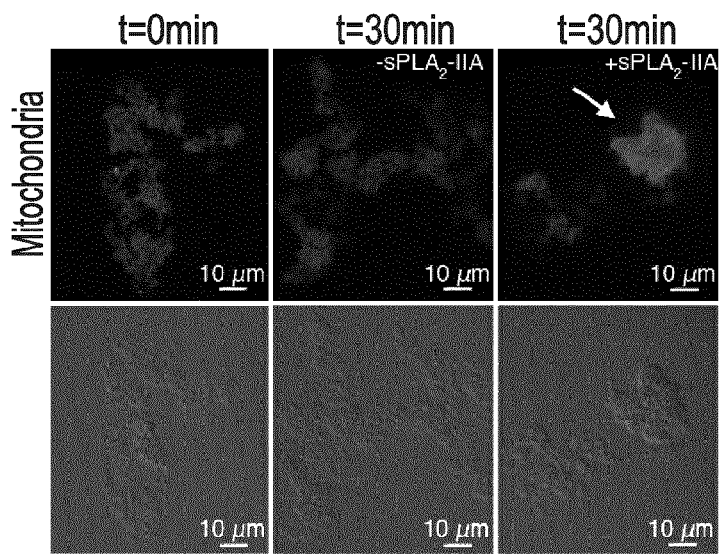
Figure 4H:
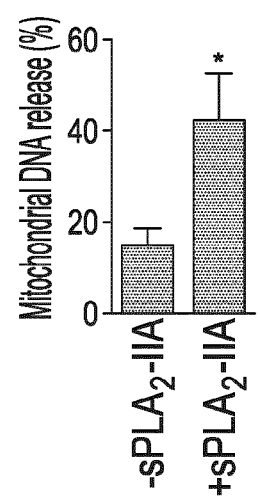

The ancestral similarities between bacteria and mitochondria prompted us to examine whether the mitochondrial membrane is susceptible to hydrolysis by sPLA$_2$-IIA. We observed that sPLA$_2$-IIA binds mitochondria (FIGS. 4B-C), leading to the release of various lysophospholipids and free fatty acids (FIGS. 4D-E), and in doing so, severely affects mitochondrial structural integrity (FIG. 4F). Similarly to bacteria, the mitochondrial genome is rich in unmethylated CpG motifs, a recognized DAMP and a cellular degradation product that is found outside cells in multiple disorders. To determine whether mitochondrial digestion by sPLA$_2$-IIA might lead to mtDNA release, we used confocal microscopy and an assay specifically designed to quantify soluble DNA. With this combination of approaches, we identified sPLA$_2$-IIA as an enzyme capable of promoting the release of mtDNA (FIGS. 4G-H). Thus, the mitochondrion is an endogenous substrate of sPLA$_2$-IIA, and its hydrolysis leads to the generation of recognized proinflammatory signals (arachidonic acid, lysophospholipids, and mtDNA). Furthermore, this result raises the possibility that a previously unrecognized function of sPLA$_2$-IIA is to assist in the degradation of freeMitos released by platelets and potentially other cells.

Figure 5B:
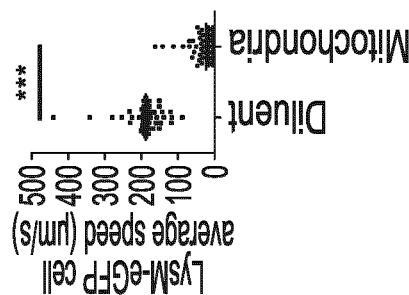
FIG. 5. Extracellular mitochondria interact with neutrophils. (A) Intravenously injected fluorescence-labeled mitochondria (MitoTracker Deep Red™) associate with mouse neutrophils (Gr11 cells) in vivo as measured by flow cytometry (n=6; data are mean±SEM, *P<0.001, t test). (B) Intravenous injection of mitochondria induces neutrophil rolling in LysM-eGFP mice. (Center and right) Neutrophil velocity is significantly reduced (n=89; and data not shown) in blood following intravenous injection of mitochondria compared with (left) Tyrode buffer as vehicle (n=51; data are mean±SEM, *P<0.001, t test) (C) Scanning electronic micrographs of mitochondria in association with (left) freshly isolated human neutrophil and (right) ensuing neutrophil structural change (29.2±2.11%, n=3) after a 30-minute incubation in the presence of human recombinant sPLA$_2$-IIA.
Figure 5B:
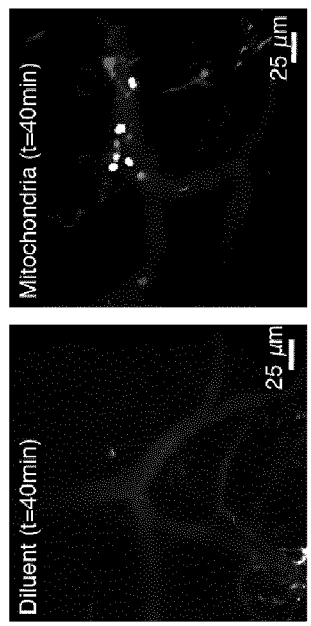
Figure 5C:
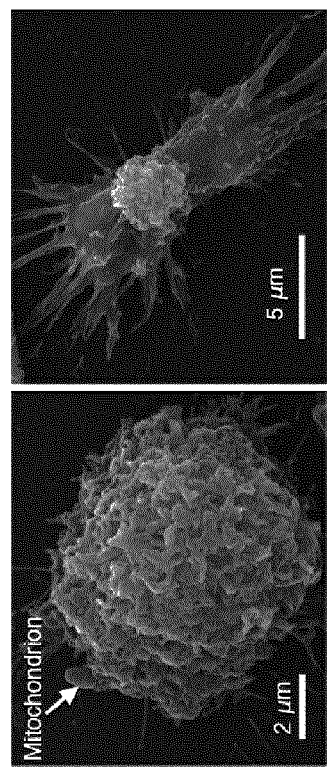
Figure 5A:
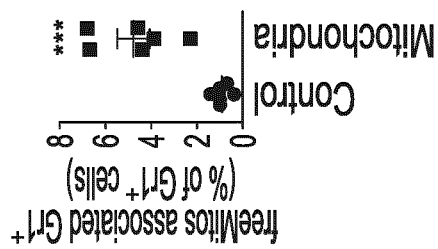

We next endeavored to identify a relevant cellular lineage that may be regulated by extracellular mitochondria. We found that fluorescent mitochondria intravenously injected into mice associate with neutrophils, a polymorphonuclear leukocyte cell lineage that plays key roles in inflammation (FIG. 5A). Intravital investigations in mice using 2-photon microscopy demonstrated that extracellular mitochondria present in the bloodstream prompt neutrophil interactions with the vascular wall and rolling (FIG. 5B; and data not shown). Using qualitative scanning electron microscopy, we found that extracellular mitochondria consistently induce human neutrophils to display striking ultrastructural features, similar to pseudopodia (FIG. 5C). Together, these observations suggest that extracellular mitochondria can interact with neutrophils, thereby modulating their activities.

Figure 6B:
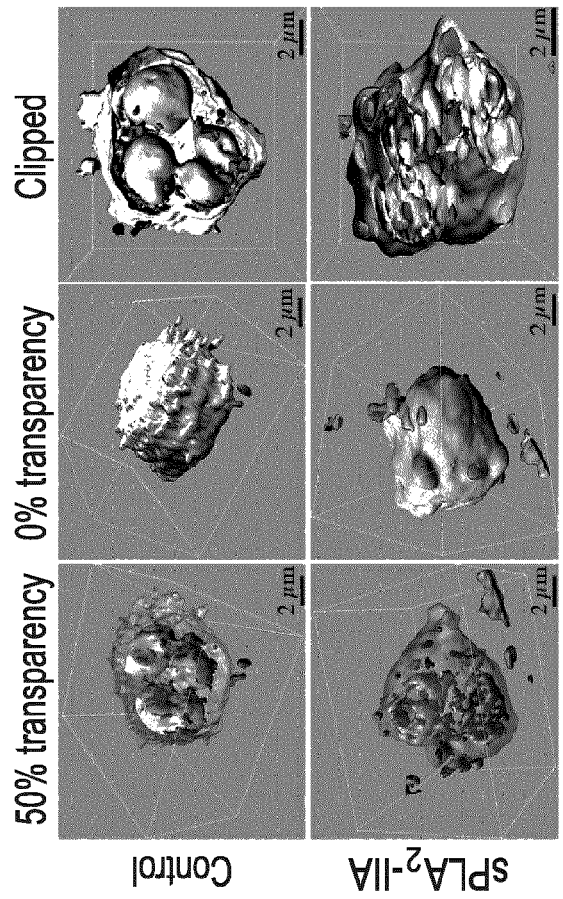
FIG. 6. Interaction of human neutrophils with the mitochondria/sPLA$_2$-IIA complex promotes the release of proinflammatory mediators. (A) Human neutrophils associate with the mitochondria/sPLA2-IIA complex in vitro as measured by flow cytometry analysis of human neutrophils incubated with fluorescently labeled mitochondria (MitoTracker Deep Red™) in the (left) absence or (right) presence of Alexa488-conjugated sPLA$_2$-IIA. (B) Three-dimensional CSLM reconstruction of mitochondria and Q:8 sPLA$_2$-IIA colocalizing within neutrophils. (C) Mitochondria are internalized in human neutrophils via an endocytosis-dependent pathway. Graph bars representation of the relative localization (surface vs. intracellular) of the mitochondria inside neutrophils following pretreatment with indicated inhibitors (nystatin for inhibition of caveolin-mediated endocytosis; chlorpromazine for inhibition of clathrin-mediated endocytosis; dynasore for inhibition of dynamin-mediated endocytosis; nocodazole for inhibition of polymerization of microtubule [endocytosis and phagocytosis]; cytochalasin B for inhibition of polymerization of actin [endocytosis and phagocytosis]). Data were obtained from 100 neutrophils per condition repeated 3 times (n=3, *P<0.01, P<0.001, and *P<0.0001, Mann-Whitney test compared with diluent). (D) Mitochondrial hydrolytic products derived from the action of the mitochondria/sPLA$_2$-IIA complex (FIG. 4D-E) induce proinflammatory responses in human neutrophils. The total 5-lipoxygenase products (5-LO products) were quantified by high-performance liquid chromatography (n=4; data are mean±SEM, **P<0.005 vs control, t test). (E) The freeMito fraction induces NET formation in vitro and is enhanced by sPLA$_2$-IIA. NET formation (left panel) was confirmed by confocal imaging after treatment of mitochondria (right panel) with sPLA$_2$-IIA. sPLA$_2$-IIA significantly enhances NET formation by mitochondria (upper right panel, n≥7; data are mean±SEM, *P<0.05 and P<0.005, t test). Hydrolysis products from mitochondria/sPLA$_2$-IIA complex activity also induce significant NET formation (lower right panel, n≥3; data are mean±SEM, P<0.005 and ***P<0.001, t test).
Figure 6A:
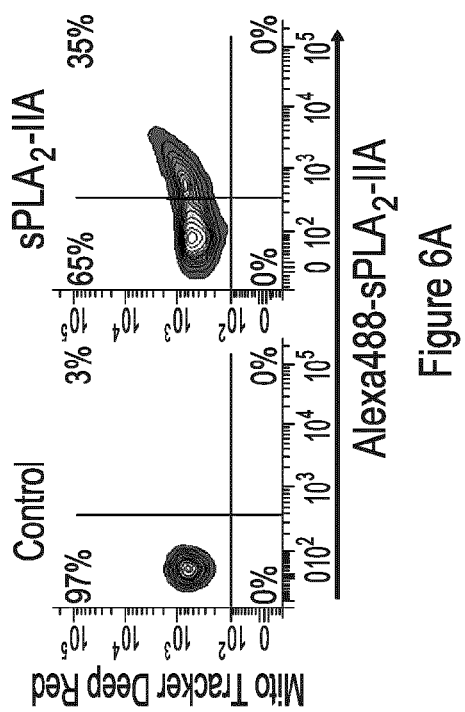
Figure 13:
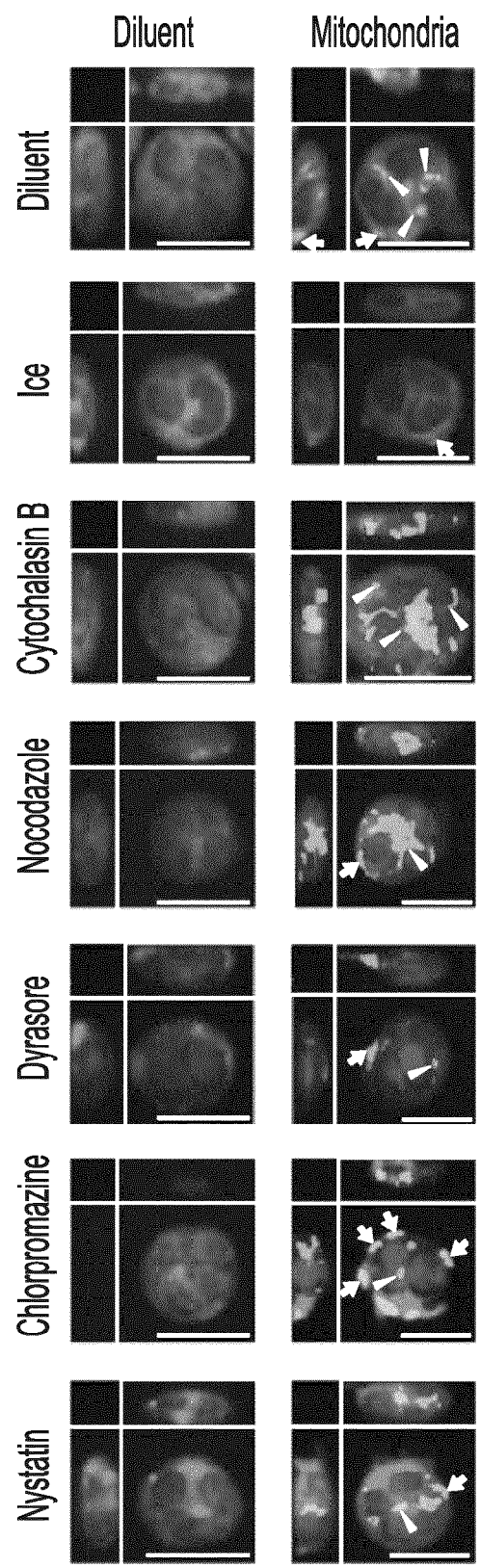
FIG. 13. Exogenous mitochondria are internalized via an endocytosis-dependent pathway by human neutrophils. Representative confocal microscopy analyses of neutrophils cytoplasm and nuclei incubated with exogenous mitochondria (cyan) for 30 min at 37° C. To assess passive internalization (ice condition), exogenous mitochondria and neutrophils were incubated on ice for 30 min. Neutrophils were pre-treated with either cytochalasin B, nocodazol, dynasore, nystatin, or chlorpromazine for 10 min at 37° C. Cells were then incubated for 30 min at 37° C. in the presence of 5×10$^5$ mitochondria/μl (labeled with 100 nM final of MitoTracker® Deep Red, Invitrogen) and recombinant human sPLA2-IIA (0.2 μg/ml). Scale bars represent 10 μm. Data are representative of three independent experiments.
Figure 14:
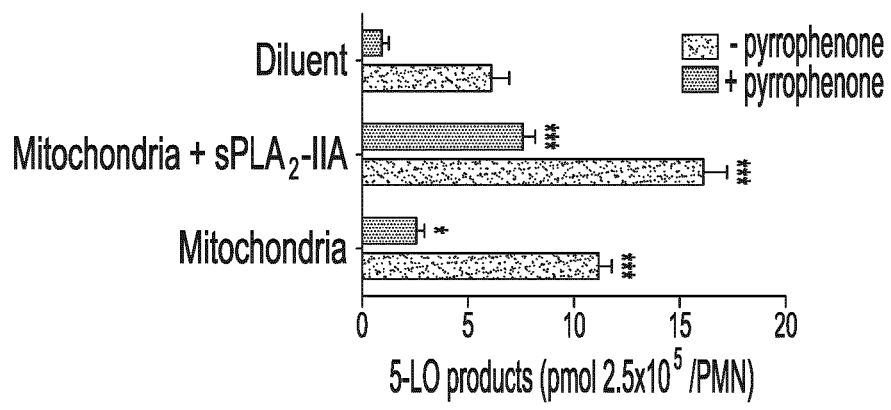
FIG. 14. sPLA$_2$-IIA and cPLA$_2$-α work in concert to promote generation of 5-lipoxygenase products in human neutrophils. Human neutrophils pretreated with the cPLA$_2$-α inhibitor pyrrophenone (or diluent) were incubated in the presence of exogenous mitochondria and mitochondria/sPLA$_2$-IIA complex. Proinflammatory lipid mediators release was then evaluated. The total 5-lipoxygenase products (5-LO products) were quantified by high-performance liquid chromatography (n=6; data are mean±SEM, *P<0.05 and ***P<0.001 vs. control, t-test).

To address the possibility that the combination of sPLA$_2$-IIA and mitochondria might trigger activities other than those induced by either mitochondria or sPLA$_2$-IIA alone, we assessed whether sPLA$_2$-IIA and extracellular mitochondria could associate together with neutrophils. Interestingly, fluorescent sPLA$_2$-IIA and exogenously labeled mitochondria rapidly associate with human neutrophils and colocalize intracellularly (FIGS. 6A-B) through dynamin, clathrin, and caveolin-dependant endocytosis (FIG. 6C; FIG. 13). Arachidonic acid (20:4, n-6) derived from sPLA$_2$-IIA enzymatic activity may contribute to the biosynthesis of inflammatory eicosanoids such as leukotrienes by neighboring leukocytes. To determine whether the association of mitochondria, sPLA$_2$-IIA, and neutrophils might promote cell activation, we measured the release of leukotriene B4 (LTB4) by neutrophils. We found that neutrophils produce copious amounts of LTB4 when both extracellular mitochondria and sPLA$_2$-IIA are present (FIG. 6D). Importantly, such LTB4 production is strictly dependent on sPLA$_2$-IIA catalytic activity as it takes place even in presence of the cPLA2α inhibitor pyrrophenone, and is not observed when a catalytically inactive sPLA$^2$-IIA mutant form is used (FIG. 6D; FIG. 14).

Platelets are implicated in the activation of neutrophils and participate in the formation of neutrophil extracellular traps (NETs), a recognized feature found in RA and transfusion adverse reactions like TRALI. Interestingly, freeMitos are also NET inducers, a phenomenon that is amplified in the presence of sPLA$_2$-IIA (FIG. 6E). Consistent with their recognized proinflammatory potency, the different hydrolytic products derived from sPLA$_2$-IIA activity (arachidonic acid, lysophospholipids, and mtDNA) are all highly potent at inducing NETosis (FIG. 6E). Thus, the sPLA$_2$-IIA/mitochondria complex associates with neutrophils and promotes cellular activation that is dependent on sPLA$_2$-IIA activity.

Figure 7D:
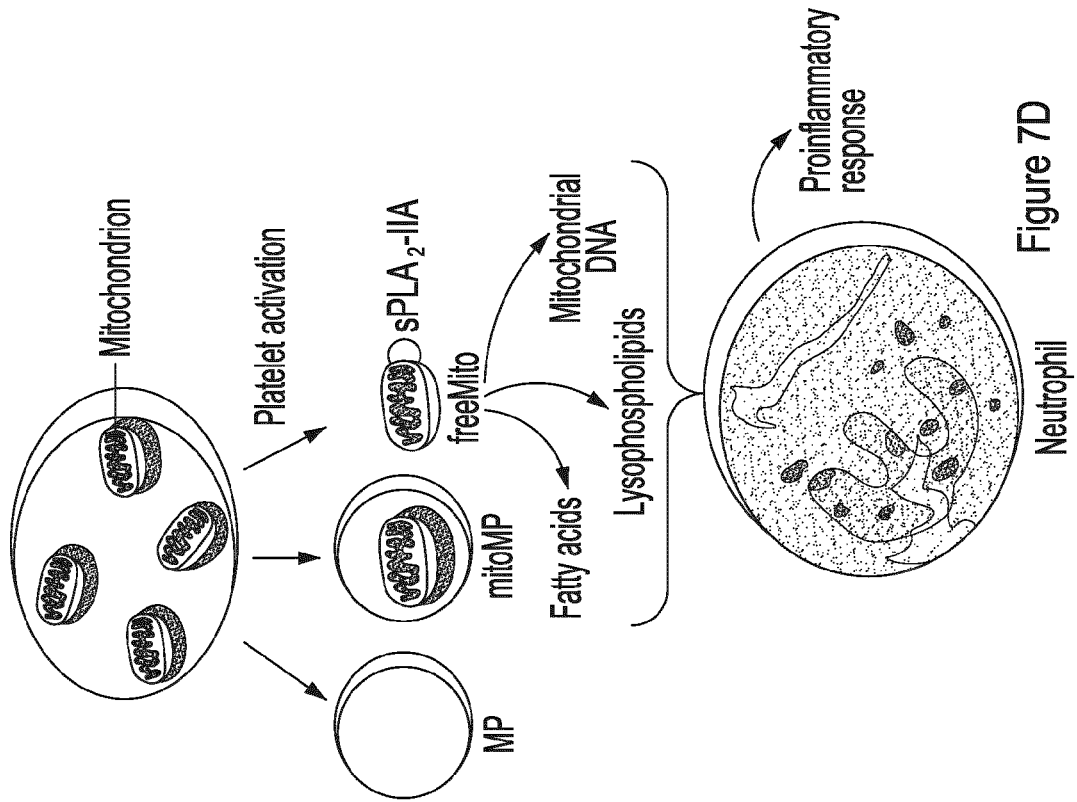
FIG. 7. Extracellular mitochondria and sPLA$_2$-IIA amplify inflammation in vivo. (A) Intravenous injection of mitochondrial hydrolytic products (sPLA$_2$-IIA-treated mitochondria, ▲) in sPLA$_2$-IIA-deficient mice significantly lowers body temperature (Δ temperature vs PBS-injected mice of respective background) after 4 hours (n=6/group; data are mean±SEM, P<0.005 compared with sPLA$_2$-IIA-untreated mitochondria [■] or sPLA2-IIA alone [●]). Intravenous injection of mitochondria (sPLA$_2$-IIA untreated, □) in sPLA$_2$-IIA-sufficient mice significantly lowers body temperature after 24 hours. Only a modest temperature decrease was observed in sPLA$_2$-IIA-untreated mitochondria in sPLA$_2$-IIA-deficient mice (n≥3/group; data are mean±SEM, P<0.005). (B) sPLA2-IIA-generated mitochondrial products trigger inflammation in vivo. Mitochondria incubated in the presence of recombinant sPLA$_2$-IIA and injected into the air pouch of C57BL/6N mice induce the production of (left) IL-1b and (right) IL-6. Diluent (PBS), sPLA$_2$-IIA alone, or untreated mitochondria induce modest cytokine production when injected separately (n=7; data are mean±SEM, **P<0.005 compared with mitochondria incubated in the absence of sPLA$_2$-IIA). (C) Mitochondria accumulation in the liver induces numerous proinflammatory genes that are amplified in the presence of endogenous sPLA$_2$-IIA. mRNA expression of inflammatory genes relevant to neutrophil function was quantified in the liver of sPLA$_2$-IIA-sufficient and -deficient mice intravenously injected with mitochondria (n=3 per group; data expressed as the ratio of specific mRNA expression ratio (sPLA$_2$-IIA sufficient/deficient mice)). (D) Schematic representation of the mechanism of action of extracellular mitochondria and sPLA$_2$-IIA in sterile inflammatory conditions. On activation, platelets release MPs, mitoMPs, and freeMitos. Mitochondrial membrane phospholipids may be hydrolyzed by sPLA$_2$-IIA, generating bioactive mediators (fatty acids, lysophospholipids, and mtDNA) and promoting neutrophil proinflammatory responses.
Figure 7C:
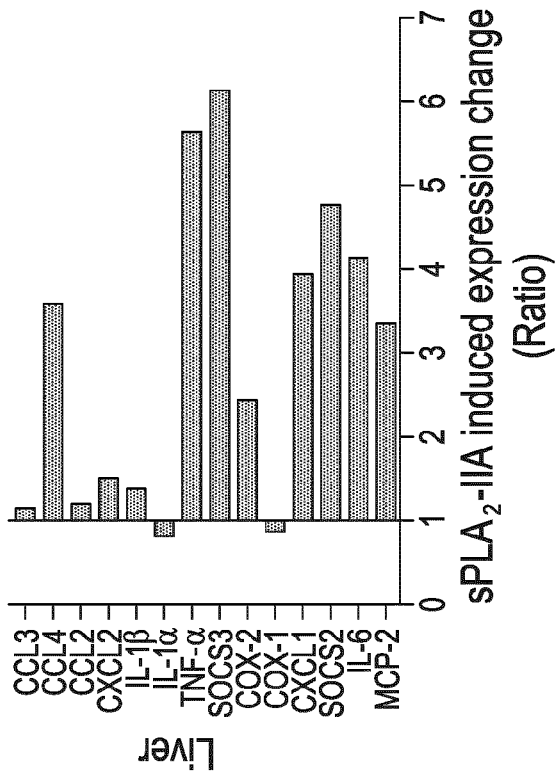
Figure 15A:
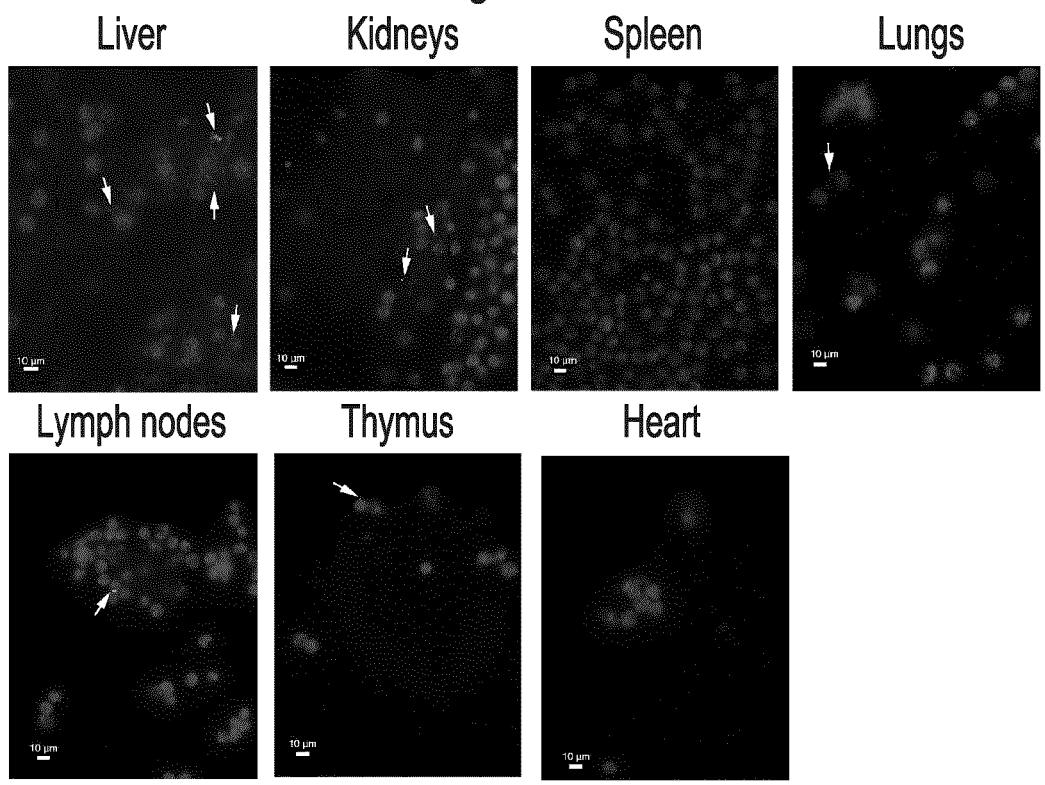
FIG. 15. Localization of extracellular mitochondria following their intravenous injection. (A) Mitochondria (white arrow) are found primarily in liver, kidneys, lymph nodes and lungs (Hoechst stain) of C57BL/6N mice. (B) Organ distribution of human sPLA$_2$-IIA mRNA expression in sPLA$_2$-IIA sufficient mice. sPLA$_2$-IIA mRNA was detected in lungs, kidneys and liver of sPLA$_2$-IIA sufficient mice. Relative fold increase of sPLA$_2$-IIA expression was obtained when comparing sPLA$_2$-IIA expression in lungs and liver compared to the level found in kidneys. sPLA$_2$-IIA is predominantly expressed in the liver of sPLA$_2$-IIA sufficient mice (n=3 for each phenotype).
Figure 15B:
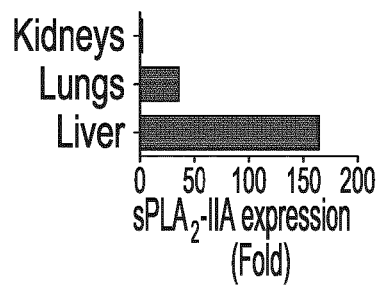

We next examined the significance of this pathway in the inflammatory response in vivo. In this set of experiments, we used C57BL/6J mice (which naturally lack sPLA$_2$-IIA) to evaluate whether mitochondrial hydrolytic products are active. Consistent with our in vitro observations, we found that the products derived from freeMitos via human recombinant sPLA$_2$-IIA activity promote a rapid, significant decrease in body temperature (FIG. 7A) and induce proinflammatory cytokine release when injected into sPLA$_2$-IIA-deficient mice (FIG. 7B). Conversely, intact freeMitos injected in these mice elicited only a modest response, confirming that freeMitos can trigger an inflammatory response that is dependent on hydrolysis by sPLA$_2$-IIA. To determine whether endogenous sPLA$_2$-IIA can produce mediators from freeMitos in vivo, we examined the effect of intact freeMitos injected in transgenic C57BL/6J mice expressing sPLA$_2$-IIA. Interestingly, we found that the latter treatment induced a delayed but albeit significant lowering of body temperature (FIG. 7A), suggesting that the endogenous sPLA$_2$-IIA expression is sufficient to promote inflammatory reactions. To determine whether freeMitos can modulate physiological processes in discrete organs, we evaluated their localization on injection via tail vein. We observed that the bulk of injected freeMitos accumulate in the liver, kidney, lungs, and lymph nodes (FIG. 15A). Consistent with the concomitant localization of sPLA$_2$-IIA (FIG. 15B) and neutrophils in the liver, freeMito accumulation in this organ triggers the expression of a broad variety of proinflammatory genes recognized as relevant to neutrophil functions (FIG. 7C). Our observations demonstrate that the combined activity of extracellular mitochondria and sPLA$_2$-IIA generates inflammatory signals in vivo.

Mitochondrial components secreted from cells might act as autopathogens. Owing to their numerous similarities to bacteria, extracellular mitochondria can stimulate the immune system and thereby trigger inflammation. Indeed, cell-free mtDNA levels are increased in blood in several pathologies and can be used as a potent biomarker. Our study establishes that platelets can release functional mitochondria (free or shuttled via MPs), which can be transferred to other cells such as neutrophils.

Figures 16A, 16B:
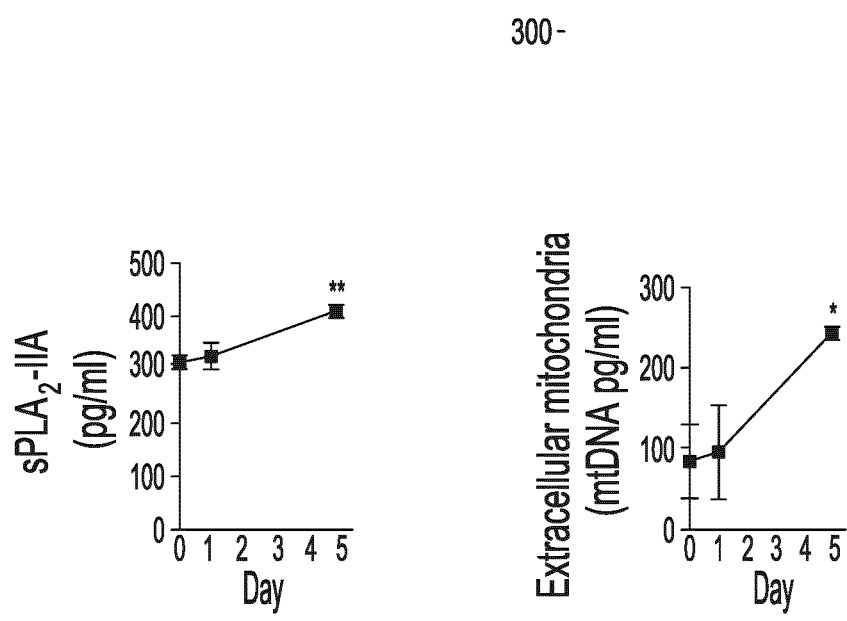
FIG. 16. sPLA$_2$-IIA and mtDNA levels increase in platelet concentrates during storage. Platelet storage bags (n=6) were incubated for the indicated time at 22° C. with constant agitation. PFP samples were obtained on days 0, 1 and 5 for the following analyses: (A) quantification of sPLA$_2$-IIA by time-resolved immunofluorescence (n=3; data are mean±SEM, t-test); (B) extracellular mtDNA abundance by quantitative PCR (n=3; data are mean±SEM, *P<0.05, **P<0.01, t-test).

The concentration of sPLA$_2$-IIA is increased in inflammatory exudates, such as in the plasma of septic shock patients and RA synovial fluid. Consistent with this observation, the sPLA$_2$-IIA-expressing transgenic mice used in our study display higher levels of plasma sPLA$_2$-IIA and develop accelerated blood vessel inflammation and autoimmune arthritis. Although sPLA$_2$-IIA is a bactericidal enzyme that has been studied for decades, its endogenous substrates in sterile inflammation were thought to be limited to dying cells and MPs. Our study identifies mitochondria as an overlooked source of biologically active mediators that can be released via sPLA$_2$-IIA enzymatic activity. In addition to arachidonic acid conversion to eicosanoids, other lipid mediators may also promote inflammation (FIG. 7D). Lysophospholipids are released through sPLA$_2$-IIA activity toward the mitochondrial membrane and can trigger inflammation. In the context of platelet transfusion, lysophospholipid levels accumulate in platelet concentrates during storage and promote adverse effects. It is thus highly plausible that these lysophospholipids are in fact derived from sPLA$_2$-IIA activity, which is also abundant in platelet concentrates (FIG. 16A), toward extracellular mitochondria. Beyond the release of lipid mediators, sPLA$_2$-IIA also participates in the extrusion of mtDNA (FIGS. 4F-H). This process may occur in an inflammatory microenvironment where sPLA$_2$-IIA and freeMitos (originating from platelets, mitoMPs, or other activated/damaged cell lineages) are both present, such as in RA, as well as in the context of transfusion. Indeed, soluble mtDNA concentrations in platelet storage bags increase concomitantly with sPLA2-IIA levels (FIGS. 16A-B) and are higher in concentrates associated with adverse transfusion reactions (FIG. 3I). The observation that intravenous injection of mtDNA triggers lung inflammation might provide insight into how platelet transfusions induce lung injury.

Mitochondrial components that are not dependent on sPLA$_2$-IIA activity might also contribute to the promotion of inflammation. Respiratory competence displayed by platelet-derived mitochondria implies an increased production of ATP, a recognized DAMP, as well as an upsurge in extracellular reactive oxygen species, which are known danger signals. Similar to bacteria, mitochondria express N-formylated peptides that can recruit leukocytes to the site(s) of inflammation. The presence of these different inflammatory components, whose production does not require sPLA$_2$-IIA, might explain how intravenous injection of mitochondria induce neutrophil rolling along the vascular wall (FIG. 5B; and data not shown), which is typically reminiscent of neutrophil priming, and how intact mitochondria might induce significant NETosis (FIG. 6E).

Although we focused our study on innate and acute inflammatory responses triggered by extracellular mitochondria, the latter may also be involved in adaptive immune responses and chronic inflammation. Indeed, the generation of antibodies directed against mitochondrial components may occur in chronic rheumatic diseases in which mitochondria are constantly being liberated released by activated platelets, as well as and in transfused patients repeatedly transfused with who end up receiving substantial doses of extracellular mitochondria. Interestingly, cardiolipin, a phospholipid uniquely expressed by mitochondria (and bacteria), may also be also highly antigenic, thus providing an explanation for the prevalence of anticardiolipin in rheumatic diseases, and in pathologies implicating involving platelets such as systemic lupus erythematosus and antiphospholipid syndrome.

Platelet activation under flow conditions induces the formation of long tubes, called flow-induced protrusions. Furthermore, and the plasma of healthy subjects contains tubular extracellular vesicles. We thus foresee that these tubular structures might also express mitochondria. Keeping in mind that platelets rapidly respond to vascular injuries to prevent bleeding, and that mitochondria might also be released in this context, we further speculate that extracellular mitochondria could contribute to the hemostatic functions of platelets. Like MPs, mitochondria might serve to for tissue factor deposition and to for the initiation of the coagulation cascade, which is by itself in a sense a well-controlled inflammatory reaction. Subsequent studies will undoubtedly uncover additional physiological role(s) played by extracellular mitochondria.

Platelets are classically considered first and foremost as key players in hemostasis. However, mounting evidence suggests that these cells actively participate in inflammation. The identification of mitochondria, with and their bacterial ancestry, and of a bactericidal phospholipase A2, sPLA2-IIA, as entities that are released from platelets and that work together in many inflammatory disorders, suggests that they both may both be key mediators in sterile inflammatory conditions.

Example III—Characterization of Mitochondria from Platelets in Lupus

The material an methods used in this Example are provided in Example I.

We verified the presence of mitochondrial immune complexes in the plasma of 192 patients from the established University of Toronto Lupus Clinic (Table 2).

Table 2. Demographics and disease characteristics of the 192 women that participated in the study of fatty acids in lupus. We have recruited and characterized 192 women with lupus from the University of Toronto Lupus Clinic. This longitudinal observational study includes more than 1 600 persons with SLE that are followed prospectively according to a standardized protocol. We recruited 192 consecutive female patients with SLE and collected demographic variables and disease characteristics as well as serum and plasma. Baseline demographic variables and disease characteristics of these 192 women demonstrate that this is a sample of middle-aged women (mean age (SD)=46.3 years (14.7)) with a long average disease duration of 18 years and low disease activity on the systemic lupus erythematosus disease activity index (SLEDAI), but significant cumulative damage on the Systemic Lupus International Collaborating Clinics (SLICC) damage index.

TABLE 2

Demographics and disease characteristics of the 192 women that participated in the lupus study

| | Women with SLE N = 192 |
|---|---|
| DEMOGRAPHICS (N = 192) | N (%) unless specified |
| Female | 192 (100) |
| Mean age (mean ± sd) | 46.27 ± 14.7 |
| Marital status (married/common law) | 107 (56) |
| Education (completed college or higher) | 133 (69) |
| Employment (working) | 79 (41) |
| Race | |
| Caucasian | 110 (57) |
| Asian | 39 (20) |
| Black | 33 (17) |
| Chinese | 10 (6) |
| Other | |
| Menopausal status (post-menopausal) | 106 (55) |
| Body mass index (BMI) | |
| Obese (BMI >30) | 33 (17) |
| Overweight (BMI >= 25 to <30) | 48 (25) |

TABLE 2-continued

Demographics and disease characteristics of the 192 women that participated in the lupus study

| | Women with SLE N = 192 |
|---|---|
| Normal (BMI >= 18.5 to <25) | 100 (52) |
| Underweight (BMI <18.5) | 11 (6) |
| Smoking | |
| Current | 18 (9) |
| Past | 43 (23) |
| Never | 131 (68) |
| Hypertension | 58 (30) |
| Diabetes mellitus | 10 (5) |
| Medication use | |
| Antimalarial drugs | 142 (74) |
| Antiplatelet or anticoagulant | 48 (25) |
| Lipid lowering drug | 30 (16) |
| Prednisone | 85 (44) |
| Average dose (mg/day) (mean ± sd) | 11.4 ± 22.4 |
| DISEASE CHARACTERISTICS (N = 191) | (mean ± sd) unless specified |
| Disease duration (mean ± sd) | 18.5 ± 12.0 |
| Disease activity by SLEDAI | 2.7 ± 10.7 |
| Disease damage by SLICC DI (SDI) | 1.7 ± 3.1 |

Figure 17C:
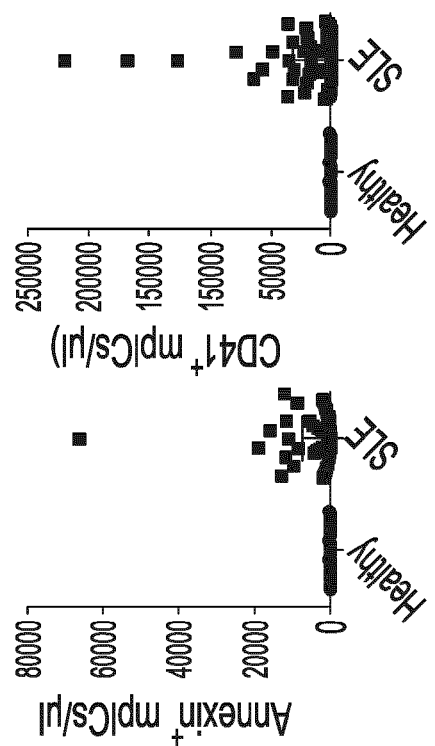
FIG. 17. Platelet MP subtypes in SLE. (A) Hypothetical pathway leading to mitochondria immunization and platelet activation in the course of disease amplification in SLE. Platelets can be coated with IgG via the recognition of surface antigens or the interaction of IgG with the Fc receptor FcγRIIA. Platelet activation, mediated by ICs or other stimuli relevant to SLE such as vascular injury, generates MPs, mitoMPs and freeMitos. Extracellular mitochondria regroup mitoMPs and freeMitos. The release of mitochondria triggers immunization against mitochondrial antigens (cardiolipins and DNA for example). All of the MP subtypes may further interact with IgG, generating mpICs, mitompICs and freemitoICs. These MP subtypes composed of ICs, like the freemitoICs, can further activate platelets through FcγRIIA, promoting the generation of a powerful activation loop. (B) Visualization of the mpICs in SLE plasma using electron microscopy using protein A-conjugated gold nanoparticles (10 nm) and Annexin-V-conjugated gold nanoparticles (4 nm) to visualize ICs and phosphatidylserine-exposing MPs, respectively. Representative observations obtained using one SLE plasma. White arrows indicate the edge of one AnnexinV$^+$ MPs and black arrows indicate ICs. (C) Quantification of the Annexin-V$^+$ mpICs (left panel) and CD41$^+$ mpICs (both the Annexin-V$^+$ and Annexin-V) (right panel) contained in the plasma of healthy subjects (n=20) and SLE patients (n=193); P<0.0001. (D) The inclusion of TOM22 antibody discriminates freeMitos from mitoMPs. The supernatants from activated platelets were incubated with fluochrome-conjugated anti-CD41, mitotracker and anti-TOM22. Platelet mitoMPs (CD41$^+$ mitotracker$^+$) are negative for TOM22, a surface marker for mitochondria. Conversely, FreeMitos (CD41$^-$ mitotracker$^+$) show positivity for anti-TOM22 antibodies. Representative of 5 independent experiments. (E) Quantification of extracellular mitochondria contained in platelet (CD41$^+$) MPs (mitoMPs) associated with ICs in healthy and SLE subjects using hs-FCM (n=10/group, *P<0.0001). (F) Quantification of extracellular mitochondria contained in platelet (CD41$^+$ CD61$^+$) MPs (mitoMPs) in a subset of healthy and SLE subjects using hs-FCM (n=3 healthy and 7 SLE/group). (G) Quantification of free mitochondria (mitotracker$^+$, CD41$^-$ and showing reactivity for anti-TOM22 antibody) associated with ICs in healthy and SLE subjects using hs-FCM (n=10/group, *P<0.0001). (H) MPs that harbor platelet marker CD41 can be visualized using EM. Gold nanospheres (4 nm) were conjugated to anti-CD41 antibodies and incubated with platelet MPs.
Figure 17B:
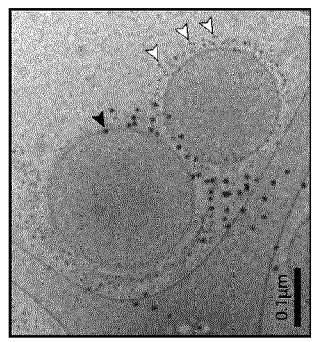
Figure 17A:
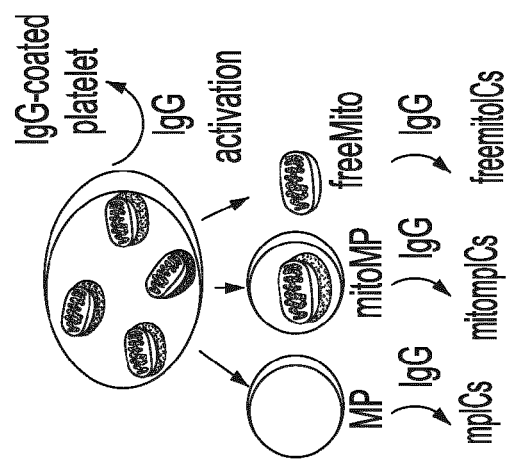
Figure 17D:
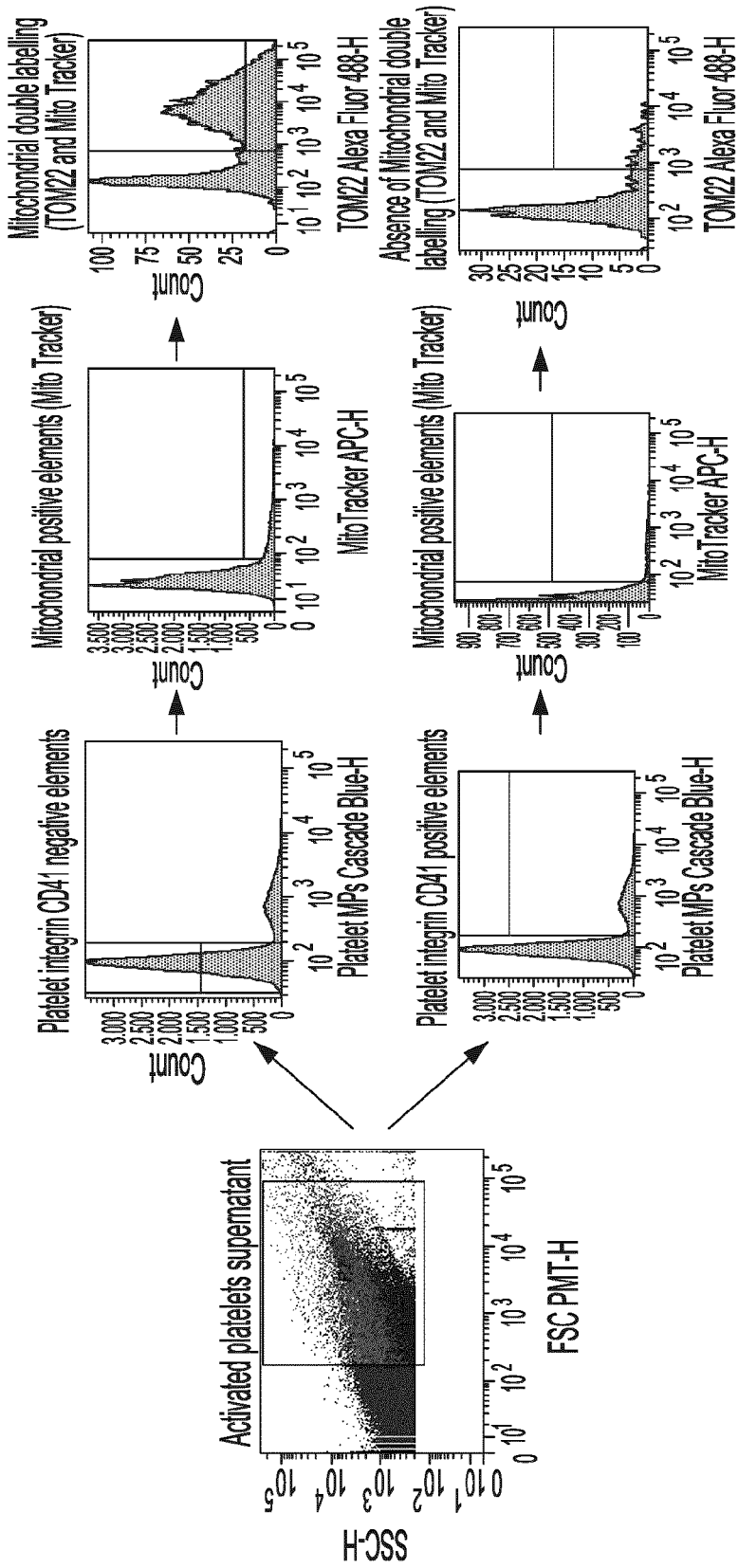
Figure 17H:
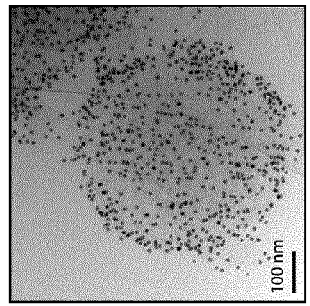
Figure 17G:
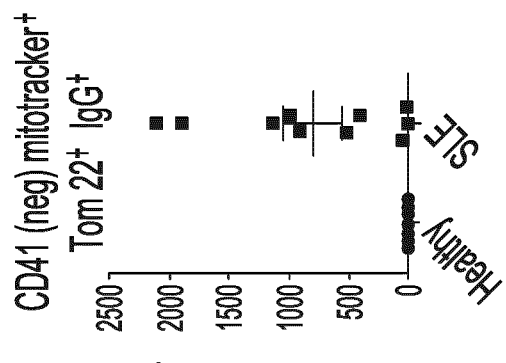
Figure 17F:
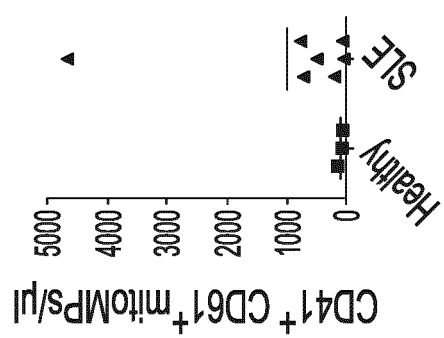
Figure 17E:
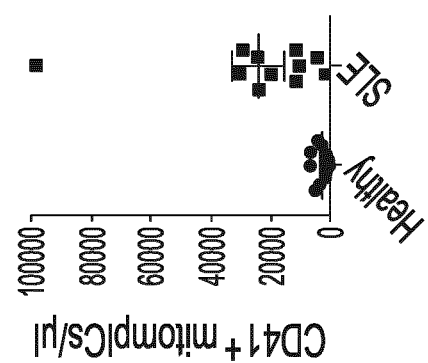

Using annexin-V and protein A conjugated to gold nanospheres to respectively visualize phosphatidylserine (PS) and MPs decorated with immunoglobulin G (IgG) antibodies (also referred as microparticle-associated immune complexes, or mpICs), we established the presence of mitochondrial particles immune complexes (mpICs) in SLE plasma (FIG. 17B).

We next used hs-FCM to survey a larger number of samples. Healthy historical age- and gender-matched control subjects (n=20 plasma) were used for comparison. Platelet-free plasma (10 μl) was incubated with Cy5-conjugated F(ab')2 goat anti-human IgG (anti-IgG-Cy5) (Jackson), PE-anti-human CD41 (M148) (anti-CD41-PE) (Abcam); and FITC- or V450-conjugated annexin-V (BD). Each of these fluorescent markers was read by a distinct laser on the hs-FCM, permitting optimal specificity. The corresponding isotype antibodies were used as controls, and the membrane moiety of the MPs was assessed using a reported detergent protocol (Cloutier et al. 2012, Gyorgy et al. 2011, Gyorgy et al. 2012). We use a forward scatter (FSC) "small particles option" coupled to a photomultiplier tube (PMT) (FSC-PMT) (rather than the usual diode) (van der Vlist et al. 2012), and a 100 mW blue laser (rather than the usual 20 mW), all mounted on the FACS Canto II Special Order Research Product (BD Biosciences). We confirmed the presence of annexin-$V^+$ mpICs in SLE (FIG. 17C). To determine if the mpICs originate from platelets, we examined the mpICs that express CD41. We found that $CD41^+$ MPs are associated with IgG (i.e., form $CD41^+$ mpICs), only in SLE patients (FIG. 17C).

Extracellular mitochondria in SLE patients are associated with IgG. The MPs that are negative for platelet markers (CD41−) might include MPs from other cell types and potentially freeMitos. Since no markers that identifying mitochondria were not included in these analyses, whether extracellular mitochondria are present and correlate with disease characteristics cannot be extrapolated using from these data. We aimed to detect mitochondria in plasma and in mpICs using hs-FCM. For To this end, we included a membrane-permeant probe that is specific for cardiolipin (marker of mitochondria [Mitotracker, Invitrogen]) and a monoclonal antibody against the translocase of the outer membrane-22 (TOM22) [a specific surface marker of mitochondria (anti-TOM-22, BD)] in our cytofluorometric labeling and analyses (FIGS. 17D-G). We found that i) mitochondria are present in CD41+mpICs (mitoMPs) (FIG. 17E); iii) that the inclusion of the CD61 marker (GPIIIa, the platelet partner of GPIIb) marker (anti-CD61, BD) in a subset of SLE samples further confirms the platelet origin of these mitoMPs (FIG. 17F); iii) and that freeMitos (Mitotracker+TOM22+MP), which are absent in healthy individuals, are associated with autoantibodies and form freeMitoICs in SLE (FIG. 17G) (n=10). Thus, ICs in SLE patients contain mitochondria.

We verified the presence of mitochondrial immune complexes in the urine of 10 SLE patients. The details of the various specimen reviewed are provided in Table 3.

TABLE 3

Details of urine specimens and patients analyzed.

| Specimen ID | Gender | Extracellular mitochondria (per ml) | Disease Duration (years) | Age at time of assessment (years) | Total SLICC damage index score |
|---|---|---|---|---|---|
| 1 | Female | 24452000 | 32.67 | 62.71 | — |
| 2 | Female | 45863000 | 30.11 | 67.97 | 2 |
| 3 | Female | 23279000 | 19.94 | 46.53 | 1 |
| 4 | Female | 19691000 | 17.85 | 43.52 | 0 |
| 5 | Female | $1.934 \times 10^8$ | 14.64 | 29.16 | 7 |
| 6 | Female | 45221000 | 8.97 | 23.29 | 0 |
| 7 | Female | 48603000 | 8.05 | 45.62 | 2 |
| 8 | Female | 7097000 | 8.01 | 36.95 | 1 |
| 9 | Female | 16910000 | 5.89 | 32.98 | 0 |
| 10 | Female | 4128000 | 0.21 | 25.7 | 0 |

Figure 18A:
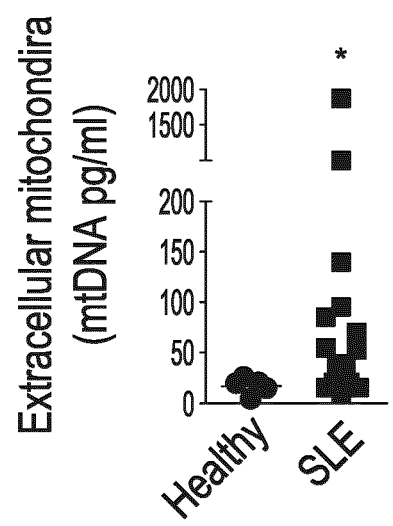
FIG. 18. Extracellular mitochondria, including freeMitos, are present in various sterile inflammatory pathologies. (A) Significant numbers of extracellular mitochondria (as detected by mtDNA quantification) are found in the urine of systemic lupus erythematosus (SLE) patients (n=15) compared to healthy volunteers (n=5). More mtDNA is detected in SLE patients than in healthy volunteers (data are mean±SEM, *P<0.05, Mann-Whitney test). (B) MitoMPs of platelet origin (as detected with anti-CD41) are found in SLE plasma compared to healthy volunteers (n=10/group; data are mean±SEM).
Figure 18B:
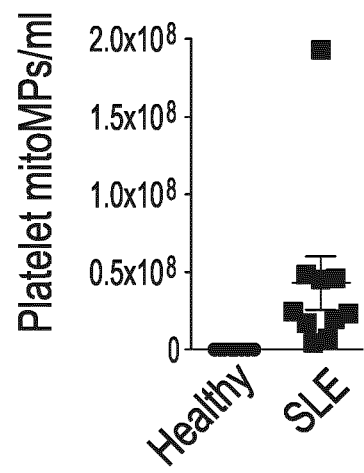

As shown in FIG. 18, the urine of patients afflicted by SLE have a significant number of extracellular mitochondrial DNA and mitochondria microparticles (FIGS. 18A and B).

REFERENCES

Boilard E, Blanco P, Nigrovic P A. Platelets: active players in the pathogenesis of arthritis and SLE. Nat Rev Rheumatol. 2012; 8(9):534-542.

Borgeat P, Picard S, Vallerand P, et al. Automated on-line extraction and profiling of lipoxygenase products of arachidonic acid by high-performance liquid chromatography. Methods Enzymol. 1990; 187:98-116.

Canaan S, Nielsen R, Ghomashchi F, Robinson B H, Gelb M H. Unusual mode of binding of human group IIA secreted phospholipase A2 to anionic interfaces as studied by continuous wave and time domain electron paramagnetic resonance spectroscopy. J Biol Chem. 2002; 277(34): 30984-30990.

Clerc, P. & Polster, B. M. Investigation of mitochondrial dysfunction by sequential microplate-based respiration measurements from intact and permeabilized neurons. PLoS One 7, e34465, (2012).

Cloutier, N. et al. The exposure of autoantigens by microparticles underlies the formation of potent inflammatory components: the microparticle-associated immune complexes. EMBO Mol Med, (2013).

Dean, W. L., Lee, M. J., Cummins, T. D., Schultz, D. J. & Powell, D. W. Proteomic and functional characterisation of platelet microparticle size classes. Thromb Haemost 102, 711-718, (2009).

Thibault, L., Beausejour, A., de Grandmont, M. J., Lemieux, R. & Leblanc, J. F. Characterization of blood components prepared from whole-blood donations after a 24-hour hold with the platelet-rich plasma method. Transfusion 46, 1292-1299, (2006).

Dussault A A, Pouliot M. Rapid and simple comparison of messenger RNA levels using real-time PCR. Biol Proced Online. 2006; 8:1-10.

Edwards, S. H., Thompson, D., Baker, S. F., Wood, S. P. & Wilton, D. C. The crystal structure of the H48Q active site mutant of human group IIA secreted phospholipase A2 at 1.5 A resolution provides an insight into the catalytic mechanism. Biochemistry 41, 15468-15476, (2002).

Grass D S, Felkner R H, Chiang M Y, et al. Expression of human group II PLA2 in transgenic mice results in epidermal hyperplasia in the absence of inflammatory infiltrate. J Clin Invest. 1996; 97(10):2233-2241.

Gyorgy B, Modos K, Pallinger E, et al. Detection and isolation of cell-derived microparticles are compromised by protein complexes resulting from shared biophysical parameters. Blood. 2011; 117(4):e39-48. Prepublished on 2010 Nov. 3 as DOI blood-2010-09-307595 [pii] 10.1182/blood-2010-09-307595.

Gyorgy B, Szabó T G, P'asztói M, et al. Membrane vesicles, current state-of-the-art: emerging role of extracellular vesicles. Cell Mol Life Sci. 2011; 68(16):2667-2688.

Gyorgy B, Szabo T G, Turiak L, et al. Improved flow cytometric assessment reveals distinct microvesicle (cell-derived microparticle) signatures in joint diseases. PLoS One. 2012; 7(11):e49726. Prepublished on 2012 Nov. 28 as DOI 10.1371/journal.pone.0049726 PONE-D-12-14720 [pii].

Bollinger, J. G., Ii, H., Sadilek, M. & Gelb, M. H. Improved method for the quantification of lysophospholipids including enol ether species by liquid chromatography-tandem mass spectrometry. J Lipid Res 51, 440-447, (2010)-A.

Bollinger, J. G. et al. Improved sensitivity mass spectrometric detection of eicosanoids by charge reversal derivatization. Anal Chem 82, 6790-6796, (2010)-B.

Flamand, N., Lefebvre, J., Surette, M. E., Picard, S. & Borgeat, P. Arachidonic acid regulates the translocation of 5-lipoxygenase to the nuclear membranes in human neutrophils. J Biol Chem 281, 129-136, (2006).

Singer A G, Ghomashchi F, Le Calvez C, Bollinger J, Bezzine S, Rouault M, Sadilek M, Nguyen E, Lazdunski M, Lambeau G, Gelb M H. Interfacial kinetic and binding properties of the complete set of human and mouse groups I, II, V, X, and XII secreted phospholipases A2. J Biol Chem. 2002 Dec. 13; 277(50):48535-49.

Soulet D, Pare A, Coste J, Lacroix S. Automated Filtering of Intrinsic Movement Artifacts during Two-Photon Intravital Microscopy. PLoS One. 2013; 8(1):e53942.

Touaibia M, Djimdé A, Cao F, Boilard E, Bezzine S, Lambeau G, Redeuilh C, Lamouri A, Massicot F, Chau F, Dong C Z, Heymans F. Inhibition of secreted phospholipase A2. 4-glycerol derivatives of 4,5-dihydro-3-(4-tetradecyloxybenzyl)-1,2,4-4H-oxadiazol-5-one with broad activities. J Med Chem. 2007 Apr. 5; 50(7):1618-26.

Oslund R C, Gelb M H. Biochemical characterization of selective inhibitors of human group IIA secreted phospholipase A(2) and hyaluronic acid-linked inhibitor conjugates. Biochemistry. 2012 Oct. 30; 51(43):8617-26.

van der Vlist E J, Nolte-'t Hoen E N, Stoorvogel W, Arkesteijn G J, Wauben M H. Fluorescent labeling of nano-sized vesicles released by cells and subsequent quantitative and qualitative analysis by high-resolution flow cytometry. Nat Protoc. 2012; 7(7):1311-1326. Pre-published on 2012 Jun. 23 as DOI nprot.2012.065 [pii] 10.1038/nprot.2012.065.

Willoughby D A, Sedgwick A D, Giroud J P, Al-Duaij A Y, de Brito F. The use of the air pouch to study experimental synovitis and cartilage breakdown. Biomed Pharmacother. 1986; 40(2):45-49.

What is claimed is:

1. A method for assessing the presence of a sterile inflammatory mediator in a biological product comprising platelets, wherein the biological product has been or is intended to be administered to a subject, said method comprising:
 a) obtaining a biological sample of the biological product susceptible of having extracellular submicrometer-sized biological components;
 b) substantially enriching extracellular submicrometer-sized components by substantially removing the platelets from the biological sample to obtain an enriched mixture;
 c) determining, in the enriched mixture, the level of at least one of a free mitochondria, a mitochondria microparticle, a degradation product of the free mitochondria and/or a degradation product of the mitochondria microparticle to obtain a test level; and
 d) comparing the test level with a control level, wherein the control level is associated with the absence of the sterile inflammatory mediator; and
 e) characterizing the biological sample as having the inflammatory mediator and as susceptible of causing a sterile inflammatory reaction in the subject if the test level is determined to be higher than the control level or as lacking the inflammatory mediator if the test level is determined to be equal to or lower than the control level;
wherein the sterile inflammatory reaction is at least one of a febrile non-hemolytic reaction, an anaphylactic reaction, an adverse reaction following a transfusion and transfusion related acute lung injury (TRALI).

2. The method of claim 1, wherein the biological sample comprises nucleated cells and step b) further comprises substantially removing nucleated cells from the biological sample.

3. The method of claim 1, wherein the determination of the presence or the absence of the at least one of the degradation product of the free mitochondria and/or the degradation product of the mitochondria microparticle excludes detecting mitochondrial DNA.

4. The method of claim 1, further comprising, after step b) and prior to step c), isolating the at least one of the free mitochondria and/or the mitochondria microparticle from the enriched mixture to provide an isolated mixture.

5. The method of claim 4, wherein step c) further comprises obtaining the test level from the isolated mixture.

6. The method of claim 1, wherein step c) further comprises determining the presence or the absence of mitochondrial activity in the enriched mixture or the isolated mixture for determining the test level.

7. The method of claim 6, wherein mitochondrial activity is determined by measuring oxygen consumption, oxidative phosphorylation, carbon dioxide production and/or membrane potential.

8. The method of claim 1, wherein step c) further comprises determining the test level by flow cytometry or by mass spectrometry.

9. The method of claim 1, wherein step c) further comprises determining the presence or the absence of an association between secreted phospholipase A2 group IIA ($sPLA_2$-IIA) and the free mitochondria and/or the mitochondria microparticle.

10. The method of claim 9, wherein step c) further comprises determining the presence or the absence of the association by measuring the enzymatic activity of $sPLA_2$-IIA.

11. The method of claim 9, wherein step c) further comprises determining the presence or absence of the association by detecting the presence or the absence of an $sPLA_2$-IIA polypeptide.

12. The method of claim 1, further comprising administering the biological product to the subject when the biological product is characterized as lacking the susceptibility of causing the sterile inflammatory reaction.

13. The method of claim 1, further comprising avoiding administering the biological product characterized as being susceptible of causing the sterile inflammatory reaction.

14. The method of claim 1, further comprising treating the sterile inflammatory reaction in the subject when the biological product has been administered to the subject and is characterized as being susceptible of causing the sterile inflammatory reaction.

* * * * *

```
                         SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide

<400> SEQUENCE: 1
acgcctgagc cctatctatt a                                                  21

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide

<400> SEQUENCE: 2
gttgacctgt tagggtgaga ag                                                 22

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide

<400> SEQUENCE: 3
tgacaagcgc ctatagcact cgaa                                               24

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide

<400> SEQUENCE: 4
ggaacaaccc tagtcgaatg aa                                                 22

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
gctagggccg cgataataaa                                                    20

<210> SEQ ID NO 6
<211> LENGTH: 24
<212> TYPE: DNA
<213> ORGANISM: Artificial Sequence
<220> FEATURE:
```

```
<223> OTHER INFORMATION: Oligonucleotide

<400> SEQUENCE: 6
acaaagccac cttgacccga ttct                                              24
```